US012644113B2

(12) United States Patent
Abate et al.

(10) Patent No.: US 12,644,113 B2
(45) Date of Patent: Jun. 2, 2026

(54) SELECTIVE AND HIGH-RESOLUTION PRINTING OF SINGLE CELLS

(71) Applicant: The Regents of the University of California, Oakland, CA (US)

(72) Inventors: Adam R. Abate, San Francisco, CA (US); Pengfei Zhang, San Francisco, CA (US); Russell Cole, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 1021 days.

(21) Appl. No.: 17/785,339

(22) PCT Filed: Dec. 16, 2020

(86) PCT No.: PCT/US2020/065298
§ 371 (c)(1),
(2) Date: Jun. 14, 2022

(87) PCT Pub. No.: WO2021/126969
PCT Pub. Date: Jun. 24, 2021

(65) Prior Publication Data
US 2023/0053160 A1     Feb. 16, 2023

Related U.S. Application Data

(60) Provisional application No. 62/949,147, filed on Dec. 17, 2019.

(51) Int. Cl.
*G01N 21/64*       (2006.01)
*B01L 3/00*        (2006.01)
(Continued)

(52) U.S. Cl.
CPC ........ *C12N 11/08* (2013.01); *B01L 3/502761* (2013.01); *B33Y 10/00* (2014.12);
(Continued)

(58) Field of Classification Search
CPC .............. C12N 11/08; B01L 3/502761; B01L 2200/0652; B01L 2300/0645;
(Continued)

(56) References Cited

U.S. PATENT DOCUMENTS

2009/0244180 A1  10/2009 Panchawagh et al.
2009/0308473 A1  12/2009 Masataka
2018/0056288 A1*  3/2018 Abate ................ G01N 15/1484

FOREIGN PATENT DOCUMENTS

WO      WO2014/028378      2/2014

OTHER PUBLICATIONS

Abate et al., (2010) "High-throughput injection with microfluidics using picoinjectors." PNAS, vol. 107, No. 45, pp. 19163-19166.
(Continued)

*Primary Examiner* — Jennifer Wecker
*Assistant Examiner* — Oyeleye Alexander Alabi
(74) *Attorney, Agent, or Firm* — Edward J. Baba; Jenny L. Buchbinder; Bozicevic, Field & Francis LLP

(57) ABSTRACT

Methods for on-demand printing discrete entities including, e.g., cells, media or reagents to substrates are provided. In certain aspects, the methods include manipulating qualities of the entities or biological components thereof. In some embodiments, the methods may be used to create arrays of microenvironments and/or for two and three-dimensional printing of tissues or structures and/or for in situ printing for microsurgeries. Systems and devices for practicing the subject methods are also provided.

31 Claims, 26 Drawing Sheets

(51) Int. Cl.

| | |
|---|---|
| *B33Y 10/00* | (2015.01) |
| *B33Y 30/00* | (2015.01) |
| *B33Y 50/00* | (2015.01) |
| *B82Y 5/00* | (2011.01) |
| *B82Y 30/00* | (2011.01) |
| *B82Y 40/00* | (2011.01) |
| *C07F 5/02* | (2006.01) |
| *C09B 57/00* | (2006.01) |
| *C09K 11/06* | (2006.01) |
| *C12N 11/08* | (2020.01) |
| *C12Q 1/6844* | (2018.01) |
| *G01N 1/30* | (2006.01) |
| *G01N 15/10* | (2024.01) |
| *G01N 15/1404* | (2024.01) |
| *G01N 15/1409* | (2024.01) |
| *G01N 15/1429* | (2024.01) |
| *G01N 15/149* | (2024.01) |
| *G01N 27/626* | (2021.01) |
| *G01N 31/22* | (2006.01) |
| *G01N 33/483* | (2006.01) |
| *G01N 33/543* | (2006.01) |
| *G01N 33/58* | (2006.01) |
| *G01N 33/68* | (2006.01) |

(52) U.S. Cl.

CPC .............. *B33Y 30/00* (2014.12); *B33Y 50/00* (2014.12); *B01L 2200/0652* (2013.01); *B01L 2200/16* (2013.01); *B01L 2300/0645* (2013.01); *B01L 2300/0654* (2013.01); *B01L 2300/0864* (2013.01); *B01L 2400/027* (2013.01); *B01L 2400/0424* (2013.01)

(58) Field of Classification Search

CPC ..... B01L 2300/0654; B01L 2300/0864; B01L 2400/027; B01L 2400/0424; B01L 2300/0883; B01L 2400/0415; B01L 3/0268; B33Y 30/00; G01N 15/1459; G01N 33/56966; G01N 35/08; G01N 35/1009; G01N 15/149; G01N 2015/1415; B41J 2202/02; B41J 2/03

See application file for complete search history.

(56) References Cited

OTHER PUBLICATIONS

Agresti et al., (2010) "Ultrahigh-throughput screening in drop-based microfluidics for directed evolution." PNAS, vol. 107, No. 9, pp. 4004-4009.

Ahn et al., (2006) "Electrocoalescence of drops synchronized by size-dependent flow in microfluidic channels." Appl. Phys. Lett., vol. 88, 264105, 3 pages.

Link et al., (2004) "Geometrically Mediated Breakup of Drops in Microfluidic Devices." *Phys. Rev. Lett.*, vol. 92, No. 5, 054503, 4 pages.

Priest et al., (2006) "Controlled electrocoalescence in microfluidics: Targeting a single lamella." Applied Physics Letters, vol. 89, 134101, 4 pages.

Song et al., "On-Chip Titration of an Anticoagulant Argatroban and Determination of the Clotting Time within Whole Blood or Plasma Using a Plug-Based Microfluidic System." Anal. Chem., 2006, vol. 78, No. 14, pp. 4839-4849.

* cited by examiner

One cell type          multiple cell types

Controlled spheroid/organoid formation
(cell numbers, cell ratios)

Dynamically controlled 3D spheroid formation

3T3 cells green
Varying from 0-100

HepG2 cells red
100 cells for each spheroid

SELECTIVE AND HIGH-RESOLUTION PRINTING OF SINGLE CELLS

CROSS REFERENCE TO APPLICATIONS

This application claims priority to International Application PCT/US2020/065298, filed Dec. 16, 2020, which, pursuant to 35 U.S.C. § 119 (e), claims priority to the filing date of U.S. Provisional Application No. 62/949,147, filed Dec. 17, 2019, the disclosures of which are incorporated herein by reference.

INTRODUCTION

Bioprinting has emerged as a powerful tool to spatially control the placement of cells and has been widely used in many applications including tissue engineering, organoids, stem cell research, and high-throughput screening. Our body functions with trillions of molecular distinct cells interacting, and thus building biological constructs at the single cell level can mostly mimic life. However, current bioprinting technologies based on extrusion, laser, and inkjet are not capable of printing with control over single cells, which means they cannot print at single cell resolution and print multiple types of cells with a controllable way. Also, several existing single cell bioprinters lack either throughput or printing resolution. Moreover, current bioprinters need large equipment and complicated systems and is difficult to achieve in situ bioprinting, which is a promising approach for regenerative medicine and clinic. Accordingly, there is a need for bioprinter that is capable of rapidly printing single cells at the single cell resolution onto various substrates.

SUMMARY

Methods for delivering discrete entities including, e.g., cells, media and/or reagents encapsulated therein to substrates are provided. In certain aspects, the methods include manipulating qualities of the discrete entities or biological materials encapsulated therein. In some embodiments, the methods may be used to create arrays of microenvironments and/or for two and three-dimensional printing of tissues or structures. Systems and devices for practicing the subject methods are also provided.

The present disclosure provides methods of delivering discrete entities to a substrate, for example, by: flowing a plurality of discrete entities through an air flow via a microfluidic device comprising an air/liquid co-flow junction; directing the air flow and one or more of the plurality of discrete entities through the air/liquid co-flow junction to the substrate; and affixing the one or more of the plurality of discrete entities to the substrate via a force, wherein the force is selected from a gravitational force, an electrical force, a magnetic force, and combinations thereof.

The present disclosure also provides methods of sorting microdroplets for example, by: flowing a plurality of microdroplets through a microfluidic device comprising an air/liquid co-flow junction; detecting via a detector a property of one or more of the plurality of microdroplets; and applying an electric field to selectively deflect one or more of the plurality of microdroplets based on the detection of the property.

The present disclosure also provides methods of printing and detecting one or more cells, for example, by: encapsulating cells in droplets comprising an aqueous fluid to provide cell-comprising droplets; flowing a plurality of droplets comprising the cell-comprising droplets through an air flow via a microfluidic device comprising an air/liquid co-flow junction; directing the air flow and a plurality of the cell-comprising droplets through the air/liquid co-flow junction to the wound area; and affixing the plurality of cell-comprising droplets to the wound area via a force, wherein the force is selected from a gravitational force, an electrical force, a magnetic force, and combinations thereof, to provide a first layer of cell-comprising droplets.

The present disclosure also provides methods of printing one or more cell layers, for example, by: encapsulating cells in droplets comprising an aqueous fluid to provide cell-comprising droplets; flowing a plurality of droplets comprising the cell-comprising droplets through an air flow via a microfluidic device comprising an air/liquid co-flow junction; directing the air flow and a plurality of the cell-comprising droplets through the air/liquid co-flow junction to a substrate; and affixing the plurality of the cell-comprising droplets to the substrate via a force, wherein the force is selected from a gravitational force, an electrical force, a magnetic force, and combinations thereof, to provide a first layer of cell-comprising droplets.

The present disclosure also provides methods of treating a wound area, for example, by: printing one or more cell layers on the wound area, wherein the method comprises: encapsulating cells in droplets comprising an aqueous fluid to provide cell-comprising droplets; flowing a plurality of droplets comprising the cell-comprising droplets through an air flow via a microfluidic device comprising an air/liquid co-flow junction; directing the air flow and a plurality of the cell-comprising droplets through the air/liquid co-flow junction to the wound area; and affixing the plurality of the cell-comprising droplets to the wound area via a force, wherein the force is selected from a gravitational force, an electrical force, a magnetic force, and combinations thereof, to provide a first layer of cell-comprising droplets.

The present disclosure also provides methods of printing and detecting one or more cells, for example, by: encapsulating cells in droplets comprising an aqueous fluid to provide cell-comprising droplets; flowing a plurality of droplets comprising the cell-comprising droplets through an air flow via a microfluidic device comprising an air/liquid co-flow junction; directing the air flow and a plurality of the cell-comprising droplets through the air/liquid co-flow junction to a substrate; affixing the plurality of the cell-comprising droplets to the substrate via a force, wherein the force is selected from a gravitational force, an electrical force, a magnetic force, and combinations thereof, to provide a first layer of cell-comprising droplets; and detecting one or more of the cells in the affixed cell-comprising droplets, a component of one or more of the cells in the affixed cell-comprising droplets or a product of one or more of the cells in the affixed cell-comprising droplets.

The present disclosure also provides methods of printing a three-dimensional structure, for example, by: flowing discrete entities through an air flow via a microfluidic device comprising an air/liquid co-flow junction; directing the air flow and a first plurality of the discrete entities through the air/liquid co-flow junction to a substrate; affixing the first plurality of the discrete entities to the substrate via a force, wherein the force is selected from a gravitational force, an electrical force, a magnetic force, and combinations thereof, to provide a first layer thereon; directing the air flow and a second plurality of the discrete entities through the air/liquid co-flow junction to the first layer; affixing the second plurality of the discrete entities to the substrate via a force, wherein the force is selected from a gravitational force, an electrical force, a magnetic force, and combinations thereof, to provide a second layer thereon; and one or more additional directing steps in which a plurality of the discrete entities are directed through the air/liquid co-flow junction to an immediately preceding layer to provide a subsequent layer thereon, wherein a multilayer, three-dimensional structure is provided.

The present disclosure also provides methods of delivering droplets from an air/liquid co-flow junction, for example, by: flowing a plurality of droplets through an air flow via a microfluidic device, wherein the microfluidic device comprises an air/liquid co-flow junction and a sorter; detecting one or more of the plurality of droplets to provide one or more detected droplets; sorting via the sorter the one or more detected droplets from the plurality of droplets; and directing the air flow and the one or more detected droplets through the air/liquid co-flow junction.

The present disclosure also provides methods of affixing a droplet to a substrate, for example, by: delivering a droplet in an air flow from a microfluidic device comprising an air/liquid co-flow junction, through the air/liquid co-flow junction, to a substrate surface; positioning the droplet on the substrate surface; and affixing the droplet to the substrate surface via a force, wherein the force is selected from a gravitational force, an electrical force, a magnetic force, and combinations thereof.

The present disclosure also provides methods of moving an affixed droplet on a substrate, for example, by: delivering a droplet in an air flow from a microfluidic device comprising an air/liquid co-flow junction, through the air/liquid co-flow junction, to a substrate surface; affixing the droplet to the substrate surface via a force, wherein the force is selected from a gravitational force, an electrical force, a magnetic force, and combinations thereof; and modulating the force so as to move the droplet from its affixed location to another location and/or applying a second force, which is sufficient, either alone or in combination with the modulated force, to move the droplet from its affixed location to another location.

The present disclosure also provides methods of adding reagents to a droplet, for example, by: delivering a first droplet in an air flow from a microfluidic device comprising an air/liquid co-flow junction, through the air/liquid co-flow junction, to a substrate surface; affixing the droplet to the substrate surface via a force, wherein the force is selected from a gravitational force, an electrical force, a magnetic force, and combinations thereof; delivering a second droplet comprising a reagent to the same location as the first droplet affixed to the substrate surface or a location adjacent the first droplet on the substrate surface; and coalescing the first droplet and the second droplet such that the contents of the first droplet and the second droplet are combined.

The present disclosure also provides methods of adding reagents to a droplet, for example, by: delivering a droplet in an air flow from a microfluidic device comprising an air/liquid co-flow junction, through the air/liquid co-flow junction, to a substrate surface; affixing the droplet to the substrate surface via a force, wherein the force is selected from a gravitational force, an electrical force, a magnetic force, and combinations thereof; inserting an orifice fluidically connected to a reagent source into the droplet; and injecting via the orifice one or more reagents into the droplet.

The present disclosure also provides methods of recovering all or a portion of an affixed droplet, for example, by: delivering a droplet in an air flow from a microfluidic device comprising an air/liquid co-flow junction, through the air/liquid co-flow junction, to a substrate surface; affixing the droplet to the substrate surface via a force, wherein the force is selected from a gravitational force, an electrical force, a magnetic force, and combinations thereof; and recovering all or a portion of the affixed droplet.

The present disclosure also provides methods of manipulating an affixed droplet, for example, by: delivering a droplet in an air flow from a microfluidic device comprising an air/liquid co-flow junction, through the air/liquid co-flow junction, to a substrate surface; affixing the droplet to the substrate surface via a force, wherein the force is selected from a gravitational force, an electrical force, a magnetic force, and combinations thereof; and modulating the immediate environment of the droplet, thereby modulating the contents of the droplet.

The present disclosure also provides methods of manipulating a droplet, for example, by: delivering a droplet in an air flow from a microfluidic device comprising an air/liquid co-flow junction, through the air/liquid co-flow junction, to a substrate surface; affixing the droplet to the substrate surface via a force, wherein the force is selected from a gravitational force, an electrical force, a magnetic force, and combinations thereof; at least partially solidifying the affixed droplet; adding a miscible fluid to the affixed droplet; and modulating a chemical composition of the miscible fluid, thereby modulating the affixed droplet.

The present disclosure also provides methods of porating a cell within an affixed droplet, for example, by: delivering a droplet in an air flow from a microfluidic device comprising an air/liquid co-flow junction, through the air/liquid co-flow junction, to a substrate surface, wherein the droplet comprises a cell; positioning the droplet on the substrate surface; affixing the droplet to the substrate surface via a force, wherein the force is selected from a gravitational force, an electrical force, a magnetic force, and combinations thereof; and porating the cell within the droplet.

The present disclosure also provides methods of delivering discrete entities to a substrate, for example, by: flowing a plurality of first discrete entities in an air flow through a microfluidic device comprising a first air/liquid co-flow junction; directing the one or more of the plurality of first discrete entities through the first air/liquid co-flow junction to the substrate; flowing a plurality of second discrete entities through a second microfluidic comprising a second air/liquid co-flow junction device; directing the one or more of the plurality of second discrete entities through the second air/liquid co-flow junction to the substrate; and affixing the one or more of the plurality of first discrete entities and the one or more of the plurality of second discrete entities to the substrate via a force, wherein the force is selected from a gravitational force, an electrical force, a magnetic force, and combinations thereof.

The present disclosure also provides methods of delivering discrete entities to a substrate, for example, by: flowing a plurality of discrete entities in an air flow through a microfluidic device comprising an air/liquid co-flow junction, wherein the microfluidic device comprises a plurality of air/liquid co-flow junctions; directing the one or more of the plurality of discrete entities through a first air/liquid co-flow junction of the plurality of air/liquid co-flow junctions to the substrate; directing a second one or more of the plurality of discrete entities through a second air/liquid co-flow junction of the plurality of air/liquid co-flow junctions to the substrate; and affixing the first one or more of the plurality of first discrete entities and the second one or more of the plurality of discrete entities to the substrate via a force, wherein the force is selected from a gravitational force, an electrical force, a magnetic force, and combinations thereof.

The present disclosure also provides methods of synthesizing a polymer on a substrate, for example, by: flowing a first droplet in an air flow through a microfluidic device comprising an air/liquid co-flow junction, wherein the first droplet comprises a first polymer or a first monomer; directing the first droplet through the air/liquid co-flow junction to the substrate; affixing the first droplet to the substrate via a force, wherein the force is selected from a gravitational force, an electrical force, a magnetic force, and combinations thereof, flowing a second droplet in an air flow through the microfluidic device, wherein the second droplet comprises a second polymer or a second monomer; directing the second droplet through the air/liquid co-flow junction to the first droplet affixed at the predetermined location; and incubating the first and second droplets under conditions sufficient for the contents of the first and second droplets to come into contact and for the first polymer or first monomer to form a covalent bond with the second polymer or monomer, thereby generating a synthesized polymer.

The present disclosure also provides methods of printing microarrays, for example, by: delivering a plurality of droplets in an air flow from a microfluidic device comprising an air/liquid co-flow junction, through the air/liquid co-flow junction, to a substrate surface, wherein each of the plurality of droplets comprises a molecule; positioning the droplets on the substrate surface; affixing the droplets at predetermined locations to the substrate surface via a force, wherein the force is selected from a gravitational force, an electrical force, a magnetic force, and combinations thereof, and incubating the substrate under conditions suitable for chemical bonding of the molecules comprised by the affixed droplets to the substrate surface, thereby providing an array of substrate-bound molecules.

The present disclosure also provides methods of manipulating cells or embryos, for example, by: flowing a plurality of droplets in an air flow through a microfluidic device comprising an air/liquid co-flow junction, wherein each droplet of the plurality of droplets comprises an aqueous fluid and a fertilized egg cell or embryo; directing the plurality of droplets through the air/liquid co-flow junction to a substrate; affixing the plurality of droplets to the substrate via a force, wherein the force is selected from a gravitational force, an electrical force, a magnetic force, and combinations thereof, wherein the substrate comprises on a surface thereof a layer of fluid; detecting within the affixed plurality of droplets the development of one or more embryos; and selecting and recovering an embryo from the affixed droplets.

The present disclosure also provides methods of manipulating cells or embryos, for example, by: flowing a plurality of droplets in an air flow through a microfluidic device comprising an air/liquid co-flow junction, wherein each droplet of the plurality of droplets comprises an aqueous fluid and an unfertilized egg cell; directing the plurality of droplets through the air/liquid co-flow junction to a substrate; fertilizing one or more of the egg cells in the plurality of droplets; affixing the plurality of droplets to the substrate, via a force, wherein the force is selected from a gravitational force, an electrical force, a magnetic force, and combinations thereof, wherein the substrate comprises on a surface thereof a layer of fluid; detecting within the affixed droplets the development of an embryo; and selecting and recovering specific embryos from the affixed droplets.

The present disclosure also provides systems and devices which may be utilized in the implementation of the methods describe herein. For example, the present disclosure provides a droplet printer including, for example: a microfluidic device comprising an air/liquid co-flow junction; one or more droplet makers and one or more flow channels, wherein the one or more flow channels are fluidically connected to the one or more droplet makers and configured to receive one or more droplets therefrom; the air/liquid co-flow junction connected to one or more of the one or more flow channels and one or more air channels, wherein the one or more air channels are connected to one or more air flow controllers; a droplet sorter, which selectively sorts droplets; and an automated system integrated with the air/liquid co-flow junction, wherein the automated system (a) selectively positions the air/liquid co-flow junction in proximity to a substrate during operation or (b) selectively positions the substrate in proximity to the air/liquid co-flow junction during operation, such that a droplet can be ejected from the air/liquid co-flow junction and deposited on the substrate.

The present disclosure also provides a microfluidic device including, for example, an air/liquid co-flow junction; one or more flow channels; one or more air channels; one or more air flow controllers connected to the one or more air channels; and an electrode configured to selectively apply an electric field.

The present disclosure also provides a system including, for example, a droplet printer including a substrate surface for receiving one or more droplets deposited by the air/liquid co-flow junction of the droplet printer; and one or more of: (a) a temperature control module operably connected to the droplet printer, (b) a detection means operably connected to the droplet printer, (c) an incubator operably connected to the droplet printer, and a conveyor configured to convey the substrate from a first droplet receiving position to one or more of (a)-(c).

The present disclosure also provides a system including, for example, a microfluidic device including a substrate surface for receiving one or more discrete entities deposited by the air/liquid co-flow junction of the microfluidic device; and one or more of: (a) a temperature control module operably connected to the microfluidic device, (b) a detection means operably connected to the microfluidic device, (c) an incubator operably connected to the microfluidic device, and a conveyor configured to convey the substrate from a first discrete entity receiving position to one or more of (a)-(c).

The present disclosure also provides electrode array systems, for example, an electrode array system including: an array of individually controllable electrodes embedded in a substrate material; a power source; and a controller, wherein the controller is configured to selectively enable or disable an electrical connection between the power source and each individually controllable electrode in the array thereby providing an active an inactive electrode respectively, and wherein, each active electrode is capable of affixing a droplet or a discrete entity to a surface of the substrate material in proximity to the active electrode when said droplet or discrete entity is deposited in proximity to the active electrode.

BRIEF DESCRIPTION OF THE DRAWINGS

The invention may be best understood from the following detailed description when read in conjunction with the accompanying drawings. Included in the drawings are the following figures:

FIG. 2A shows discrete entities being ejected through the air-liquid co-flow junction and being sorted to be deposited on a substrate (not pictured) or not being sorted and flowing into a waste reservoir. FIG. 2B shows the discrete entities flowing through the air-liquid co-flow junction and delivery orifice of the microfluidic device. FIG. 2C provides a photograph of the microfluidic device at the air-liquid co-flow junction illustrating the discrete entities flowing through the air-liquid co-flow junction and delivery orifice of the microfluidic device.

FIG. 3A shows a representative image of droplets printed using the microfluidic device. FIG. 3B shows droplets printed using the microfluidic device of this disclosure with a Z number range from 0.35 to 34.4. FIG. 3C shows the distribution of droplet diameter in Panel A, indicating good uniformity of printed droplets.

FIG. 4A shows a schematic of applying a voltage to an electrode to sort droplets. FIG. 4B shows the horizontal distance traveled by a droplet (measured from the point the droplet would have travelled had there been no application of voltage) on the Y-axis and the voltage applied on the electrode of the X-axis. The droplets travel greater horizontal distances upon application of increasing voltages at the electrode. FIG. 4C shows an embodiment of droplets passing through the air-liquid co-flow junction and delivery orifice upon application of voltage at the electrode. In this embodiment, all unsorted droplets are collected in a waste reservoir upon application of voltage to the electrode. FIG. 4D provides an embodiment of droplets passing through the air-liquid co-flow junction and delivery orifice when no voltage is applied at the electrode. In this embodiment, all sorted droplets are deposited on a substrate (not shown) when no voltage is applied to the electrode.

FIG. 6A shows sorting for single cells with Calcein green stain at 500 Hz or 1000 Hz (top) and sorting multiple cells with Calcein green or Calcein red-orange stains (bottom). FIG. 6B shows viability and proliferation of sorted cells compared to unsorted cells at Days, 1 3 and 4. FIG. 6C shows that there is no observable difference in the viability and proliferation of sorted cells and unsorted cells 1, 2 3 or 4 days after sorting.

FIG. 7A shows droplet arrays printing in which the distance between delivery orifice and substrate was set of 3 mm (top) and printing performed with a distance between delivery orifice and substrate of 3 mm, 4 mm, 5 mm, and 6 mm, respectively (bottom). FIG. 7B depicts single cell printing of NIH 3T3 cell suspensions stained with Calcein green (white dots) and Calcein red-orange (gray dots). The distance between two spots was set to 400 μm. FIG. 7C illustrates Calcein green (white) and Calcein red-orange (gray) stained cells used for printing "UCSF" pattern (top), with a distance of 20 μm between two neighboring droplets. Calcein green stained cells (white dots) were used to print a second "UCSF" pattern (bottom) with the distance of 10 μm between two neighboring droplets. FIG. 7D illustrates Calcein green (white dots) and Calcein red-orange (gray dots) stained cells used for printing well-defined cell clusters into nanowells.

FIG. 8A provides a schematic of controlled spheroid or organoid formation using the microfluidic device to print either cells of one type or cells of multiple types. FIG. 8B shows a schematic of dynamically controlled 3D spheroid formation formed by using the microfluid device of the instant disclosure to print cells of one type and then printing cells of a different type on the printed cells one day later. FIG. 8C shows ten spheroids formed by printing and incubating 200 NIH 3T3 cells into wells with 200 μL complete growth medium. FIG. 8D illustrates sizes of spheroids formed by printing and incubating 10, 50, 100, 200 or 500 NIH 3T3 cells into wells with 200 μL complete growth medium after two days of culturing. FIG. 8E illustrates spheroids formed by printing 50, 100, 200 or 500 Cell-Tracker Green CMFDA (gray) stained NIH 3T3 cells (top) and NIH 3T3 cells stained with CellTracker Green CMFDA (gray) and CellTracker Red CMTPX (white) in the ratios of 200:50, 200:100, 200:200 and 200:300 (middle and bottom). For the bottom and middle panels, the 200 CellTracker Green CMFDA (gray) stained NIH 3T3 cells were first printed into each well, and after one day of culturing, the CellTracker Red CMTPX stained NIH 3T3 cells were printed into the same wells.

DETAILED DESCRIPTION

Figure 1:
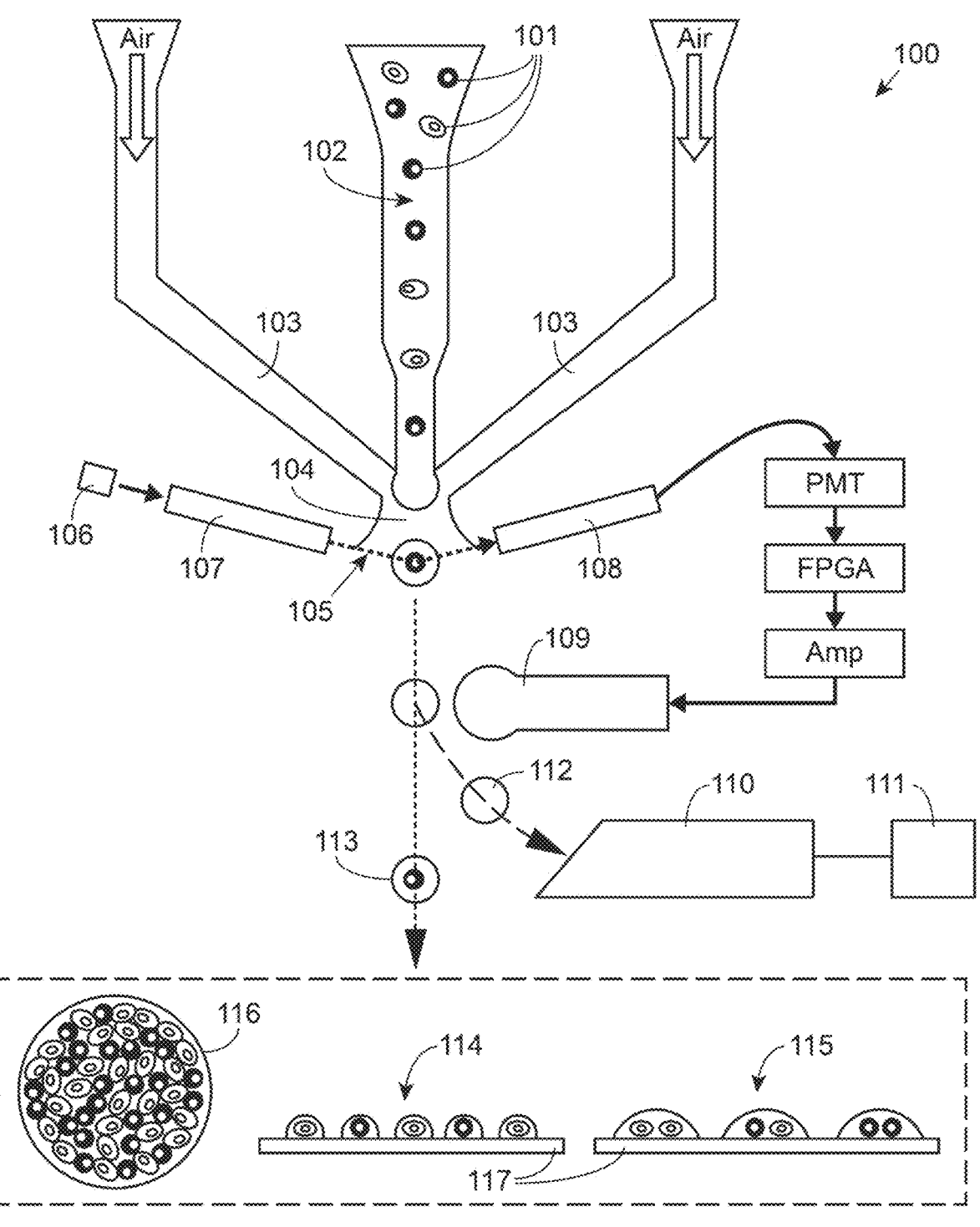
FIG. 1 depicts an embodiment of the microfluidic device of the instant disclosure.

Methods for delivering discrete entities including, e.g., cells, media and/or reagents encapsulated therein to substrates are provided. In certain aspects, the methods include manipulating qualities of the discrete entities or biological materials encapsulated therein. In some embodiments, the methods may be used to create arrays of microenvironments and/or for two and three-dimensional printing of tissues or structures. Systems and devices for practicing the subject methods are also provided.

The subject methods and devices may find use in a wide variety of applications, such as increasing the accuracy and/or efficiency of printing, e.g., microdroplet printing, and in assays involving, for example, well-plate analysis. Assays which can be performed in accordance with the subject disclosure may be relevant for the detection of cancer or other diseases, monitoring disease progression, analyzing the DNA or RNA content of cells, and a variety of other applications in which it is desired to detect and/or quantify specific components of a discrete entity.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials may now be described. Any and all publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a droplet" includes a plurality of such droplets and reference to "the discrete entity" includes reference to one or more discrete entities, and so forth.

It is further noted that the claims may be drafted to exclude any element, e.g., any optional element. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Further, the dates of publication provided may be different from the actual publication dates which may need to be independently confirmed. To the extent the definition or usage of any term herein conflicts with a definition or usage of a term in an application or reference incorporated by reference herein, the instant application shall control.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

As summarized above, aspects of the disclosed subject matter include methods for the delivery of discrete entities, such as droplets, to one or more substrates and in some embodiments, affixing the discrete entities thereto. Aspects of the present disclosure include methods for printing one or more medium or cell layers as well as the detection of one or more qualities of components which are applied to a substrate. For example, some embodiments include methods for the detection, quantification, and/or genotyping of cells, e.g. normal cells (i.e., non-tumor cells), or tumor cells positioned on a substrate.

The subject methods, in some embodiments, include flowing a plurality of discrete entities through an air flow via a microfluidic device comprising an air/liquid co-flow junction. The methods also may include directing the air flow and one or more of the plurality of discrete entities through a portion of a microfluidic device, such as the air/liquid co-flow junction, to a substrate and/or affixing the one or more discrete entities to a substrate. Discrete entities may be affixed to a substrate, for example, by one or more forces, such as an electrical (e.g., dielectrophoretic), gravitational, and/or magnetic force, and combinations thereof.

Discrete entities as used or generated in connection with the subject methods, devices, and/or systems may be sphere shaped or they may have any other suitable shape, e.g., an ovular or oblong shape. Discrete entities as described herein may include a liquid phase and/or a solid phase material. In some embodiments, discrete entities according to the present disclosure include a gel material. In some embodiments, the subject discrete entities have a dimension, e.g., a diameter, of or about 1.0 μm to 1000 μm, inclusive, such as 1.0 μm to 750 μm, 1.0 μm to 500 μm, 1.0 μm to 100 μm, 1.0 μm to 10 μm, or 1.0 μm to 5 μm, inclusive. In some embodiments, discrete entities as described herein have a dimension, e.g., diameter, of or about 1.0 μm to 5 μm, 5 μm to 10 μm, 10 μm to 100 μm, 100 μm to 500 μm, 500 μm to 750 μm, or 750 μm to 1000 μm, inclusive. Furthermore, in some embodiments, discrete entities as described herein have a volume ranging from about 1 fL to 1 nL, inclusive, such as from 1 fL to 100 μL, 1 fL to 10 μL, 1 fL to 1 μL, 1 fL to 100 fL, or 1 fL to 10 fL, inclusive. In some embodiments, discrete entities as described herein have a volume of 1 fL to 10 fL, 10 fL to 100 fL, 100 fL to 1 μL, 1 μL to 10 μL, 10 μL to 100 μL or 100 μL to 1 nL, inclusive. In addition, discrete entities as described herein may have a size and/or shape such that they may be produced in, on, or by a microfluidic device and/or flowed from or applied by a microfluidic device.

In some embodiments, the discrete entities as described herein are droplets. The terms "drop," "droplet," and "microdroplet" are used interchangeably herein, to refer to small, generally spherically structures, containing at least a first fluid phase, e.g., an aqueous phase (e.g., water). Droplets may be sized and/or shaped as described herein for discrete entities. For example, droplets according to the present disclosure generally range from 1 μm to 1000 μm, inclusive, in diameter. Droplets according to the present disclosure may be used to encapsulate cells, nucleic acids (e.g., DNA), enzymes, reagents, and a variety of other components. The term droplet may be used to refer to a droplet produced in, on, or by a microfluidic device and/or flowed from or applied by a microfluidic device.

FIG. 1 presents a non-limiting, simplified representation of one type of a microfluidics system and method according to the present disclosure. The particular embodiment depicted in FIG. 1 shows the delivery of discrete entities (droplets are illustrated by way of example) to a substrate. In one such method, discrete entities 101, e.g., droplets, are prepared using a device, e.g., a microfluidic device 100 comprising a droplet maker. A variety of suitable droplet makers are known in the art, which may be used, e.g., droplet makers described in PCT Publication No. WO 2014/028378, the disclosure of which is incorporated by reference herein in its entirety and for all purposes. In some embodiments, the discrete entities are of more than one type, e.g., more than one composition and/or size, such as a first type, e.g., a type containing one or more cells of interest, and a second type, e.g., a type not containing one or more cells of interest. In some embodiments, the discrete entities may contain one or more beads, such as magnetic beads and/or conductive beads.

In some embodiments of the disclosed methods, microfluidic devices are utilized which include one or more droplet makers configured to form droplets from a fluid stream. Suitable droplet makers include selectively activatable droplet makers and the methods may include forming one or more discrete entities via selective activation of the droplet maker. The methods may also include forming discrete entities using a droplet maker, wherein the discrete entities include one or more entities which differ in composition.

Once prepared, the discrete entities or droplets may be moved through the liquid 102, e.g., moved and/or flowed to another portion of the microfluidic device 100, such as via the flow channel to the air-liquid co-flow junction 104. The air-liquid co-flow junction 104 is connected to one or more air channels 103. In certain embodiments, the air channels are connected to air flow controllers to control and direct the air flow in the air channels. In some embodiments, the microfluidic device comprises a sorter configured to detect and/or separate discrete entities, e.g., discrete entities having different types, e.g., different compositions and/or sizes, such as a first type, e.g., a type containing one or more cells of interest, and a second type, e.g., a type not containing one or more cells of interest. As such, a sorter may provide one or more sorted discrete entities 113 (e.g., one or more discrete entities including a cell and/or nucleic acid of interest) and direct them via the delivery orifice 105 for delivery to a substrate 117. A sorter 103 may also provide one or more sorted discrete entities 112 (e.g., one or more discrete entities not including a cell and/or nucleic acid of interest) and direct them to a waste reservoir 110, optionally connected to a vacuum pump 111.

In some embodiments, the discrete entities not sorted for delivery via a delivery orifice, are recovered and/or recycled by, for example, being re-injected into the liquid 102 upstream of the sorter. Various embodiments of the methods disclosed herein include repeated recycling of discrete entities not selected for delivery through the delivery orifice in a particular pass through the sorter. Sorting, according to the subject embodiments, is described in further detail below.

As discussed above, a sorted subset of discrete entities of interest, e.g., discrete entities 113, (e.g., discrete entities containing one or more cells of interest), may in some embodiments, be directed through a delivery orifice 105 of a microfluidic device 100 to a substrate 117. In some embodiments, a microfluidic device 100, or a portion thereof, e.g., a delivery orifice 105, delivers discrete entities to a substrate, e.g., a substrate 117, or a portion thereof, by dispensing the discrete entities into air in proximity to a surface of the substrate 117.

A delivery orifice 105 as described herein, e.g., a delivery orifice of a microfluidic nozzle as described herein, will generally have dimensions that are similar to the size of the droplets to be delivered therethrough. Accordingly, in some embodiments, a delivery orifice as described herein has a diameter of from about 1 μm to about 1000 μm, inclusive, e.g., from about 10 μm to about 300 μm, inclusive. In some embodiments, a delivery orifice as described herein has a diameter of from about 1 μm to about 10 μm, from about 10 μm to about 100 μm, from about 100 μm to about 500 μm, or from about 500 μm to about 1000 μm, inclusive.

The nozzle can be molded as part of a microfluidic sorter as described herein, or can be a separate part that is mated with a microfluidic sorter as described herein. Suitable materials for the nozzle may include, e.g., polymeric tubing, small bore hypodermic tubing, and modified glass capillaries.

In certain embodiments of the subject systems, devices and methods, now described with reference to FIG. 1, illustrates a microfluidic system including a microfluidic device including a sorter comprising a laser 106 connected to optical fibers configured to apply excitation energy 107, which apply excitation energy to the discrete entities 101 flowing through the delivery orifice 105 via the air-liquid co-flow junction 104, and optical fibers configured to collect a signal produced by the application of excitation energy 108 to the discrete entities 101. The sorter may further comprise an electrode 109 that can sort the discrete entities 101 based on detection of property, e.g., an optical property, by the laser 106 and optical fiber system 107 and 108. In some embodiments, when the electrode 109 is turned on by application of a voltage, discrete entities 101 are deposited on the substrate 117. In certain embodiments, when the electrode 109 is turned on by application of a voltage, the discrete entities are directed to the waste reservoir 110. The subject systems, devices and methods can be used to print single cell arrays 114, multiple cells arrays 115 and/or spheroids 116. Positioning of the substrate 117 relative to the delivery orifice 105 and/or the air-liquid co-flow junction 104 is achieved, for example, with a computer controlled mechanical stage. Alternatively, or in addition, the nozzle may be provided as part of a print head, e.g., a computer controlled print head, which is movable relative to substrate 117. In certain embodiment, embedded electrodes features are patterned beneath the surface of substrate 117.

Sorting may be accomplished, e.g., by applying an electric field via an electrode, e.g., a liquid electrode including, e.g., an electrode salt solution.

In certain embodiments, liquid electrodes include liquid electrode channels filled with a conducting liquid (e.g. salt water or buffer) and situated at positions in the microfluidic device where an electric field is desired. In some embodiments, the liquid electrodes are energized using a power supply or high voltage amplifier. In certain embodiments, the liquid electrode channel includes an inlet port so that a conducting liquid can be added to the liquid electrode channel. Such conducting liquid may be added to the liquid electrode channel, for example, by connecting a tube filled with the liquid to the inlet port and applying pressure. In some embodiments, the liquid electrode channel also includes an outlet port for releasing conducting liquid from the channel. As discussed above, some embodiments, such as those described in connection with FIG. 1, include affixing one or more discrete entities 101 to a substrate 117.

Figure 2A:
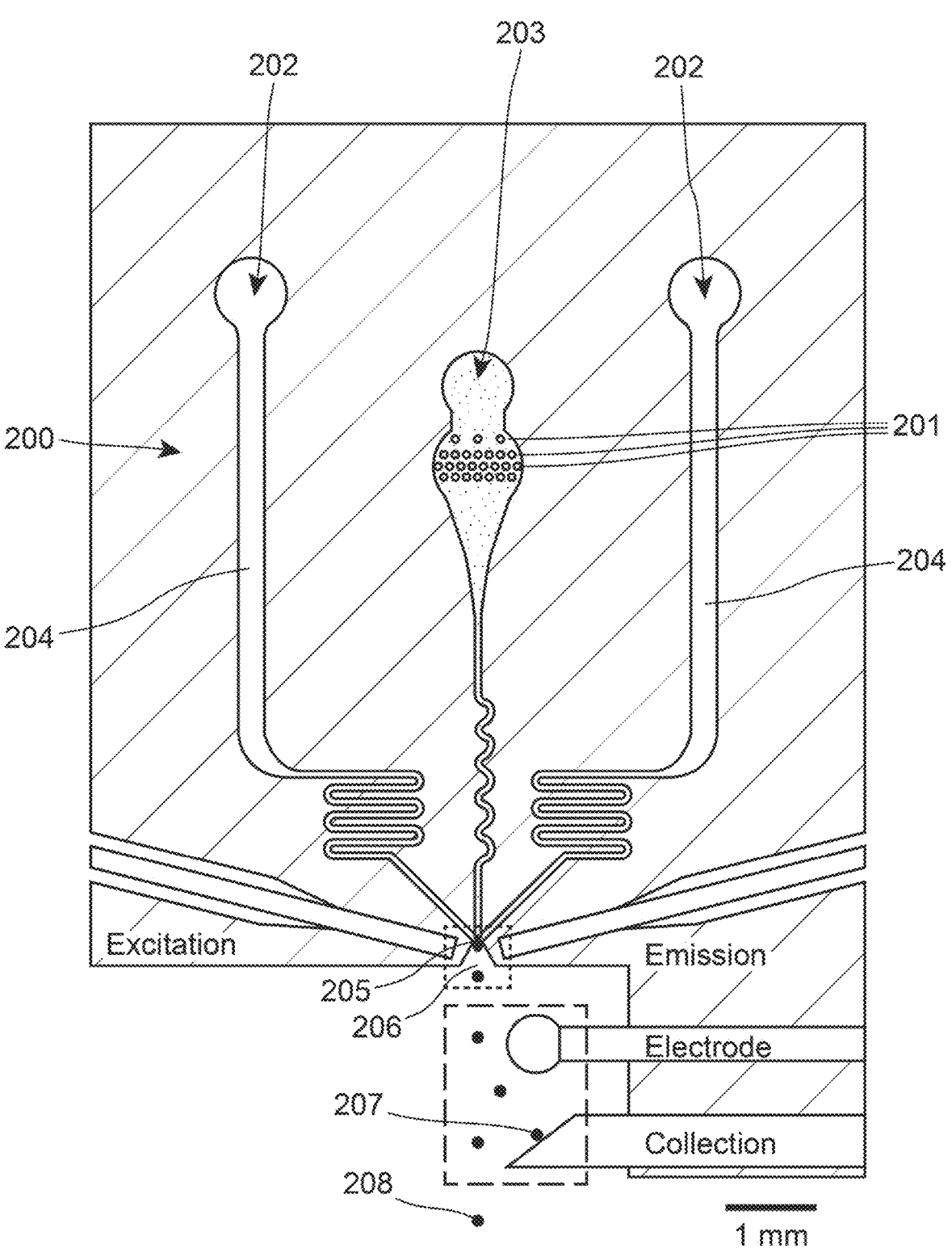
FIGS. 2A-2C, illustrate embodiments of the microfluidic device of the instant disclosure.
Figure 2B:
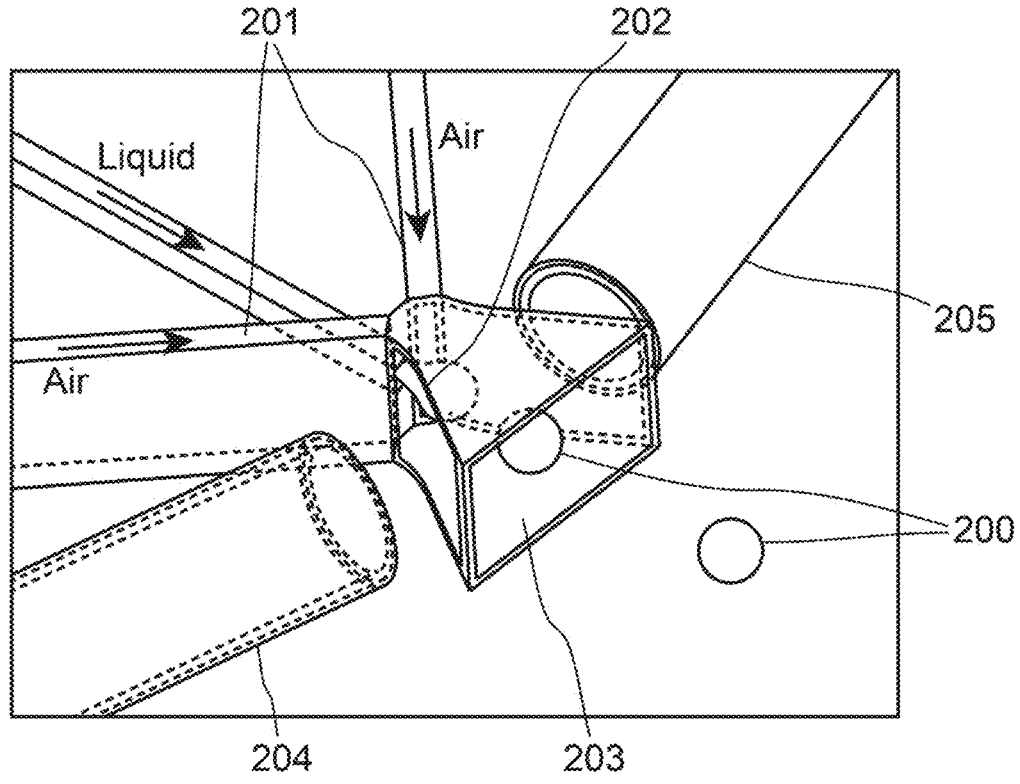
Figure 2C:
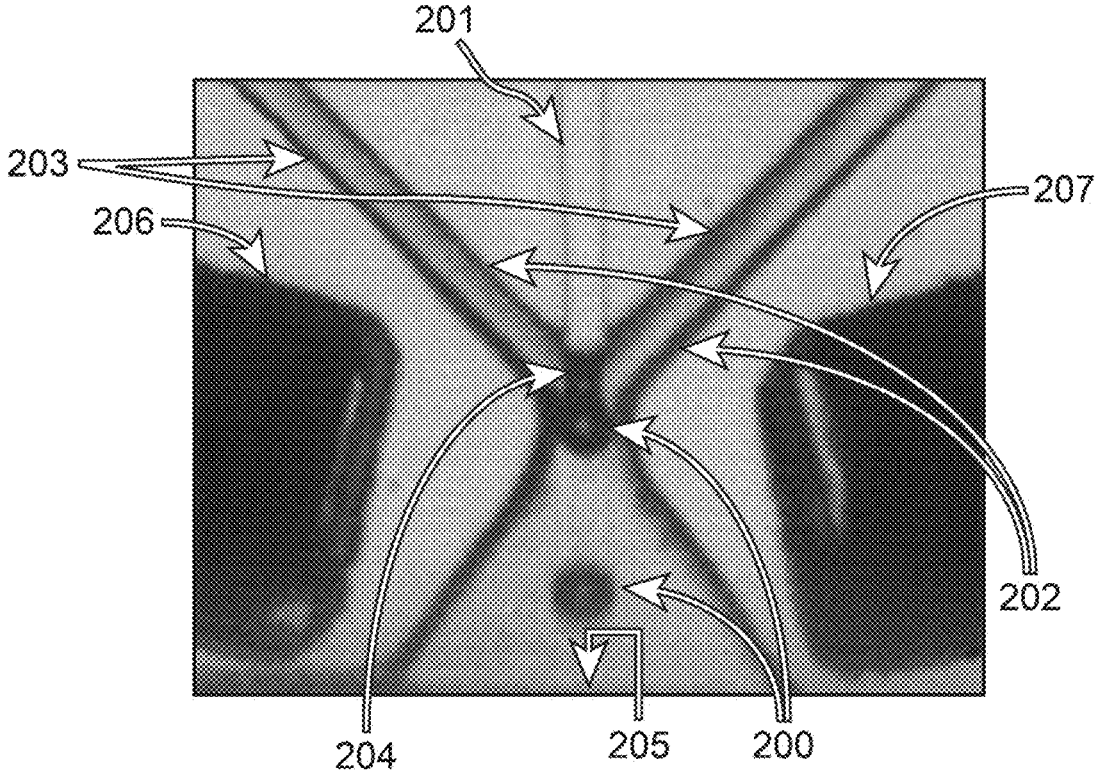
Figure 3A:
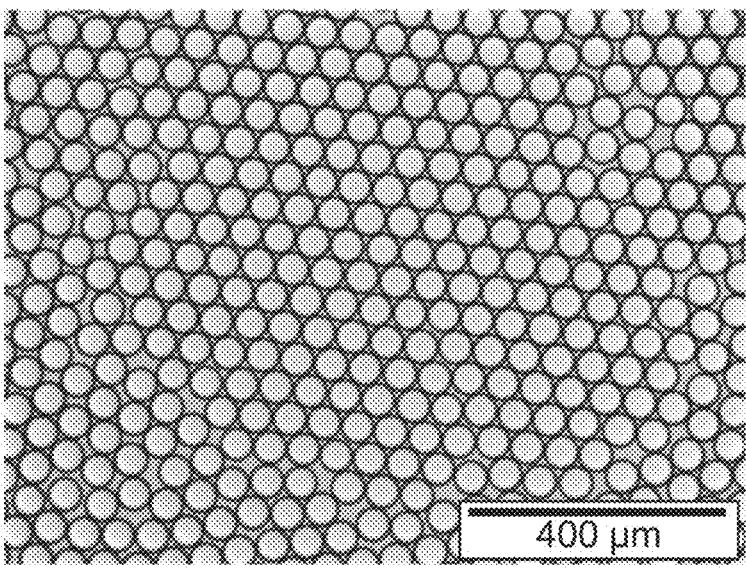
FIGS. 3A-3C, illustrate droplets printed using the microfluidic device of the instant disclosure.
Figure 3B:
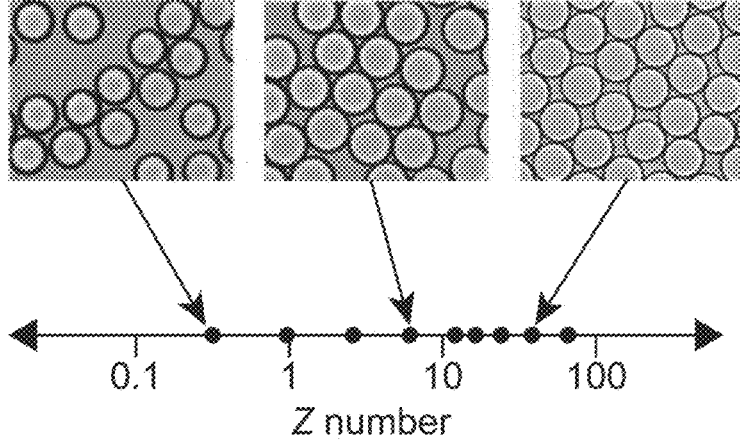
Figure 3C:
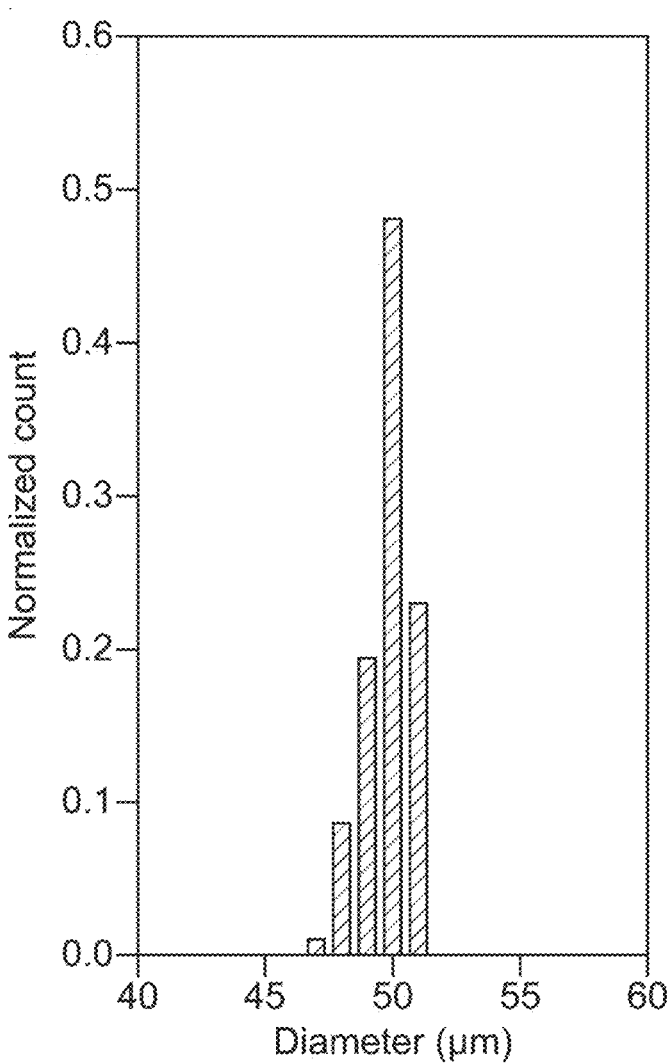
Figure 4A:
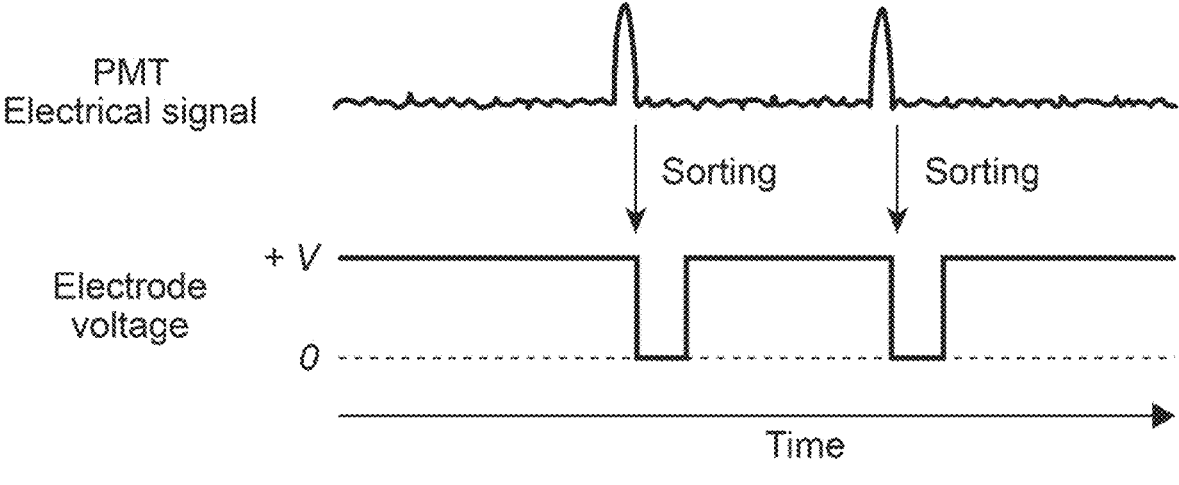
FIGS. 4A-4D, illustrate embodiments of sorting using the microfluidic device of the instant disclosure.
Figure 4B:
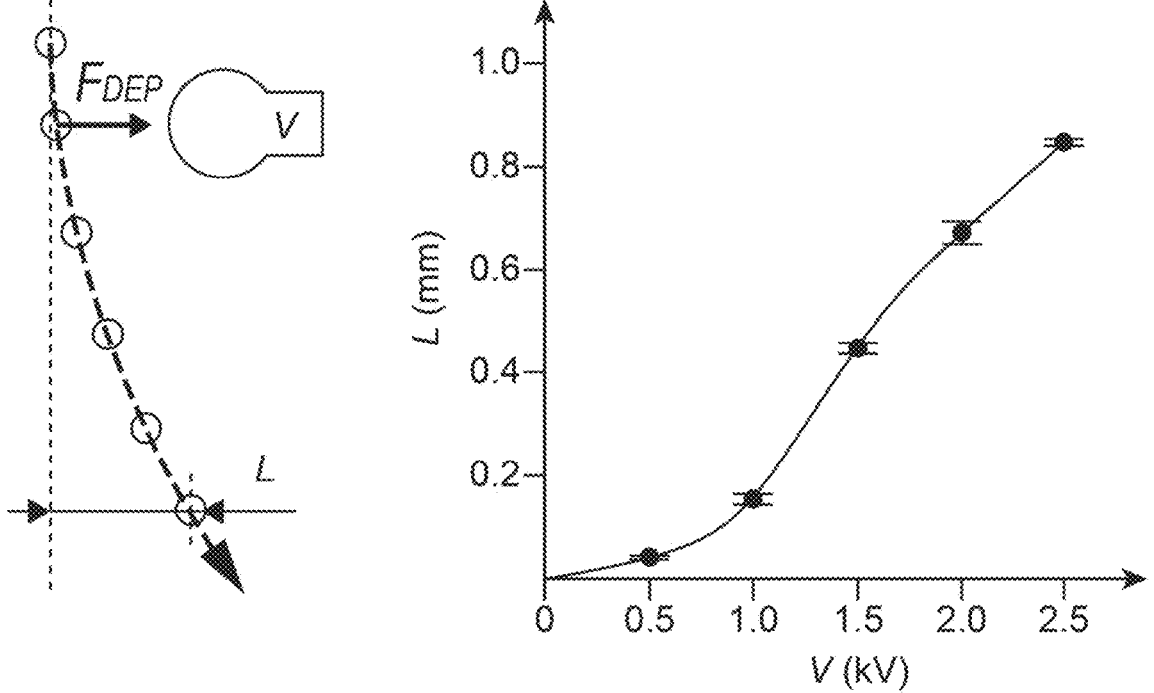
Figure 4C:
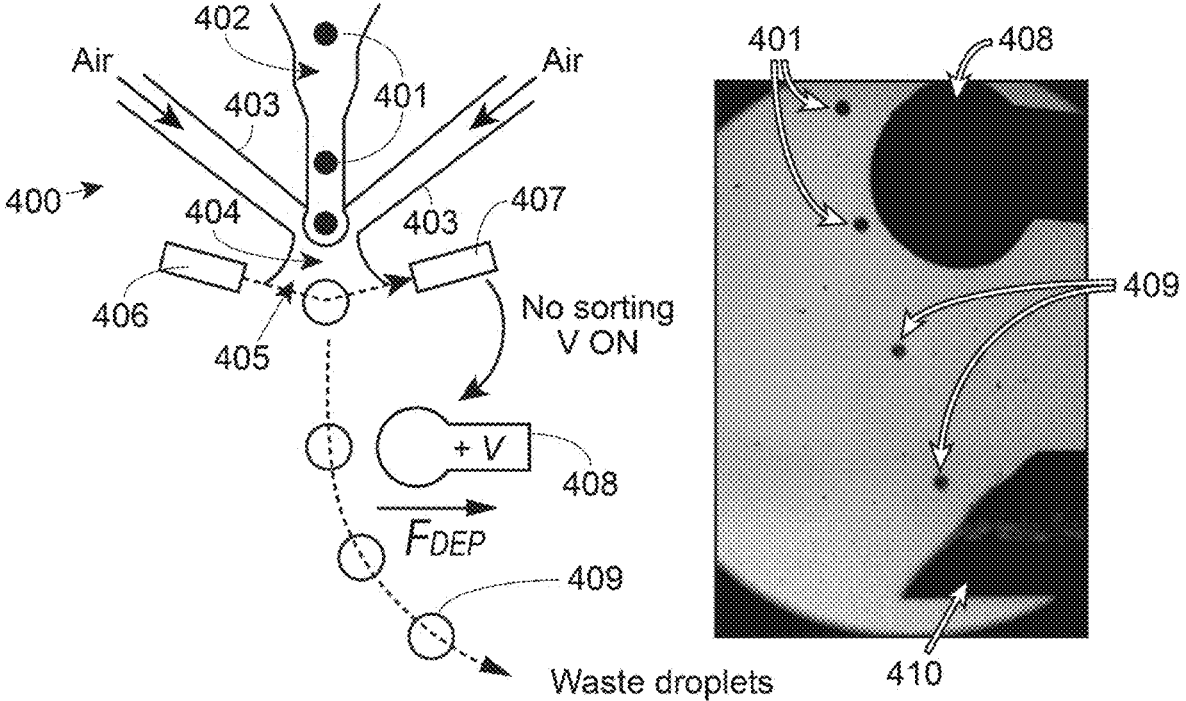
Figure 4D:
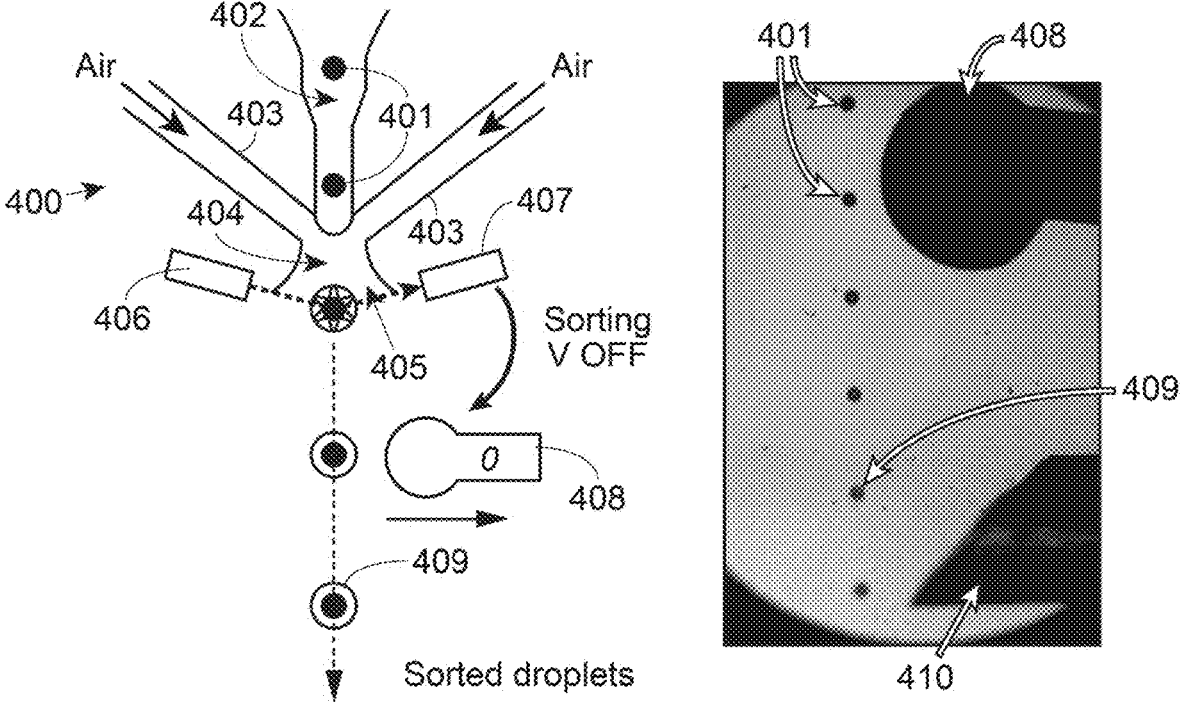
Figure 5:
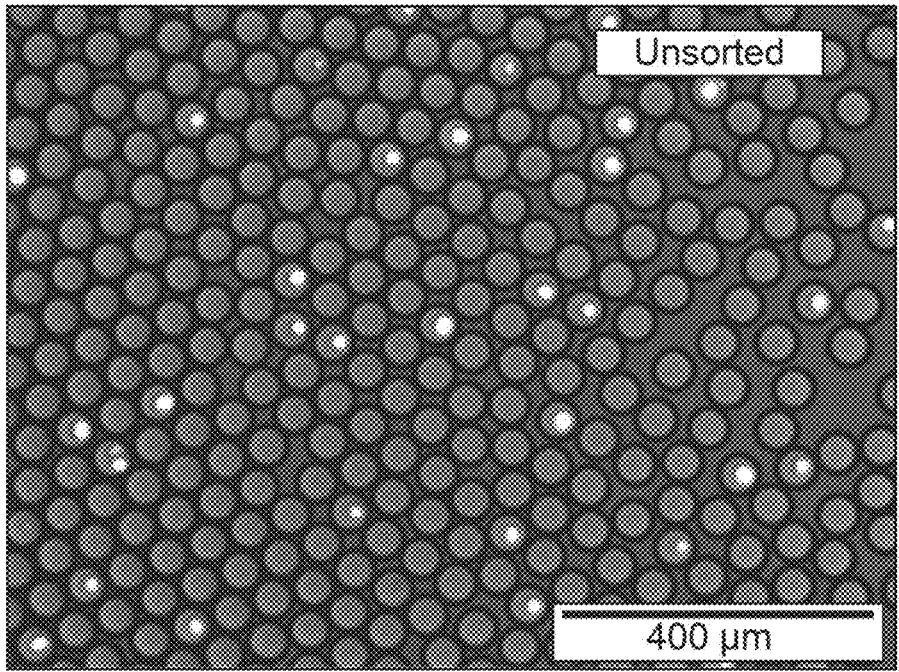
FIG. 5 illustrates sorted droplets printed using the microfluidic device of the instant disclosure (bottom panel) and a photograph of unsorted droplets.
Figure 5:
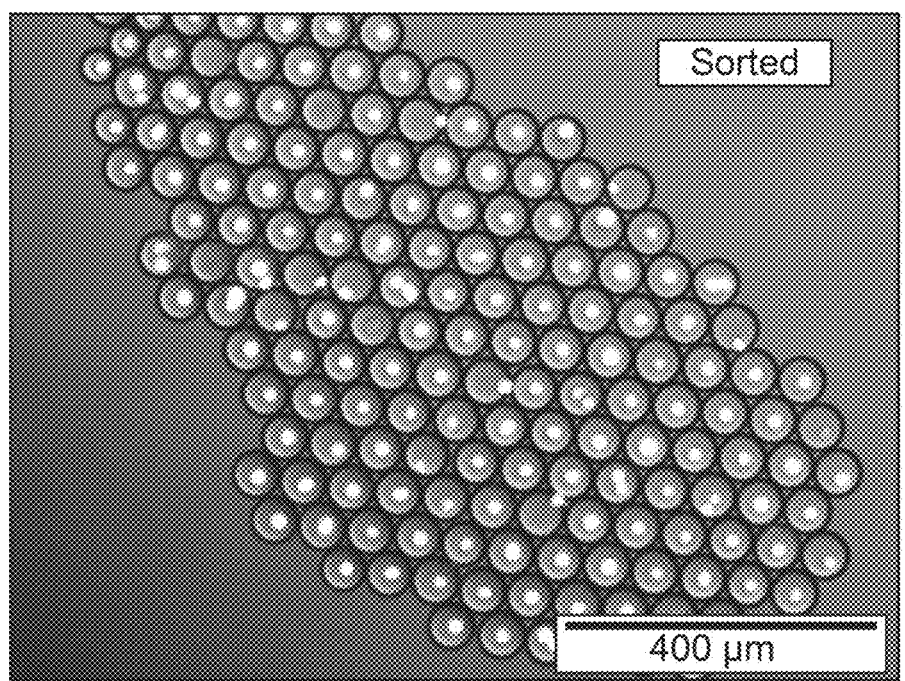
Figure 6A:
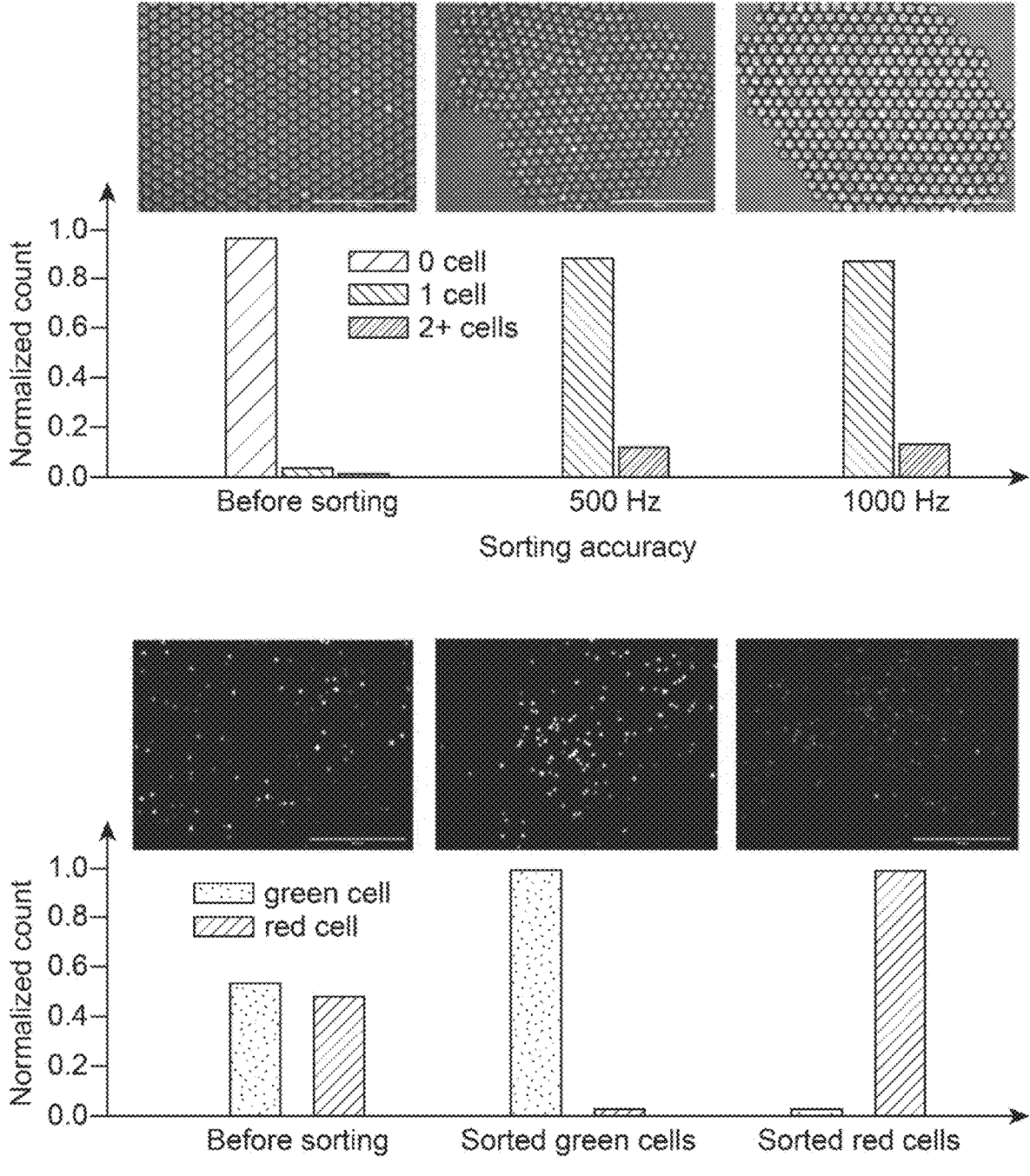
FIGS. 6A-6C, illustrates sorting accuracy and viability of cells sorted using the microfluidic device of the instant disclosure.
Figure 6B:
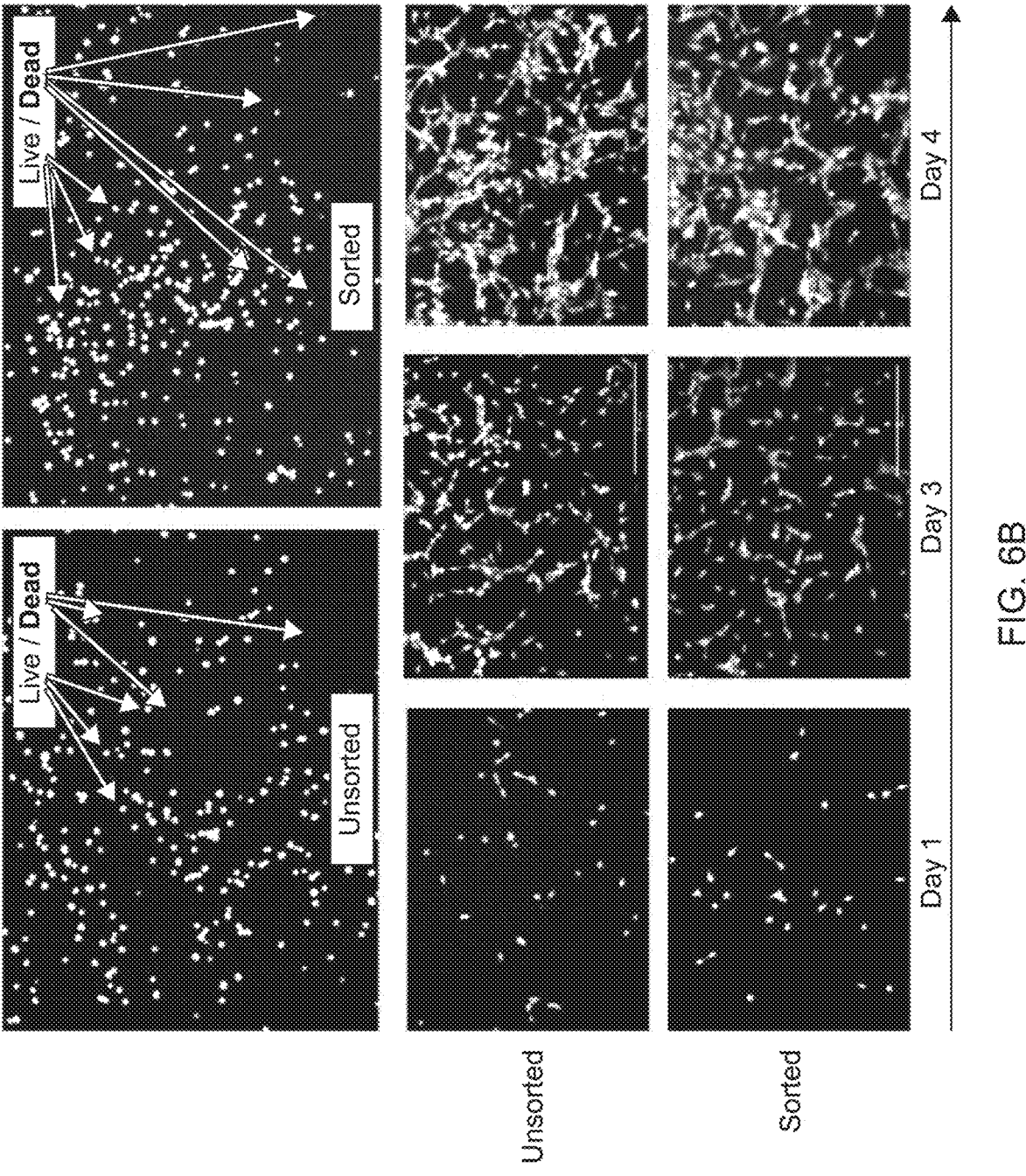
Figure 6C:
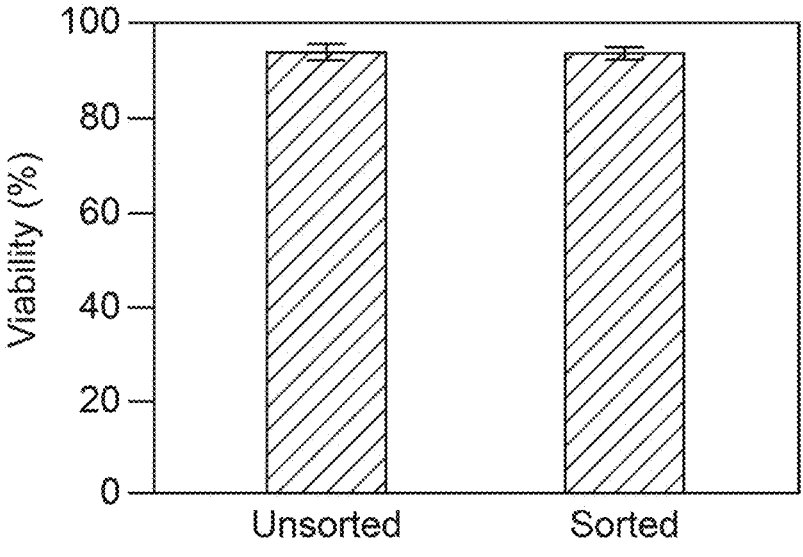
Figure 6C:
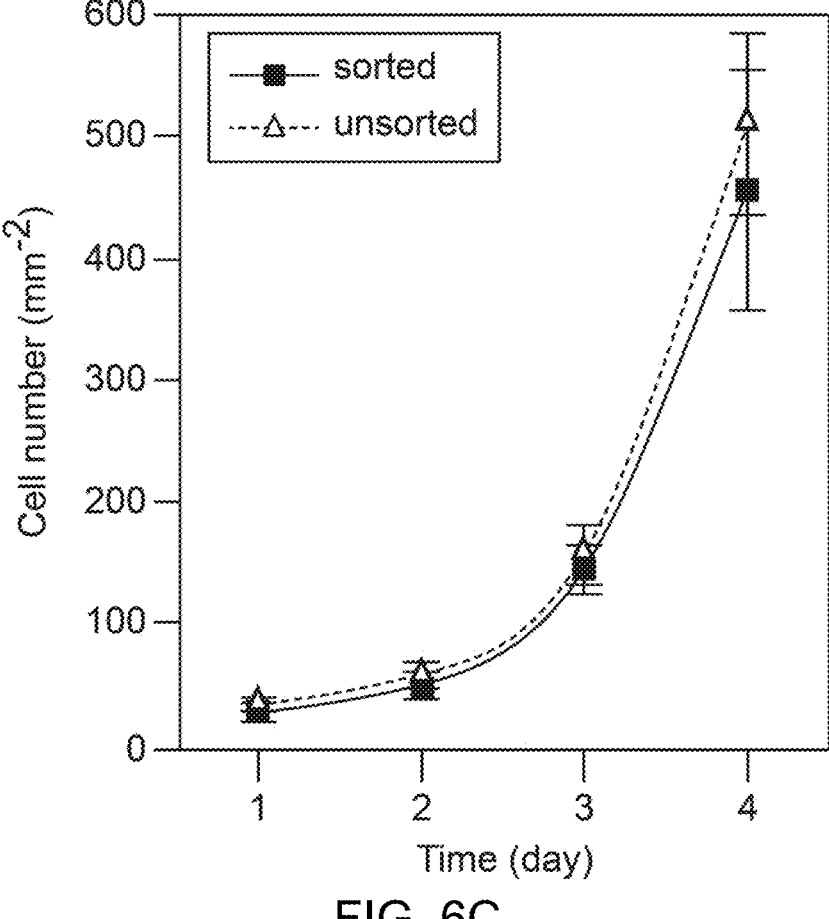
Figure 7A:
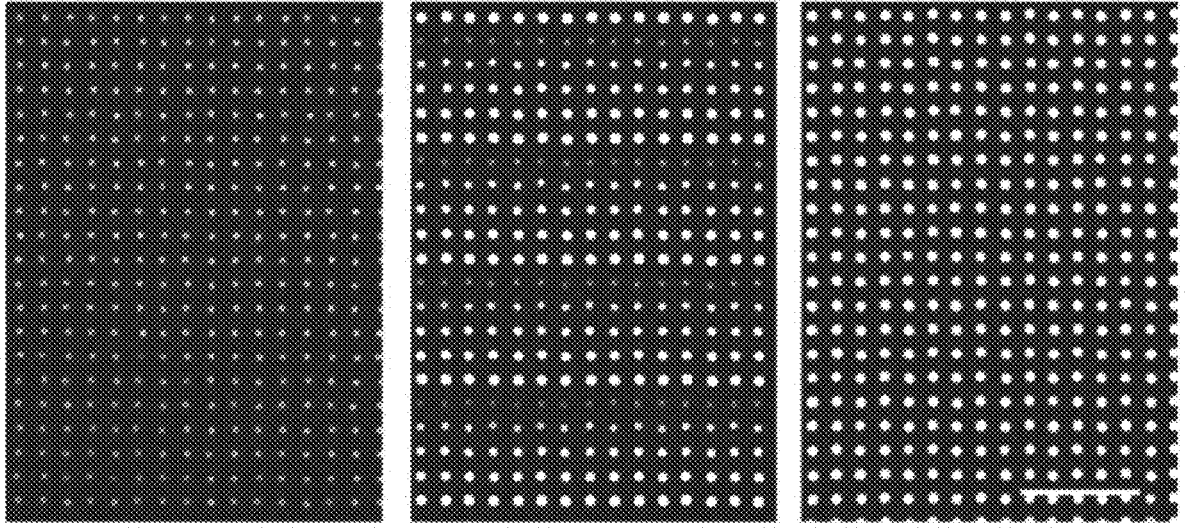
FIGS. 7A-7D, illustrates that the microfluidic device of this disclosure enables high-resolution single cell printing.
Figure 7A:
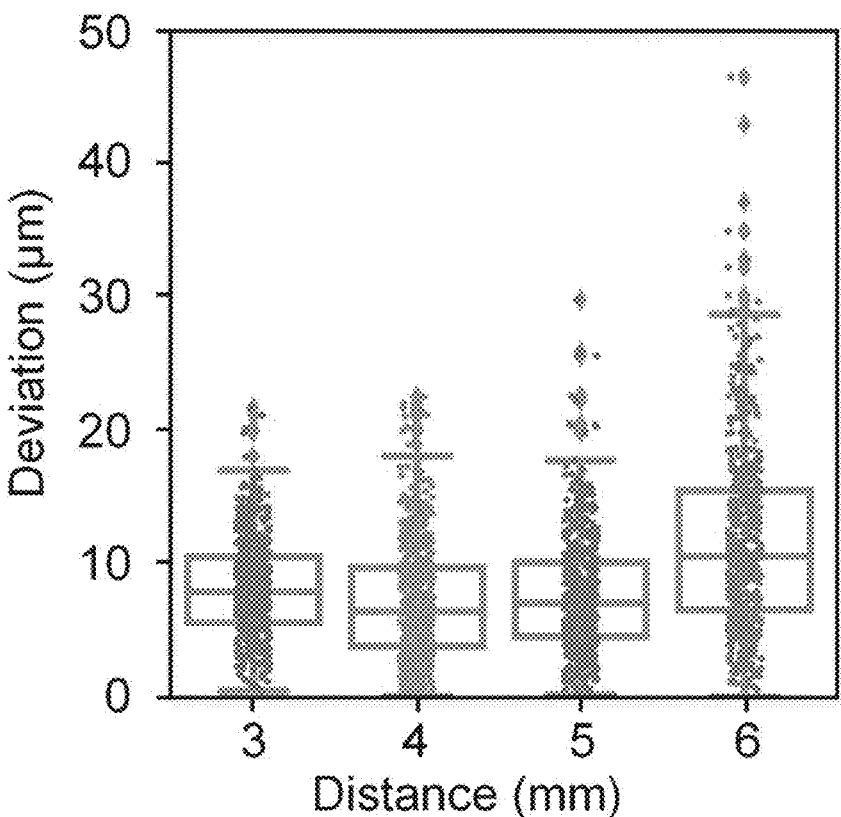
Figure 7B:
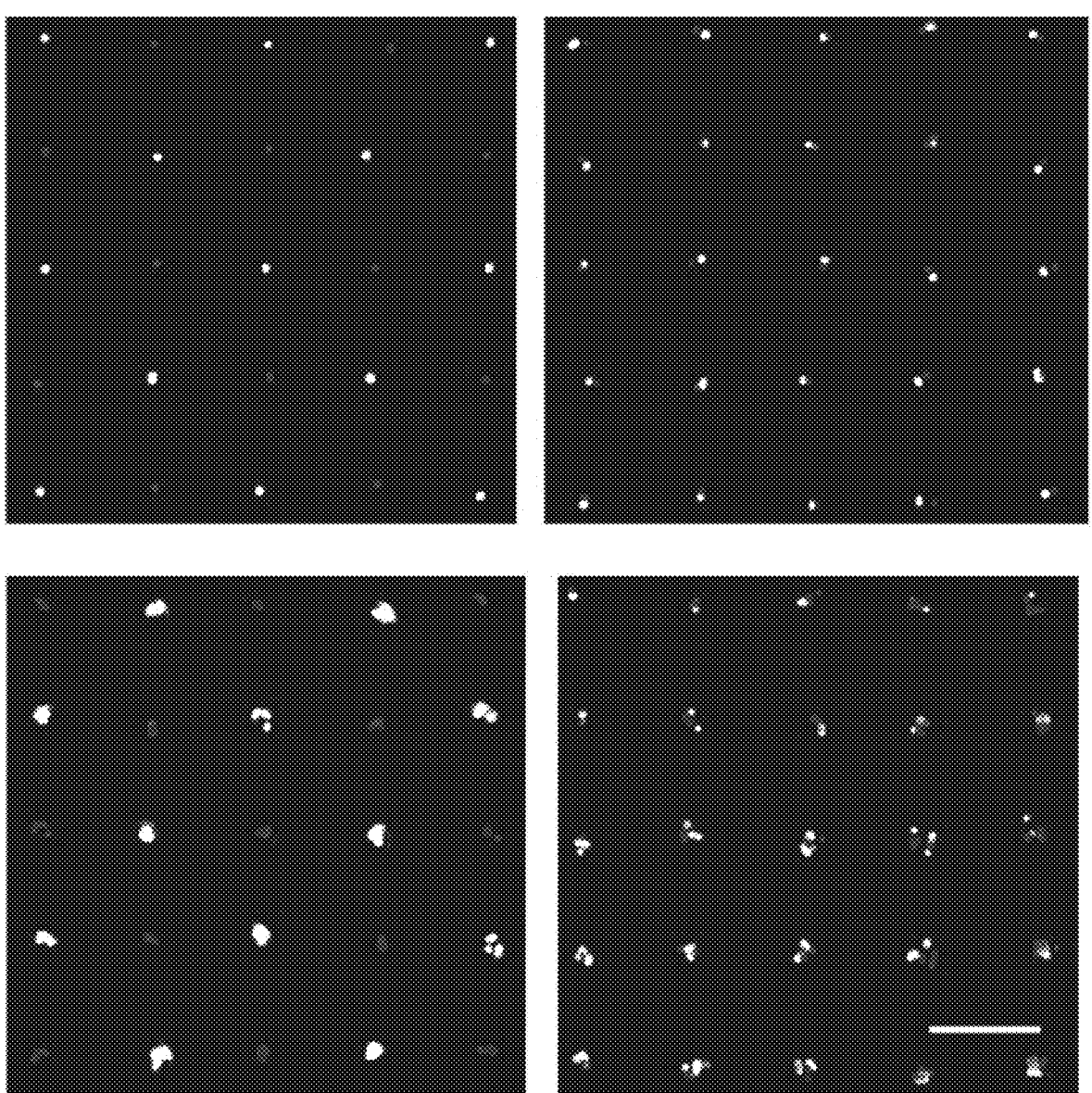
Figure 7C:
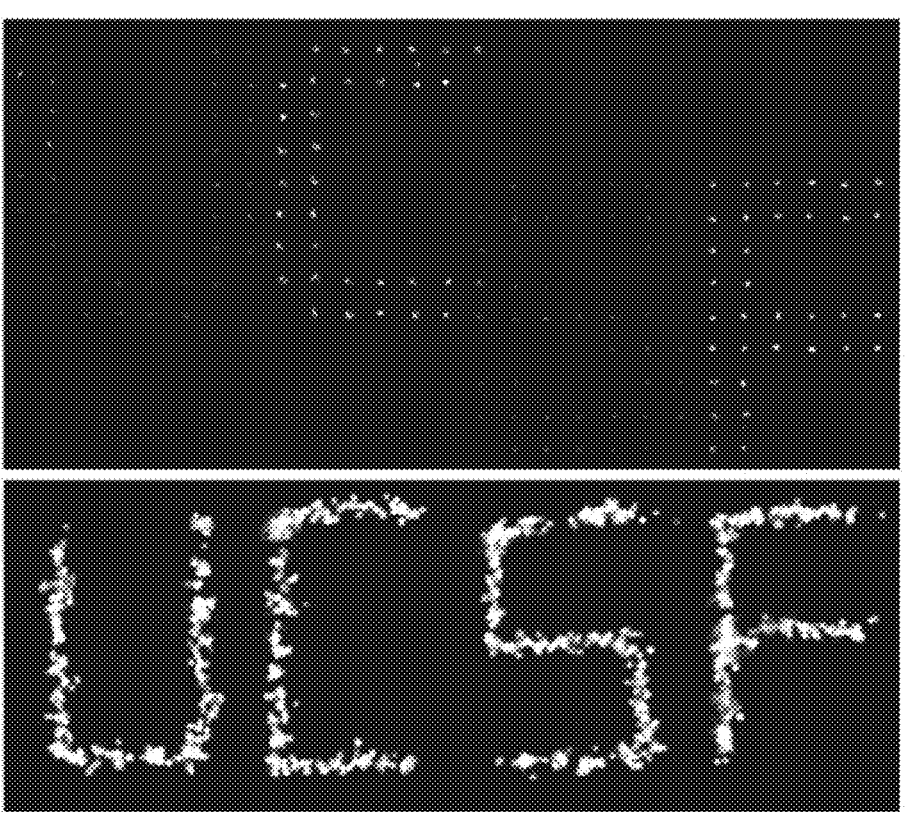
Figure 7D:
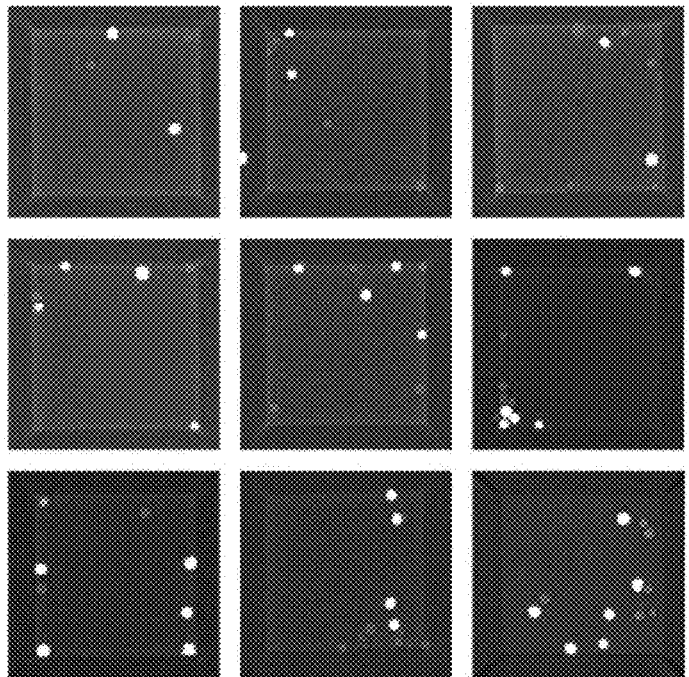
Figure 8A:
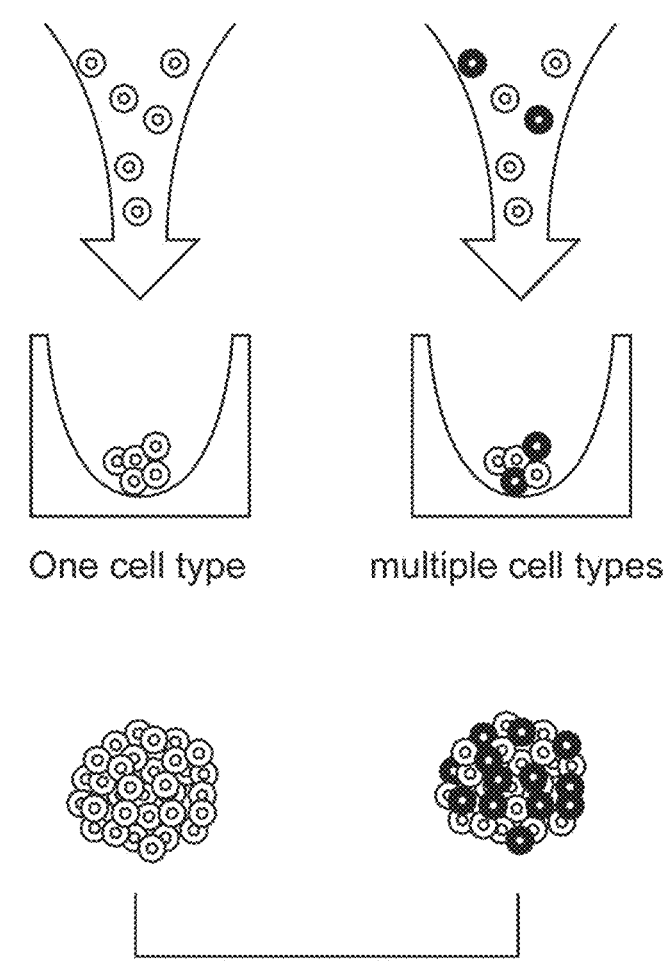
FIGS. 8A-8E, illustrates that the microfluidic device of this disclosure enables controllable formation of spheroids.
Figure 8B:
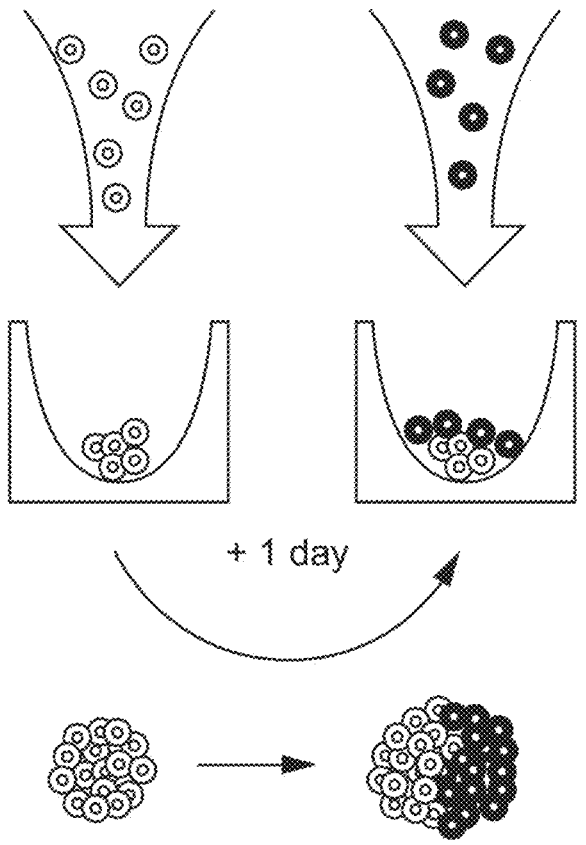
Figure 8C:
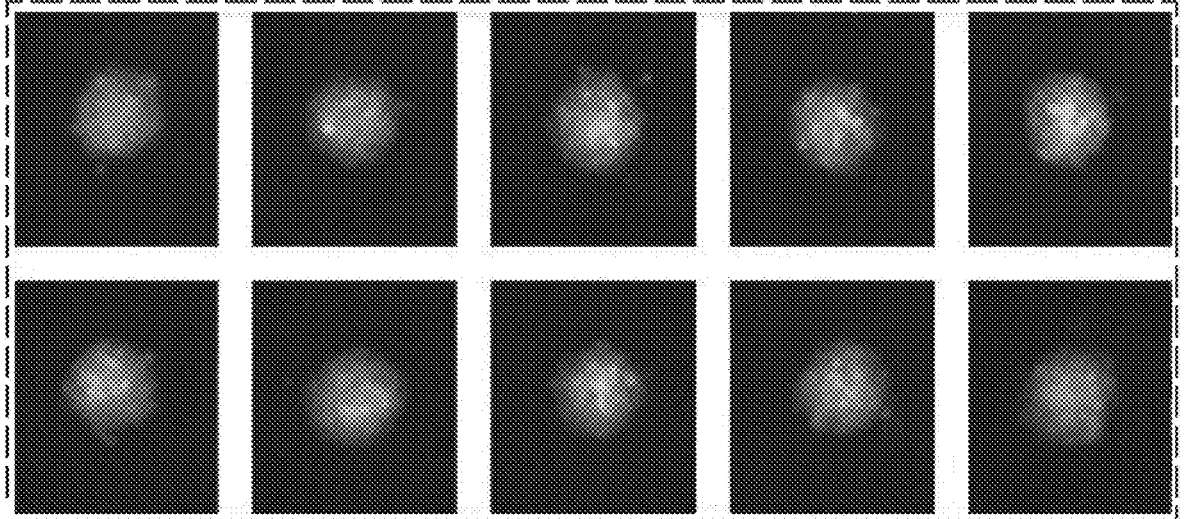
Figure 8D:
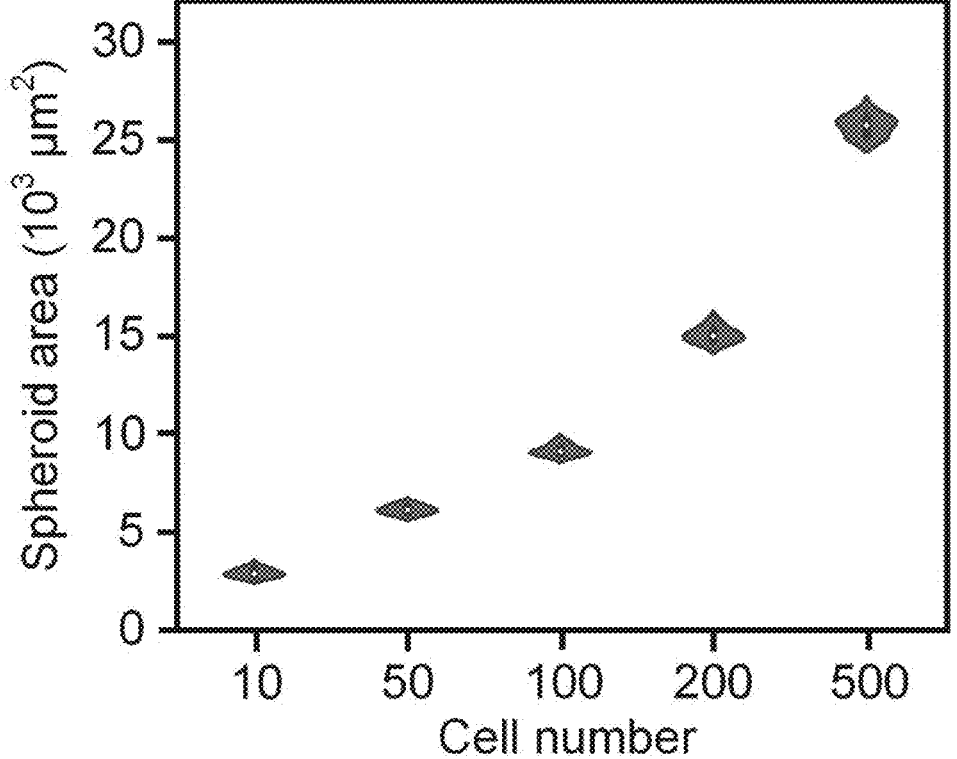
Figure 8E:
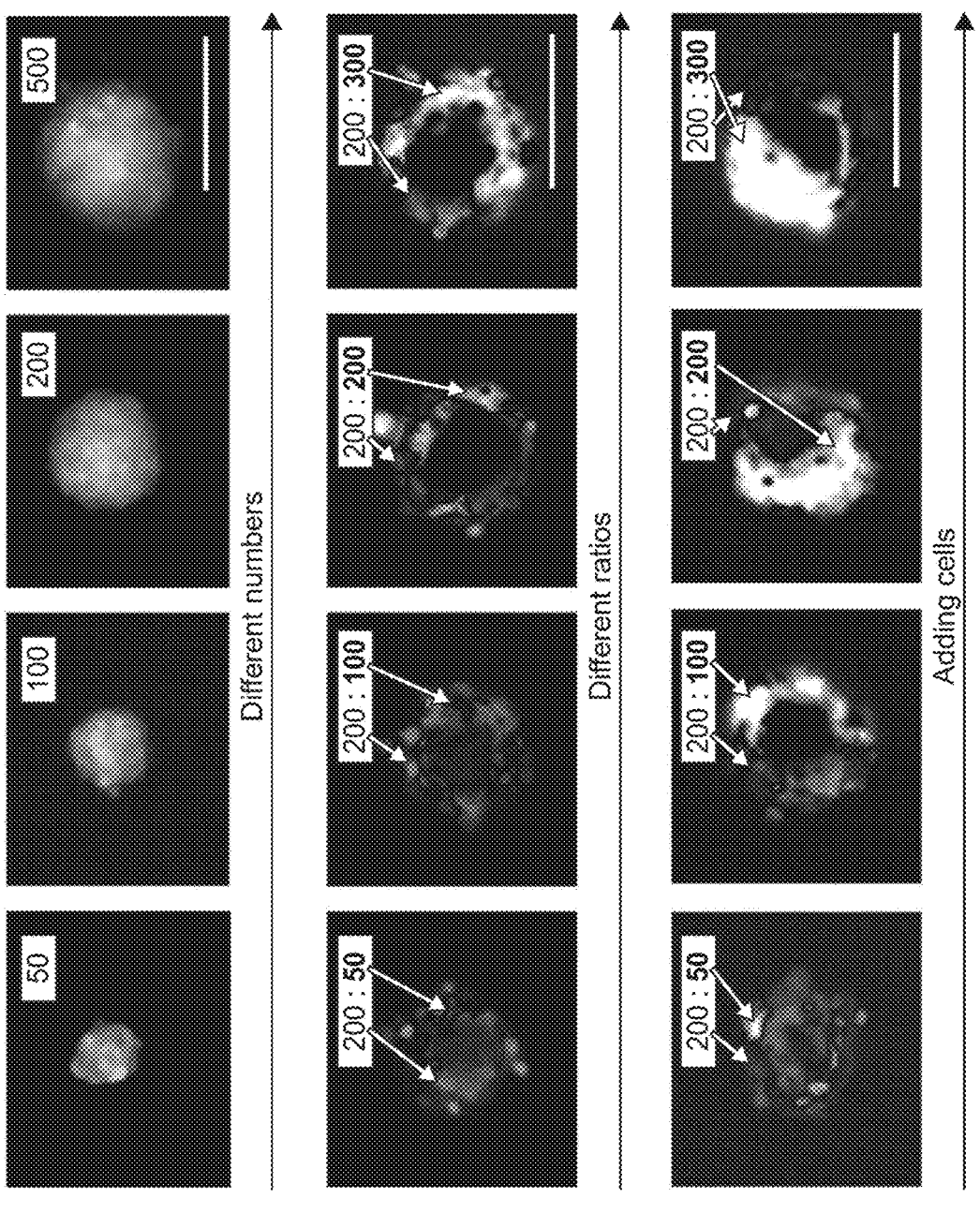
Figure 9:
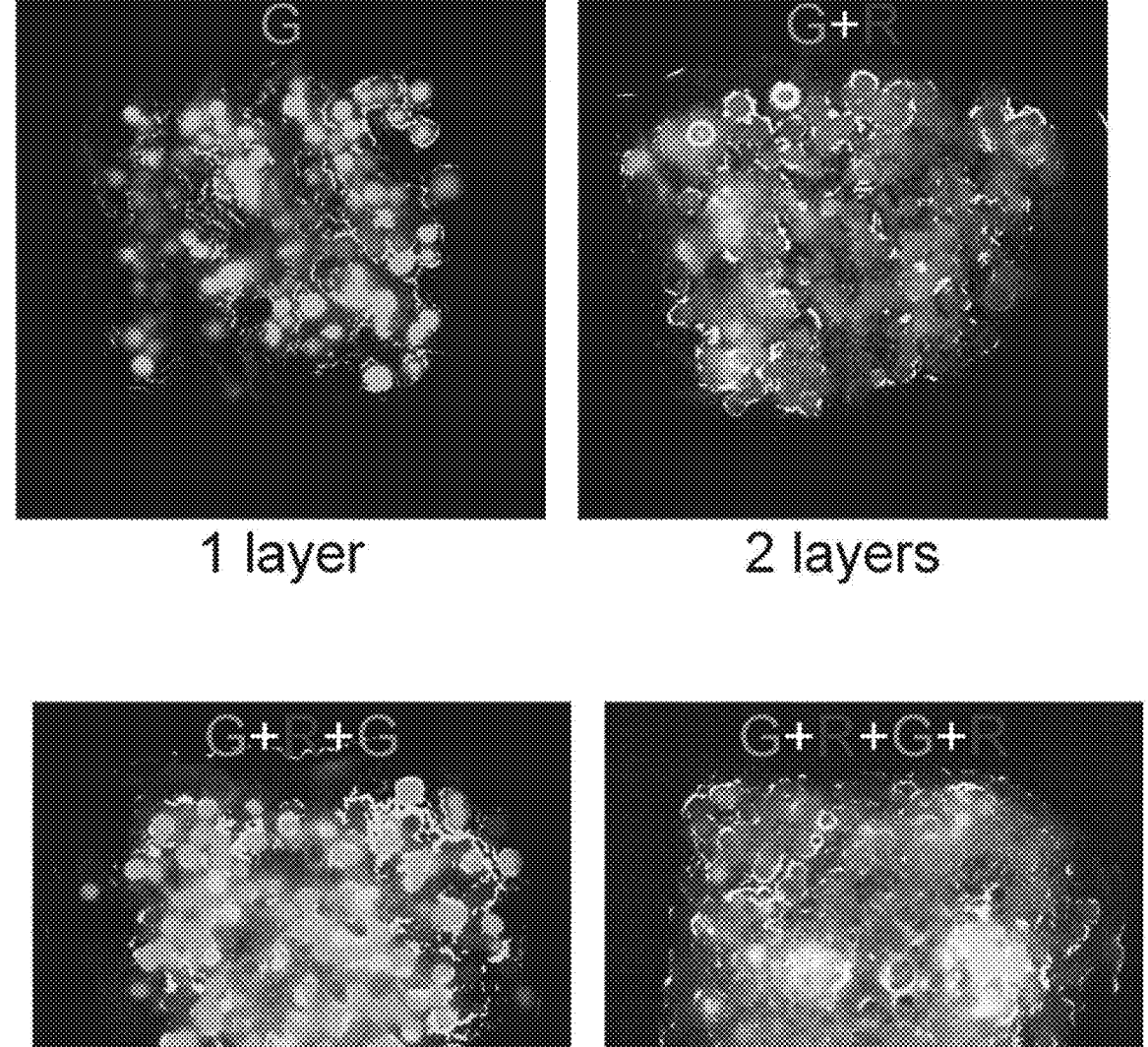
FIG. 9 shows the results of layer-by-layer printing of cells, wherein each cell is labelled as green or red. The first printed layer has green cells, the second layer has red cells, the third layer has green cells, and the fourth layer has red cells. The experiment shows that the cells can be successfully and selectively printed as different layers.
Figure 10:
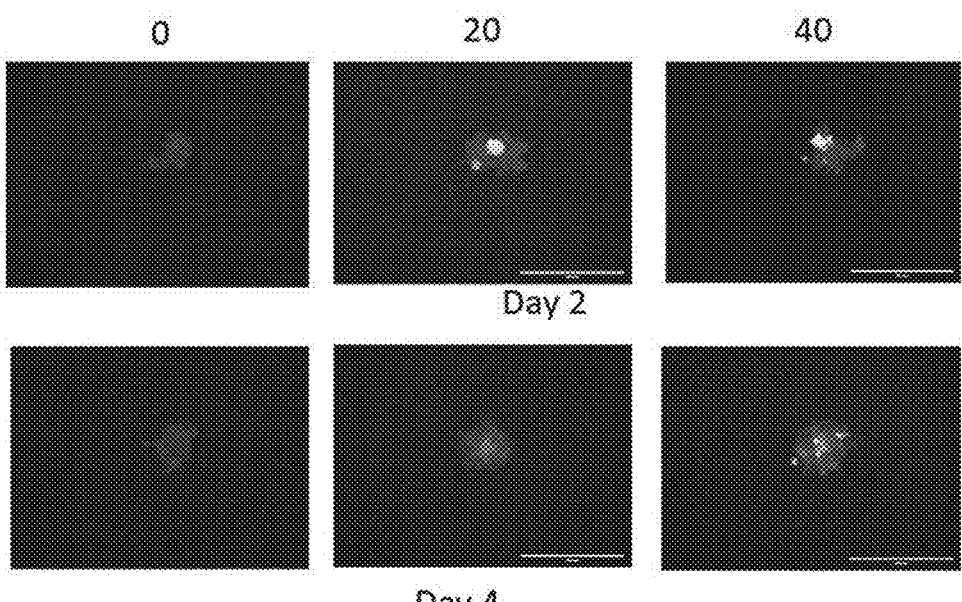
FIG. 10 shows the printing of spheroids with green 3T3 cells and red HepG2 cells, wherein each spheroid has about 100 HepG2 cells with different numbers of 3T3 cells varying from 0-100e. The experiment shows that each cell type can be printed to a desired location within the spheroid. In other words, the printing allowed for the construction of spheroids with different cells types, wherein each region of the spheroid can have the desired type of cell.
Figure 10:
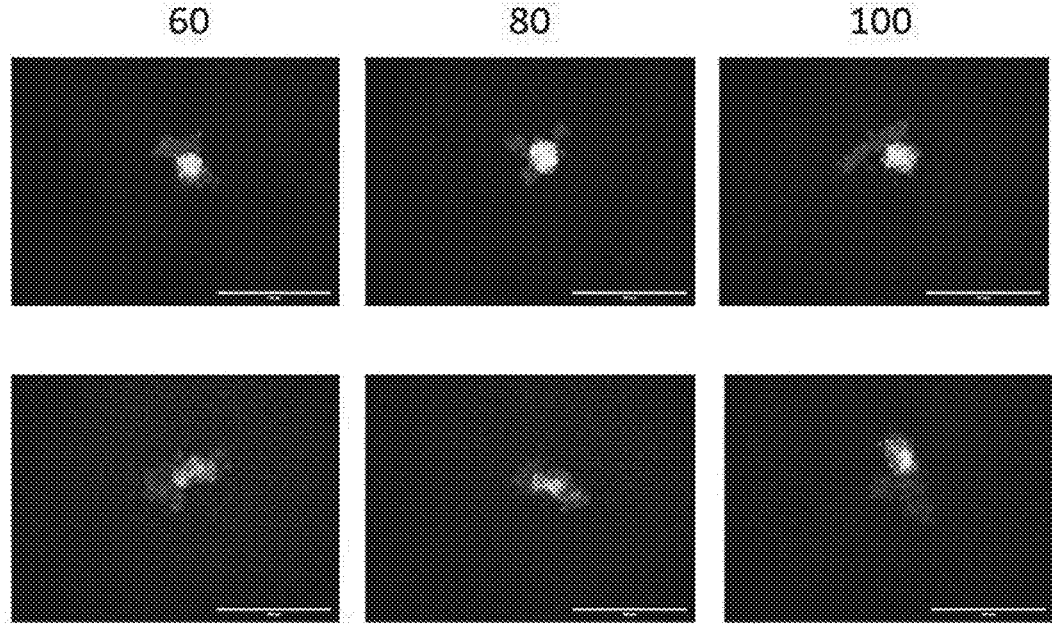
Figure 11:
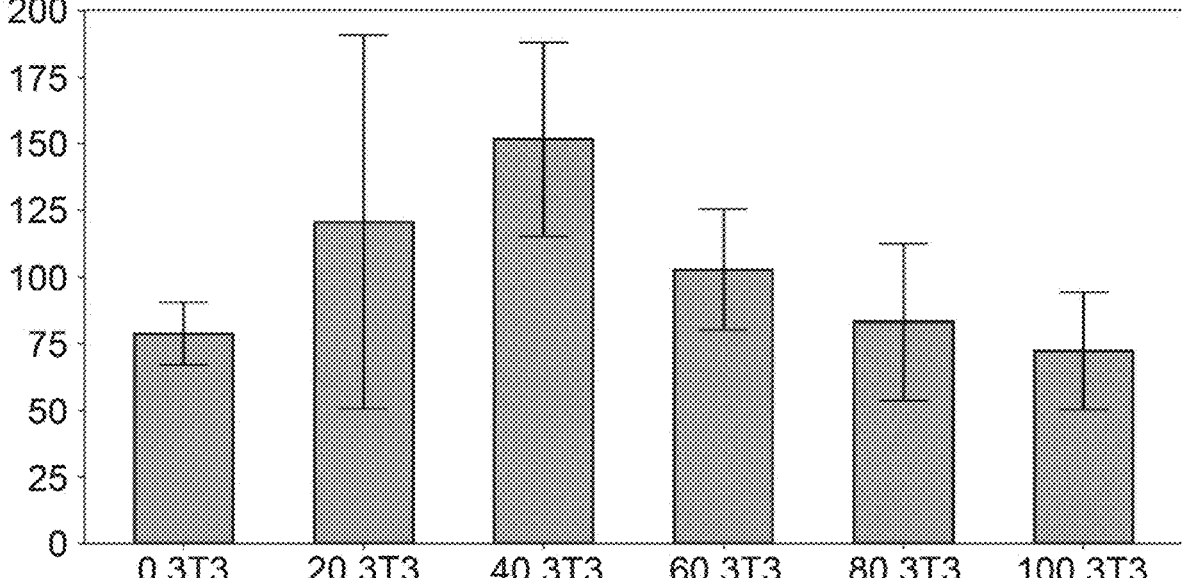
FIG. 11 shows how the number of NIH 3T3 cells in a multicellular spheroid influences the secretion of albumin from hepatocytes (HepG2). In particular, the highest secretion of albumin was observed with 40 3T3 cells, whereas secretion of albumin decreased with increasing deviation from 40 3T3 cells.
Figure 12:
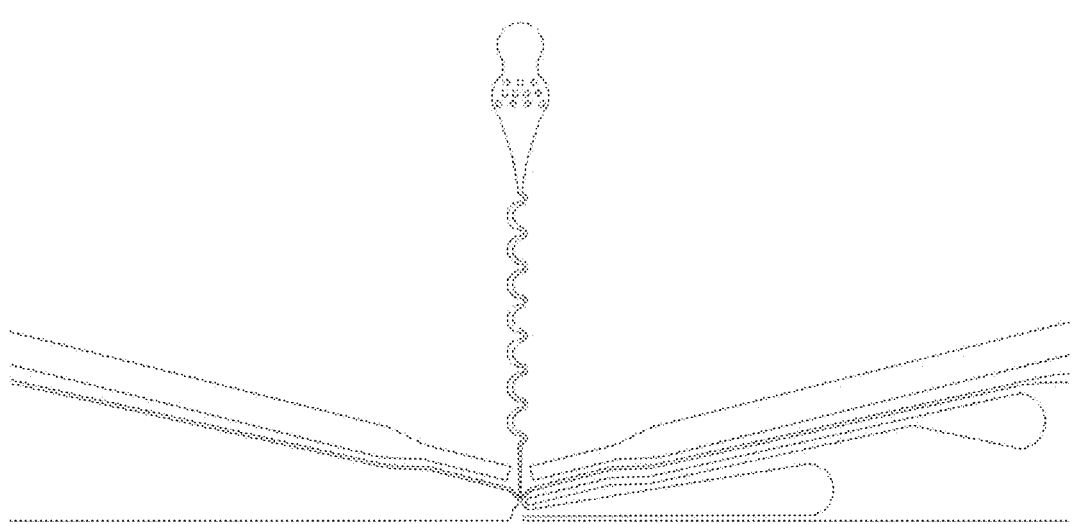
FIG. 12 shows a printhead with a compact design that can potentially achieve higher printing resolution, potentially due to its compact size. The white bar shows the scale of 1000 micrometers.
Figure 12:
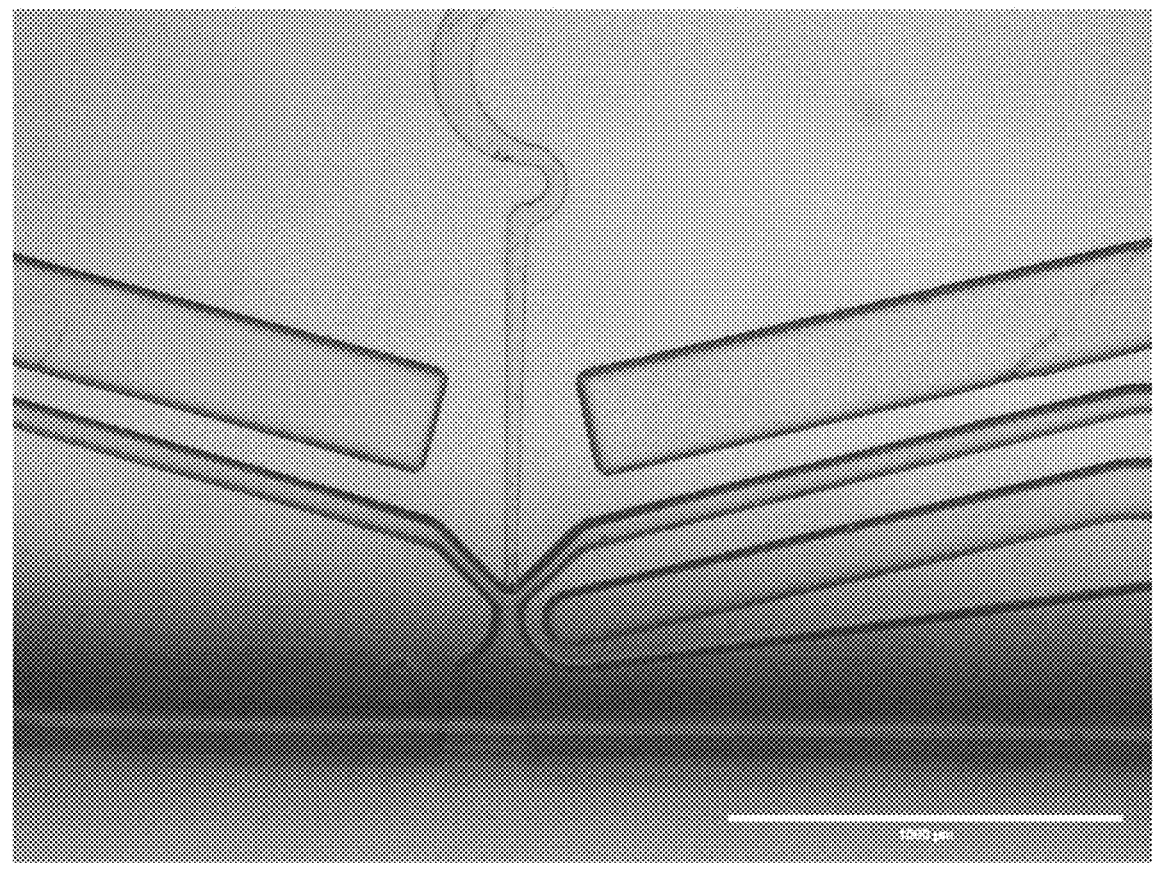

An embodiment of the subject systems, devices and methods is now described with reference to FIG. 2, Panel A, which illustrates a microfluidic system including a microfluidic device 200 including a sorter. As shown in FIG. 2, Panel A, a microfluidic device 200 is employed to detect discrete entities 201 in a liquid 203 by applying excitation energy to the discrete entities 201 and detecting emission energy in order to sort the discrete entities 201 using an electrode to deliver select discrete entities 208, e.g., droplets, to a delivery orifice 206, e.g., a delivery orifice 206 of a print head via an air liquid co-flow junction 205. The air liquid co-flow junction is connected to one or more air channels 204 through which air flow 202 can be applied and controlled. The microfluidic device depicted in FIG. 2, Panel A also includes a collection tube for collecting discrete entities 207 to be deposited into a waste reservoir. In some embodiments, when the electrode is turned on by application of a voltage, discrete entities 201 are sorted to be deposited on the substrate 208. In certain embodiments, when the electrode is turned on by application of a voltage, the discrete entities 207 are directed to the waste reservoir via the collection tube.

FIG. 2, Panel B, illustrates the air-liquid co-flow junction 202 of the microfluidic device used to detect and/or sort discrete entities 200. The discrete entities 200 are delivered via the flow channel through a liquid to the air-liquid co-flow junction 202, which is connected to the one or more air channels 201 directing air flow towards the air-liquid co-flowing junction 202. The discrete entities are directed via the air-liquid co-flow junction 202 towards the delivery orifice 203, where optical fibers are configured to apply excitation energy 204 to the discrete entities 200 and to collect the emission signal produced by application of excitation energy 205.

FIG. 2, Panel C, illustrates a photograph of an embodiment of the air-liquid co-flow junction 202 of the microfluidic device of the instant disclosure. The discrete entities 200 are delivered via the flow channel through a liquid 201 to the air-liquid co-flow junction 204, which is connected to the one or more air channels 203 directing air flow 202 towards the air-liquid co-flowing junction 204. The discrete entities are directed via the air-liquid co-flow junction 204 towards the delivery orifice 205, where optical fibers are configured to apply excitation energy 206 to the discrete entities 200 and to collect the emission signal produced by application of excitation energy 207.

In some embodiments, the disclosed methods may include moving one or more discrete entities through a device and/or affixing one or more discrete entities to a substrate and/or removing the discrete entities from the substrate by changing the buoyancy of the discrete entities and/or exerting one or more forces on one or more components, e.g., beads, of the discrete entities. Embodiments of the methods also include releasing one or more discrete entities, e.g., an affixed discrete entity, from a substrate by, for example, modulating, e.g., modulating by removing, one or more force affixing the entity to the substrate. In some instances, discrete entities are removed from a substrate by removing an electric field affixing them thereto.

To facilitate the above manipulations, the present disclosure provides, in some embodiments, a substrate which includes an array of individually controllable electrodes. Such substrates may be configured such that individual electrodes in the array can be selectively activated and deactivated, e.g., by applying or removing a voltage or current to the selected electrode. In this manner, a specific discrete entity affixed via a force applied by the electrode may be selectively released from a substrate surface, while unselected discrete entities remain affixed via application of the force. The electrodes of such an array may be embedded in a substrate material (e.g., a suitable polymer material), e.g., beneath a surface of the substrate to which the discrete entities are affixed via application of the force. A variety of suitable conductive materials are known in the art which may be utilized in connection with the disclosed electrode arrays, including various metals. Liquid electrodes as described previously herein may also be used for such an application.

Methods, devices and systems for sorting discrete entities to a substrate are now described. One embodiment of affixing a discrete entity, e.g., a droplet 401, generated in a microfluidic device 400, to a substrate by applying a force, e.g., a dielectrophoretic force, is shown in FIG. 4, Panels C and D. FIG. 4, Panels C and D show a droplet 401 flowing through a liquid 402 in a flow channel being ejected from a delivery orifice 405, via the air-liquid co-flow junction 404 that is connected to the air channels 403 to direct the air flow, prior to affixation to a substrate. The microfluidic device 400 of FIG. 4, Panels C and D also comprises an optical fiber configured to apply excitation energy 406 to the droplets 401 and an optical fiber configured to collect the signal produced by the application of excitation energy 407 to the droplets 401 passing through the delivery orifice 405 via the air-liquid co-flow junction 404. The microfluidic device 400 of FIG. 4, Panels C and D further comprises an electrode 408 that can direct droplets 401 upon application of a voltage based on detection of certain characteristics, such as emission energy produced upon application of excitation energy, to either deliver and affix them to a substrate or to direct them to a waste reservoir 410. In some embodiments, as illustrated by FIG. 4, Panel C, the droplets 409 is not sorted and is instead directed to a waste reservoir 410 upon application of a specific amount of voltage V at the electrode 408. In certain embodiments, as illustrated by FIG. 4, Panel D, the droplets 409 is sorted to be delivered and affixed to a substrate when the electrode 408 is turned off, that is when no voltage is applied to the electrode.

The subject methods also include methods of adding reagents to a discrete entity, e.g., a droplet, e.g., a droplet affixed to a substrate. Such methods may include delivering and/or affixing a first discrete entity to a substrate or a portion thereof, e.g., a substrate surface. The methods may also include delivering one or more other discrete entities, e.g., a second droplet, such as a discrete entity and/or including one or more reagents, to a location on the substrate which is the same location as the first discrete entity or a location adjacent or in proximity to that of the first discrete entity. The first and subsequent applied discrete entities may then be coalesced such that the contents, including, for example, one or more reagents, of the first and subsequent discrete entities are combined. In some embodiments, coalescence is spontaneous and in other embodiments, coalescing discrete entities includes applying a force, such as an electrical force, to one or more of the discrete entities.

Some embodiments of this disclosure also include methods of adding one or more reagent and/or components, such as one or more beads, to one or more discrete entities, e.g., droplets, by delivering one or more discrete entities via the air/liquid co-flow junction of a device to a surface of a substrate. The methods may also include positioning one or more of such discrete entities on the substrate surface and/or affixing the discrete entities to the substrate via a force. According to the subject methods, an air/liquid co-flow junction of a device operably connected, e.g., fluidically connected, to a reagent source, may then be inserted into one or more of the affixed discrete entities. Upon insertion, the air/liquid co-flow junction may be utilized to inject one or more reagents into the one or more discrete entities.

Embodiments of the methods may include modulating the environment of a discrete entity and thereby modulating the contents of the discrete entity, e.g., by adding and/or removing contents of the droplet. Such modulation may include modulating a temperature, pH, pressure, chemical composition, and/or radiation level of an environment of one or more discrete entities. Such modulation may also be of the immediate environment of one or more discrete entities, such as an emulsion in which the discrete entities are provided and/or one or more space, such as a conduit, channel, or container, within a microfluidic device. An immediate environment of a discrete entity which may be modulated may also include a fluid volume, such as a fluid flow, in which the discrete entity is provided. One or more discrete entities may also be stored in a modulated environment.

The methods of this disclosure may also include recovering all or a portion of one or more discrete entities which have been affixed to a substrate. For example, one or more materials, such as one or more solvents and/or reagents may be recovered from a droplet via, for example, extraction. Such a recovery may be conducted by contacting one or more affixed discrete entities with a portion of a device, such as a microfluidic orifice connected to a suction device for sucking one or more material, such as one or more solvent and/or reagent from one or more affixed discrete entity. A microfluidic orifice may be inserted into a discrete entity and/or placed in proximity to a discrete entity, e.g., placed at a distance from a discrete entity having an order of magnitude of a discrete entity or smaller, for performing recovery from the entity. Embodiments of the methods of recovery from a discrete entity may also include shearing, e.g., detaching, a discrete entity from a substrate surface by, e.g., increasing the buoyancy of one or more discrete entities. The buoyancy of a discrete entity can be increased by increasing the volume of the discrete entity by, for example, injecting aqueous fluid or non-aqueous fluid into the discrete entity.

In some embodiments, the methods may include concentrating one or more components, e.g., beads, present in a discrete entity at a location within a discrete entity. Such concentrated components or alternatively, portions of the discrete entity not containing the components, may then be selectively removed, e.g., removed by suction, from the discrete entity. One or more components removed from discrete entities may then be conveyed into one or more isolated containers.

In various aspects, substrates for use in connection with the disclosed methods include one or more channels filled with one or more conductive, e.g., electrically conductive, liquid or solid materials, e.g., an electrode material. In some embodiments, such substrates may also include an insulating sheet. In some embodiments, one or more channels are configured, e.g., patterned, to generate an electric field above a portion of a substrate, such as an insulating sheet, upon application of a voltage to the one or more channels. In some embodiments, such a voltage and a resulting electrical field or an aspect thereof, e.g., a dielectrophoretic force, is sufficient to affix one or more discrete entities to the substrate. In some embodiments, a substrate, or a portion thereof, includes one or more electrodes having a net charge which is opposite in polarity, e.g., negative or positive, relative to the polarity of one or more discrete entities, e.g., droplets, being affixed to the substrate.

In some embodiments, surfaces of substrates include one or more electrodes. In various embodiments, one or more electrodes are pre-formed on a substrate or portion thereof, e.g., a substrate surface. Substrates may, in various embodiments, be mounted upon and/or adjacently to, e.g., contacting, a stage, such as a movable stage, such as a stage movable in an X-Y and/or Z direction. In some embodiments, a stage is movable in a direction toward and/or or away from a microfluidic device, or a portion thereof, e.g., a delivery orifice 105. Also, in some embodiments, a microfluidic device 100, or a portion thereof, e.g., a delivery orifice 105 is movable in a direction toward and/or or away from another portion of a device, e.g., a stage, and/or a substrate 117. A stage and/or a microfluidic device 100, or a portion thereof, e.g., a delivery orifice 105, may be movable in constant movement or in increments on a scale of a diameter or radius of one or more discrete entities, e.g., 5 or less, 10 or less, 50 or less, or 100 or less discrete entities. A stage and/or a microfluidic device 100, or a portion thereof, may be movable in one or more direction, e.g., an X and/or Y and/or Z direction, in one or more increments having a distance of, for example, 1 μm to 1000 μm, inclusive, such as 1.0 μm to 750 μm, 10 μm to 500 μm, 1 μm to 50 μm, or 1 μm to 10 μm, inclusive. In some embodiments, the devices may me movable in constant movement or one or more increments on a scale to correspond with positions on a substrate 117 where discrete entities 101 may be attached, such as wells on a well plate including any of the well plates described herein.

In some embodiments, the methods include affixing one or more discrete entities 101 to a substrate 117, or a portion thereof, e.g., a surface, via wetting, e.g., electrowetting. In some embodiments, wetting includes moving, e.g., flowing, one or more discrete entities 101 from a delivery orifice 105, through a substrate fluid to a substrate surface of a substrate 117. In some embodiments, the wettability of a substrate is sufficient to attach one or more discrete entities 101 to the substrate 117 via, for example, wetting forces. In some embodiments, the methods include modifying, e.g., increasing or decreasing, the wettability of a substrate 117 so as to be sufficient to affix a discrete entity 101 to the substrate 117 via wetting forces. Various aspects of the methods may also include applying exogenous electromagnetic radiation in an amount sufficient to affix a discrete entity 101 to a specific location on a substrate 117.

In some embodiments, the subject methods include patterning one or more channels, e.g., channels of a substrate or aspects thereof, to provide a plurality of charged electrode features in a grid pattern. Droplets are affixed to the grid pattern using dielectrophoresis, which allows the application of forces to uncharged conductive droplets suspended in a nonconductive medium. The patterned substrate may be fabricated using standard microfluidics techniques. For example, a molded PDMS device may be placed with microfluidic channels facing up and bonded to a thin polymer film.

As illustrated in FIG. 1, affixing one or more discrete entities, e.g., discrete entities 101, to a substrate, e.g., a substrate 117, or a portion thereof, e.g., a surface, may include attaching the discrete entities to the substrate, e.g., substrate 117, via a force, such as a gravitational, electrical, and/or magnetic force. As such, in some embodiments, a delivery orifice, e.g., a delivery orifice 105, is positioned above a substrate 117. In some embodiments, the methods include applying an electrical voltage and/or current to electrodes, e.g., electrodes 109, positioned in or on the substrate, e.g., substrate 117. Affixing one or more discrete entities, e.g., discrete entities 101, to a substrate, e.g., a substrate 117, or a portion thereof, may also include affixing the entities to the substrate via interfacial tension.

Embodiments of the disclosed methods, for example the disclosed methods as described with reference to FIG. 1, may also include a step or steps of storing one or more discrete entities, e.g., one or more discrete entities 101 which are affixed to a substrate, e.g., a substrate 117, or a portion thereof, e.g., a surface. Methods of storing the discrete entities may include maintaining one or more affixed entities under controlled environmental conditions, e.g., at a fixed temperature and/or pressure, for a storage period. In some embodiments, one or more forces are applied and/or maintained to maintain the one or more affixed entities in an affixed state for the entire storage period.

In some embodiments of the disclosed methods, one or more microfluidic devices are integrated with an automated system which selectively positions one or more portions of the microfluidic devices, e.g., one or more air/liquid co-flow junctions and/or delivery orifices, relative to a substrate or a portion thereof, e.g., a substrate surface. Accordingly, in some embodiments the methods include selectively positioning, e.g., positioning at a particular location using an automated system, one or more one or more air/liquid co-flow junctions and/or delivery orifices relative to a substrate or a portion of a substrate to selectively deliver one or more discrete entities to one or more locations on or in proximity to the substrate or a portion thereof, e.g., a substrate surface. Automated systems as disclosed may include one or more control units, e.g., control units including a central processing unit, to control one or more aspects of applying discrete entities to a substrate, such as physical positioning of one or more one or more air/liquid co-flow junctions and/or delivery orifices and/or timing of discrete entity dispensing. Automated systems may be configured to position, e.g., position independently one or more one or more air/liquid co-flow junctions and/or delivery orifices with respect to a stationary substrate. Aspects of the subject methods may include delivering a first member of a plurality of discrete entities to a first location on or in proximity to a substrate or a portion thereof, e.g., a substrate surface, and a second member of the plurality of discrete entities to the first location or a second location on or in proximity to the substrate.

The subject methods may also include modulating, e.g., changing one or more aspect of, one or more force, e.g., by modulating an electric field and/or buoyancy of a discrete entity, to thereby move one or more discrete entities, e.g., a droplet, from a first affixed location on a substrate to another location. The methods may also include applying one or more additional, e.g., second, force which is sufficient to move one or more discrete entities from a first affixed location to a second location on a substrate and/or affix the one or more discrete entities at the second location. Aspects of the methods may also include applying a cross flow of fluid and/or exogenous electromagnetic radiation sufficient to move a discrete entity from a first location, e.g., a first affixed location, on a substrate to a second location on a substrate.

Embodiments of the subject methods may also include performing one or more assays, e.g., one or more biological assays, such as any of the assays described herein, on and/or in one or more of the discrete entities before and/or after delivery of a discrete entity to a substrate or a portion thereof, e.g., a substrate surface. In some embodiments, such substrates may include a well plate or a portion thereof. The term "well plate", is used broadly herein, to refer to a plate having one or more wells, e.g., divots or compartments, therein, such as a mictrotiter plate. However, as used herein, the term "well plate" may also refer to a patterned array of discrete entities, e.g., droplets, as described herein, which discrete entities are affixed to a substrate surface. In such embodiments, the substrate surface may include traditional wells, such as divots or compartments, but may alternatively be a flat surface.

Standard assays employ well plates having, for example, a 384 well format. However, well plates which may be prepared and/or utilized in accordance with the subject methods and devices, e.g., well plates including ordered arrays of discrete entities, may include well plates having, for example, from 20,000 to 500,000, inclusive, wells, such as from 50,000 to 150,000, inclusive, such as from 80,000 to 120,000, inclusive, such as 100,000 wells. In such a well plate, each well may have an area ranging, for example, from 0.01 mm$^2$ to 1 mm$^2$, inclusive, such as from 0.05 mm$^2$ to 0.5 mm$^2$, such as about 0.10 mm$^2$.

The methods described herein enable a significantly increased array density within a standard well plate footprint allowing for the performance of a significantly increased number of assays and/or experiments. Such methods allow, for example, the performance of assays on a number of samples that is significantly higher than is achievable in a set amount of time and/or using a set amount of space according to standard methods.

Aspects of the disclosed methods may also include controlling, e.g., maintaining, the temperature of one or more discrete entities before and/or after delivery of the one or more entities to a substrate or a portion thereof, e.g., a substrate surface. For example, in some embodiments, one or more discrete entities are thermalcycled before and/or after delivery to a substrate or a portion thereof, e.g., a substrate surface.

The subject methods may also include printing a structure, e.g., a three-dimensional structure, by employing a device, such as the device depicted generally in FIG. 1. In some embodiments, the methods include directing a first layer and/or a second layer and/or one or more additional layers, e.g., 3 to 1000 layers, inclusive, such as 10 to 500 or 50 to 100 layers, of discrete entities, e.g., droplets, to a substrate or a portion thereof, e.g., a substrate surface. In various embodiments, the discrete entities include one or more solid and/or gel materials, such as one or more polymers. Aspects of the disclosed methods may also include initiating and/or sustaining a reaction, e.g., a photopolymerization reaction, which causes discrete entities to solidify, e.g., solidify on a substrate to which the discrete entities are applied.

EXEMPLARY EMBODIMENTS

Exemplary, non-limiting embodiments of the present disclosure are provided below. While these are described with respect to droplets, droplet "printing", and related devices and systems, it should be understood that such embodiments may be equally applicable to the printing of non-droplet discrete entities as well.

In one embodiment of the present disclosure, droplets of different composition is "printed" to a substrate using a microfluidic print head, e.g., as described herein. The droplets are made ahead of time using a microfluidic or non-microfluidic technique, such as flow focusing or membrane emulsification, respectively. The pre-formed droplets are then introduced into the print head and sorted on demand according to their fluorescence. The droplet solutions are dyed with different solutions prior to being encapsulated as droplets so that, when injected into the print head, a detection technique, such as flow dropometry, can be used to identify each droplet's type and, using this information, a computer can determine which droplets to sort.

This allows dispensing of precise solutions to the substrate. Once dispensed by the print head, the droplets are affixed to the substrate using a force such as, for example, a dielectrophoretic force that is generated via electrodes fabricated under the substrate surface. In addition to dielectrophoresis, other forces can also be applied to affix the droplets. For example, an electrical force can be applied in which the substrate can be charged oppositely to the droplets, creating an electrical attraction. The droplets can be charged as they pass through the microfluidic print head using a channel comprising charged fluid that contacts the droplets or, for example, a salt water electrode as described herein. Other forces that can be used are, for example, gravitational force. Magnetic forces can be used in similar ways. Wetting and chemical forces can also be used such that the droplets, upon contacting the substrate, wet the surface and are adhered to it via surface tension.

In addition to droplets of different type labeled with detection components that make each type distinguishable, a "sorting on demand" microfluidic device for directing specific droplets to the substrate at controlled times, and a substrate constructed so as to maintain droplets at specific locations, a system which automates positioning of the substrate under the delivery orifice with the sorting on demand device helps provide for high-speed targeted dispensing of droplets. This can be accomplished using, for example, electrically-controlled microscope stages to position the substrate under the delivery orifice, and a computer to detect and sort droplets on demand and in registry with the substrate.

The droplet dispenser is, in essence, a highly miniaturized and extremely high throughput liquid handling robot and, as such, it is valuable for performing a variety of applications, particularly biological assays. For example, droplets comprising reagents, cells, and other components, can be dispensed to the substrate, subjected to changing environmental conditions, such as heating for incubation, and monitored over time to measure reaction activity. The results obtained from monitoring the system can be integrated together with the dispensing platform to, for example, change the conditions in specific droplets by adding additional reagents based on reaction progress.

In some embodiments of the present disclosure, the described system can be used to "print" cells and tissues. In such embodiments, the cells or tissue building blocks are first encapsulated in droplets labeled with detection components along with necessary biological reagents, such as matrigel or collagen. The resulting droplets, which can contain cells of different types, cell aggregates, or biological reagents without cells, can then be sorted on demand via the print head and dispensed to the substrate, where they are affixed with a force. To localize cells on the array, traps can be positioned with space between them. To print tissues, the cells are preferably deposited sufficiently close so as to allow neighboring droplets to coalesce and the cells contained within them to interact with one another. This can be used, for example, to print a "red" cell next to a "green" cell next to a "blue" cell. These steps can be repeated to make a line of cells in a desired pattern. Additional lines can then be printed adjacent to the first line to print a flat layer of cells. Additional layers can then be printed above the first layer, to generate a 3D multi-layered "tissue". With proper selection or engineering of the cells, once the tissue is printed, the cells can interact with one another to further modify the structure. Additional droplets can be added to modulate the structures development, such as biological reagents or drugs.

In similar embodiments, cell aggregates of defined type can be localized on the array in separate droplets. For example, a first position on the array can be dispensed with a specific combination of cells, such as a red, then a green, and then a blue cell. These cells will be dispensed into the same droplet by droplet addition in which they can then interact to perform functions. This can be repeated at additional spots on the array to build multiple identical aggregates or different, defined aggregates. This can be used, for example, to build elementary tissue structures composed of just tens of thousands of cells, or to study interactions between different cell types such as bacterial and mammalian cells, or microbes with infecting virus. Drugs and other chemical and biological compounds can also be added to the droplets, for example, to study how to modulate the interactions between the organisms.

In some embodiments, cell-free experiments can be performed in the arrayed droplets. For example, cell-free extracts such as transcription and translation machinery can be encapsulated in the droplets, along with other components, including, if desired, cells. These can then be incubated on the array and monitored over time, as described above, to track progress of the reaction. This can be used, for instance, to screen pathways for activity in cell-free extracts and to investigate how pathway activity is modulated with changing conditions, such as the application of heat or presence of different inducers, inhibitors, etc.

Synthetic biology screening: The methods described herein can be used to perform screens for synthetic biology applications such as, for example, screening cells or cell-free extracts engineered to express biological pathways that produce molecules. By isolating the pathways in droplets on the array and tracking the production of the molecules using methods like microscopy, spectroscopy, it is possible to test different pathway sequences for desired activity.

3D printing with materials: In another embodiment of the disclosed methods, discrete materials comprising solids, liquids, or solidifiable materials can be printed to the substrate, to generate planar or "3D" structures. For example, solid particles can be generated using a variety of processes, such as emulsion polymerization or droplet-based templating in which the material is emulsified into droplets while liquid and then solidified to convert a liquid droplet into a solid particle of similar dimensions. An "ink" comprising these solid particles can be generated by mixing together multiple particles of different type with different labels that can be determined optically. The particle-based ink can then be introduced into the print head and sorted on demand to the substrate, thereby depositing solid particles to the substrate in the desired pattern. Trapping forces like electrostatic or magnetic forces can also be used to localize the particles at defined positions. A first layer of particles can be deposited, and afterwards, additional layers can be added, to generate 3D structures in which the composition of each particle in the structure is defined exactly. Once deposited, a variety of methods can be used to bond the particles together such as, for example, chemical bonding techniques or sintering of the particles. In a slightly different embodiment, the aforementioned "3D printer" can print liquid droplets that can be solidified after being dispensed using, for example, chemical cross linking, polymerization, or gelation. The materials that are printed can comprise hydrophilic or hydrophobic liquids, metals, and plastics, and forces being selected as needed to enable controlled sorting on demand and dispensing of the materials to the substrate.

Sorting on demand: In microfluidic and other applications it is often desirable to generate droplets of defined type on demand. One method for accomplishing this is using a microfluidic droplet generator controlled by a membrane valve. When the valve is closed, the dispersed phase does not flow and no droplets are generated. When it is opened, it flows and droplets are generated. This approach can generate droplets on demand as fast as the valve can opened and closed, which is often no faster than 100 Hz. In addition, the droplets are all formed of the same fluid; to enable generation of droplets on demand from multiple fluids, multiple devices, each with its own fluid, may be interfaced together; this is challenging for more than a handful of fluids. Such a challenge may be addressed by embodiments of the present disclosure wherein droplets are generated on demand by sorting them, from a preexisting emulsion, on demand. The droplets of the different desired fluids are first emulsified separately and combined into a single mixed emulsion. They are labeled to enable them to be differentiated from one another using optical detection, such as flow cytometry. This combined emulsion is then injected into a microfluidic device comprising the sorter which scans the droplets and sorts them to be delivered to the substrate or directs them to the waste reservoir. The emulsion that is sent into the waste reservoir can be recycled through the sorter, to conserve reagents. The value of this droplet on demand technique is that it is limited in speed to the rate at which the droplets can be sorted. In addition, the combined emulsion can contain droplets of many different types, not just tens of droplets but hundreds or thousands of droplets. This allows sequences of droplets of unprecedented complexity to be generated, which is important in connection with the described printing technology for allowing controlled dispensing and combining of different reagents at each substrate location. The speed of the droplet sorter will allow sorting of emulsions with unprecedented numbers of droplets. This will be valuable for applications in protein engineering and cell biology, in which the target droplets or cells are extremely rare in the population. Such enrichment is important, for example, for enhancing enzymes through droplet-based microfluidic directed evolution or for isolating very rare circulating tumor cells from blood cells.

The sorting on demand device provides the control which facilitates dispensing defined sequences of droplets, but the trapping substrate allows for the capture those droplets at specific locations so that one or more assays of interest can be performed on them. There are a variety of substrates that can be constructed for trapping the droplets. One such substrate uses dielectrophoresis to trap the droplets. To generate the dielectrophoretic traps, the substrate may be fabricated so as to contain electrodes with which to generate the requisite electric fields. This can be accomplished by patterning electrodes under a dielectric sheet; the electrodes can be energized with positive and negative charges to generate large electric fields with a spatial gradient; when droplets are dispensed above the substrate and in the region of the field, dielectrophoretic forces will cause them to be attracted to the substrate, and adhere. The electrodes can be patterned using conventional fabrication techniques, such as metal sputtering or deposition on the sheet, or by fabricating microfluidic channels that can be bonded face-side-up to the bottom side of the sheet such that the channels are below the sheet and not in fluidic communication with the fluids above the sheet. The channels can then be filled with conductive medium, such as solder or electrolyte solution and charged to generate the desired electric fields for dielectrophoretic droplet tapping. By modulating the shapes, widths, and heights of the microfluidic channels, it is possible to structure the electrodes, thereby providing control over the fields that are applied to the droplets above the sheet.

Affixing droplets: In some embodiments, it is desirable to affix liquid or solid entities to the surface of a substrate via application of a force. One such force that can be used is dielectrophoresis, in which a patterned array of electrodes under the dielectric substrate is used to generate electric fields that dielectrophoretically attract or repel the entities, trapping them at the desired locations.

Non-dielectrophoretic electrical forces can also be used. In such embodiments, the entities can be charged with, for example, a positive charge, either before, during, or after their flow through the print head. The substrate can then be charged oppositely, creating an electrical attraction between the entities and the substrate that will affix them. The polarity of the entities and substrate can also be modulated to generate a repulsive force allowing, for example, droplets to be ejected from the substrate. Electrodes can be used for these purposes. For example, the substrate can be uniformly charged with one polarity so that droplets of the opposite polarity will stick to the substrate. Provided a dielectric separates the electrode from the droplets, no charge will flow between the two and the force will remain; alternatively, if the two are allowed to come into electrical contact, then charge will flow, removing the force but allowing, for example, a droplet to wet to the electrode and be affixed by interfacial tension forces.

In another embodiment, the electrodes can be patterned so that each trap has a single or multiple electrodes with the same or different polarity and charge. This can be used, for example, to generate dielectrophoretic traps appropriate to affix single droplets. Each electrode can be addressable and a large array of the traps can be fabricated into the substrate, allowing each drop to be switched on or off as desired. This can be used, for example, to capture droplets to specific traps by modulating the strength of the field of the trap where the droplet is to be affixed relative to other traps in the vicinity. The traps can also be turned off, to selectively release drops.

Different affixing forces are also possible, such as wettability and interfacial tension forces. In such embodiments, the substrate can be patterned with regions that alternate between hydrophilic and hydrophobic. For example, the substrate can be natively hydrophobic but patterned with small islands large enough to accommodate one or multiple drops with hydrophilic wettability. The wettability patterning can be accomplished with, for example, spatially-modulated light-based polymer grafting or flow patterning of polyelectrolyte layers. Once the droplets are in contact with the hydrophilic patch, they may wet spontaneously or they may be induced to wet, for instance if surfactants are present, by applying a small, transient or long-lived electric field. Once wetted to the substrate, the droplets can be maintained for periods of time.

A method to trap droplets, which utilizes interfacial tension, may be accomplished with patterned features. For example, wells can be fabricated into the substrate and sized and/or shaped such that droplets fit therein and sit within the wells. The droplets can also be dispensed within a concave feature with a narrow opening, or between posts with narrow gaps. Such droplets may be held in place due to their interfacial tension and preference for remaining spherical.

Other kinds of electromagnetic traps can be generated using, for example, laser tweezers. Using an array of lasers directed at controlled locations on the substrate, droplets dispensed near the lasers may experience a force attracting or repelling them to or from the lasers, again generating a series of traps that can be used to localize the droplets. Magnetic droplets or particles can be affixed using magnetic or electromagnetic forces such as, for example, with ferrofluids, permanent magnets, paramagnetism, or electromagnetism generated by flowing electric current through an electrode patterned under the substrate.

Modulating the position of droplets: Once droplets are dispensed to the substrate, it is possible to change the position of the droplets on the substrate. This can be accomplished, e.g., magnetically, by modulating the magnetic field, electrically or dielectrophoretically, by modulating electric fields, via electrowetting on dielectric, or by varying the position of optical traps with the lasers, among other forces.

Adding reagents to droplets: In some embodiments, it may be desirable to dispense multiple droplets or discrete entities to a single location on the substrate array. This is valuable, for example, for adding different reagents to localized droplets at different and defined times. This can be accomplished by, for example, dispensing a first droplet to the array and then dispensing a second droplet to the same position as the first droplet. In certain embodiments, such as when electric fields are used to trap the drops, the electric fields generated by the substrate are sufficient to induce the droplets to merge, thereby combining their contents. The contents of the droplets can be mixed via diffusion or convective flow in the droplets generated. In other instances, droplets will merge spontaneously, such as when no surfactants are used. In other instances, merger can be induced via application of a laser or localized heating. Additional drops can be added to the same location to add, one, two, three, or more droplets to the same position. Using the droplet or sorting on demand techniques, the drops that are added and the sequence in which they are added can be controlled exactly. In another embodiment, a nozzle or capillary can be introduced into the affixed droplet to inject the desired reagent.

Recovering droplets or material therefrom: In certain applications, it is desirable to recover all or portions of the affixed droplets. This can be accomplished, for example, by bringing a nozzle close to the affixed droplet and drawing fluid into the nozzle, thereby drawing the droplet into the nozzle. If the nozzle shape is designed appropriately and the fluid flow adequate, it is also possible to recover a portion of the droplet in a mechanism similar to microcapillary-based droplet generation. Alternatively, or in addition, droplets can be removed from the substrate by adding additional liquid to them to increase their buoyancy; once the buoyant force is larger than the affixing force, the droplet will detach from the substrate and float away. In embodiments in which the traps can be selectively switched on and off, droplets can also be recovered by switching off the force and using buoyancy or flow to remove them from the substrate and recover them into a collection container.

Concentrating materials in droplets: In some embodiments, it is desirable to concentrate reagents or other materials in the droplets. This can be accomplished using available techniques for concentrating reagents such as, for example, placing beads in the droplets that can bind certain components in the droplets, and then either removing the bead or the portion of the droplet that does not contain the bead to achieve a concentration increase.

Secondary manipulation of droplets: The portions or complete droplets recovered with any of the methods described herein can then be dispensed into a secondary container by flowing them from the array into the container. For example, using the section method, individual droplets or droplet portions can be recovered from the droplet array and these portions flowed through a tube into a well on a well plate, where they are dispensed. This can be done one droplet at a time, dispensing each droplet into a separate well and thereby preserving the isolation of the droplets from one another. Once in the well, other operations can be perfumed on the droplet, such as propagating cells contained therein or performing biological reactions, such as ELISA, PCR, etc.

Manipulating affixed droplets: Affixed droplets can be manipulated using a variety of techniques to modulate their environment. For example, in some embodiments, it is possible to modulate the chemical, temperature, or pressure environment of the droplets to perform, for example, PCR by thermocycling the droplets. These kinds of environmental manipulations can be used to prepare the droplets for longer-term storage, such as at low temperature, to preserve reagents within them.

Alternatively, or in addition, the substrate can be fabricated to have a semi-permeable membrane that allows chemical communication with the droplets from below the substrate (or above depending on the orientation of the substrate relative to the droplets). By modulating the fluids under the membrane, chemical partitioning can be used to modulate the contents of the droplets while still preserving the droplets intact. For example, this can be used to change the buffering properties of the droplets by dispensing the droplets with a first buffer, e.g., containing ions, and then using the membrane, placing the droplets in chemical communication with another buffer with different ions, allowing the ions in the droplets to be replaced with those from the new buffer solution. By controlling the permeability of the membrane, the types of compounds that are modulated can be controlled based on, for example, their size, hydrophobic, charge, or chemical properties.

Parallel print heads: A single print head is limited in the rate at which it can dispense droplets to the substrate. One technique for dispensing droplets more quickly is to parallelize the print heads. In this approach, multiple delivery orifices and/or air liquid co-flow junctions can be attached to a single droplet on demand device and/or sorter on demand device so that, when a droplet is triggered, it is split into multiple portions, each of which is dispensed to the substrate at a different, defined location. This can also be used to dispense groups of droplets that were known to originate from the same parent droplet, and are thus related in certain ways. Due to the modular nature of the print heads, it is also possible to assemble multiple print heads together into a single device. For example, the use of the fiber optics for the detection of the droplets allows the detection optics to be localized to a small region in the device, while the sorting or droplet on demand devices, themselves, are only hundreds of microns in total size. This allows multiple devices to be assembled on a single chip so as to dispense droplets out of a single combined delivery orifice, or multiple delivery orifices and/or air liquid co-flow junctions. In theory, this should allow printing at rates increased by a factor equal to the number of devices assembled on the print head.

Multiple fibers for detection: To analyze the fluorescence of a droplet, it is necessary to provide excitation light, e.g., in the form of a laser, and read the generated optical fiber configured to collect a signal produced by the application of excitation energy. In some embodiments of the invention, this can be accomplished using a single optical fiber that serves both to funnel the excitation light into the device and also collects the emitted light in the reverse direction. A drawback of this approach, however, is that the optical properties that are ideal for excitation light guidance may not be the same as for optical fiber configured to collect a signal produced by the application of excitation energy capture. For example, to excite a narrow beam, a fiber with a narrow tip is preferred, but to collect the largest number of emitted photons, a wide fiber with a large collecting cone angle is preferred. In these instances, multiple fibers can be used. For example, a narrow fiber can be used to provide a concentrated, excitation signal, while a wide fiber can collect the emitted fluorescent light.

Synthesizing polymers: The ability to deliver droplets of defined composition to specific locations on a substrate is valuable for polymer synthesis. For example, in one embodiment, a first droplet can be dispensed to the substrate surface which includes a first monomer or polymer. A second droplet can then be dispensed to the same or an adjacent location, which includes a second monomer or polymer. The first and second droplets can then be incubated under and/or exposed to conditions sufficient for the contents of the first and second droplets to come into contact and for the first polymer or first monomer to form a covalent bond with the second polymer or second monomer, thereby generating a synthesized polymer. These steps can be repeated to increase the length of the polymer and thereby create polymers of defined sequence. In alternative embodiments, techniques like Gibson Assembly can be used for nucleic acid synthesis, which allows for the assembly of multiple components added at the same time, where overlap sequences are used to control the order in which the pieces are linked to synthesize a polymer of defined sequence. This can be used, for example to build DNA constructs for synthetic biology applications.

Screening libraries: Droplet based microfluidic techniques are valuable for screening libraries of compounds, enzymes, cells, etc., in which (or in connection with which) a reaction occurs that, normally, cannot be confined. For example, in directed evolution of enzymes, the product of a successful enzymatic reaction is a molecule that, generally, diffuses away from the enzyme catalyst. If many enzymes of varying catalytic power exist within the same solution, the product molecules mix, preventing the molecules produced by the action of one enzyme from being identified as having been produced by that enzyme. To evolve an enzyme, it is important to be able to select the best variant in a population (or a variant having a desired enzymatic activity relative to the other members of the population), which requires a method for measuring enzyme activity through product concentration. By enclosing each enzyme in a different droplet, it is possible to measure the activity of each variant independently by measuring the product concentration in each droplet. This can also be performed in the printed droplet format. For example, each enzyme variant can be localized in a droplet on the array and assayed for activity, and efficient enzymes (or those having a desired enzymatic activity) can be obtained by recovering the encapsulating droplets. Similar screens can be performed to test for therapeutic efficacy of a drug, e.g., a small molecule drug, or drug combination by evaluating its effects on cells in the droplets. Alternatively, by observing the droplets over time, it is also possible to screen based on time-dependent measurements, such as a peak production in product concentration at a specific time and/or for a specific duration.

Printing microarrays: In some embodiments, the methods, devices, and/or systems described herein can be used to synthesis oligos on an array for microarray production. For example, the substrate can be functionalized with a moiety to which nucleic acids can be attached. Then, by sequentially dispensing droplets of specific nucleic acids to individual spots on the substrate surface, the sequences can be attached to the substrate. The resolution of the spots will depend on the resolution with which the droplets can be printed, which is the on the order of micro to nanoscale features.

Types of Discrete Entities

The composition and nature of the discrete entities, e.g., microdroplets, prepared and or utilized in connection with the disclosed methods may vary. For example, in some embodiments, a discrete entity may include one cell and not more than once cell. In other embodiments, a discrete entity may include a plurality of cells, i.e., two or more cells. In some aspects, discrete entities according to the present disclosure may include a nucleic acid or a plurality of nucleic acids. In some embodiments, as discussed above, discrete entities may include one or more solid and/or gel materials, such as one or more polymers.

In some embodiments, a surfactant may be used to stabilize the discrete entities, e.g., microdroplets. Accordingly, a microdroplet may involve a surfactant stabilized emulsion. Any convenient surfactant that allows for the desired reactions to be performed in the discrete entities, e.g., microdroplets, may be used. In other aspects, a discrete entity, e.g., a microdroplet, is not stabilized by surfactants or particles.

The surfactant used depends on a number of factors such as the oil and aqueous phases (or other suitable immiscible phases, e.g., any suitable hydrophobic and hydrophilic phases) used for the emulsions. In selecting a surfactant, desirable properties that may be considered in choosing the surfactant may include one or more of the following: (1) the surfactant has low viscosity; (2) the surfactant is immiscible with the polymer used to construct the device, and thus it doesn't swell the device; (3) biocompatibility; (4) the assay reagents are not soluble in the surfactant; (5) the surfactant exhibits favorable gas solubility, in that it allows gases to come in and out; (6) the surfactant has a boiling point higher than the temperature used for PCR (e.g., 95° C.); (7) the emulsion stability; (8) that the surfactant stabilizes drops of the desired size; (9) that the surfactant has limited fluorescence properties; and (11) that the surfactant remains soluble over a range of temperatures.

Other surfactants can also be envisioned, including ionic surfactants. Other additives can also be included in the oil to stabilize the discrete entities, e.g., microdroplets, including polymers that increase discrete entity, e.g., droplet, stability at temperatures above 35° C.

The discrete entities, e.g., microdroplets, described herein may be prepared as emulsions. The nature of the microfluidic channel (or a coating thereon), e.g., hydrophilic or hydrophobic, may be selected so as to be compatible with the type of emulsion being utilized at a particular point in a microfluidic work flow.

Emulsions may be generated using microfluidic devices as described in greater detail below. Microfluidic devices can form emulsions consisting of droplets that are extremely uniform in size. The microdroplet generation process may be accomplished by pumping two immiscible fluids, such as oil and water, into a junction. The junction shape, fluid properties (viscosity, interfacial tension, etc.), and flow rates influence the properties of the microdroplets generated but, for a relatively wide range of properties, microdroplets of controlled, uniform size can be generated using methods like T-junctions and flow focusing. To vary microdroplet size, the flow rates of the immiscible liquids may be varied since, for T-junction and flow focus methodologies over a certain range of properties, microdroplet size depends on total flow rate and the ratio of the two fluid flow rates. To generate an emulsion with microfluidic methods, the two fluids are normally loaded into two inlet reservoirs (syringes, pressure tubes) and then pressurized as needed to generate the desired flow rates (using syringe pumps, pressure regulators, gravity, etc.). This pumps the fluids through the device at the desired flow rates, thus generating microdroplet of the desired size and rate.

Adding Reagents to Discrete Entities

In practicing the subject methods, a number of reagents may be added to, i.e., incorporated into and/or encapsulated by, the discrete entities, e.g., microdroplets, in one or more steps (e.g., about 2, about 3, about 4, or about 5 or more steps). Such reagents may include, for example, amplification reagents, such as Polymerase Chain Reaction (PCR) reagents. The methods of adding reagents to the discrete entities, e.g., microdroplets, may vary in a number of ways. Approaches of interest include, but are not limited to, those described by Ahn, et al., Appl. Phys. Lett. 88, 264105 (2006); Priest, et al., Appl. Phys. Lett. 89, 134101 (2006); Abate, et al., PNAS, Nov. 9, 2010 vol. 107 no. 45 19163-19166; and Song, et al., Anal. Chem., 2006, 78 (14), pp 4839-4849; the disclosures of which are incorporated herein by reference.

For instance, a reagent may be added to a discrete entity, e.g., microdroplet, by a method involving merging a discrete entity, e.g., a microdroplet, with a second discrete entity, e.g., microdroplet, which contains the reagent(s). The reagent(s) that are contained in the second discrete entity may be added by any convenient methods, specifically including those described herein. This second discrete entity may be merged with the first discrete entity to create a discrete entity, e.g., a microdroplet, which includes the contents of both the first discrete entity and the second discrete entity.

One or more reagents may also, or instead, be added using techniques such as droplet coalescence, or picoinjection. In droplet coalescence, a target drop (i.e., the microdroplet) may be flowed alongside a microdroplet containing the reagent(s) to be added to the microdroplet. The two microdroplets may be flowed such that they are in contact with each other, but not touching other microdroplets. These drops may then be passed through electrodes or other aspects for applying an electrical field, wherein the electric field may destabilize the microdroplets such that they are merged together.

Reagents may also, or instead, be added using picoinjection. In this approach, a target drop (i.e., the microdroplet) may be flowed past a channel containing the reagent(s) to be added, wherein the reagent(s) are at an elevated pressure. Due to the presence of the surfactants, however, in the absence of an electric field, the microdroplet will flow past without being injected, because surfactants coating the microdroplet may prevent the fluid(s) from entering. However, if an electric field is applied to the microdroplet as it passes the injector, fluid containing the reagent(s) will be injected into the microdroplet. The amount of reagent added to the microdroplet may be controlled by several different parameters, such as by adjusting the injection pressure and the velocity of the flowing drops, by switching the electric field on and off, and the like.

In various aspects, one or more reagents may also, or instead, be added to a microdroplet by a method that does not rely on merging two droplets together or on injecting liquid into a drop. Rather, one or more reagents may be added to a microdroplet by a method involving the steps of emulsifying a reagent into a stream of very small drops, and merging these small drops with a target microdroplet. Such methods shall be referred to herein as "reagent addition through multiple-drop coalescence." These methods take advantage of the fact that due to the small size of the drops to be added compared to that of the target drops, the small drops will flow faster than the target drops and collect behind them. The collection can then be merged by, for example, applying an electric field. This approach can also, or instead, be used to add multiple reagents to a microdroplet by using several co-flowing streams of small drops of different fluids. To enable effective merger of the tiny and target drops, it is important to make the tiny drops smaller than the channel containing the target drops, and also to make the distance between the channel injecting the target drops from the electrodes applying the electric field sufficiently long so as to give the tiny drops time to "catch up" to the target drops. If this channel is too short, not all tiny drops will merge with the target drop, adding less reagent than desired. To a certain degree, this can be compensated for by increasing the magnitude of the electric field, which tends to allow drops that are farther apart to merge. In addition to making the tiny drops on the same microfluidic device, they can also, or instead, be made offline using another microfluidic drop maker or through homogenization and then injecting them into the device containing the target drops.

Accordingly, in some embodiments a reagent is added to a microdroplet by a method involving emulsifying the reagent into a stream of droplets, wherein the droplets are smaller than the size of the microdroplet; flowing the droplets together with the microdroplet; and merging a droplet with the microdroplet. The diameter of the droplets contained in the stream of droplets may vary ranging from about 75% or less than that of the diameter of the microdroplet, e.g., the diameter of the flowing droplets is about 75% or less than that of the diameter of the microdroplet, about 50% or less than that of the diameter of the microdroplet, about 25% or less than that of the diameter of the microdroplet, about 15% or less than that of the diameter of the microdroplet, about 10% or less than that of the diameter of the microdroplet, about 5% or less than that of the diameter of the microdroplet, or about 2% or less than that of the diameter of the microdroplet. In certain aspects, a plurality of flowing droplets may be merged with the microdroplet, such as 2 or more droplets, 3 or more, 4 or more, or 5 or more. Such merging may be achieved in a variety of ways, including but not limited to by applying an electric field, wherein the electric field is effective to merge the flowing droplet with the microdroplet.

A reagent, in another aspect, is added to a drop (e.g., a microdroplet) formed at an earlier time by enveloping the drop to which the reagent is be added (i.e., the "target drop") inside a drop containing the reagent to be added (the "target reagent"). In certain embodiments such a method is carried out by first encapsulating the target drop in a shell of a suitable hydrophobic phase, e.g., oil, to form a double emulsion. The double emulsion is then encapsulated by a drop containing the target reagent to form a triple emulsion. To combine the target drop with the drop containing the target reagent, the double emulsion is then burst open using any suitable method, including, but not limited to, applying an electric field, adding chemicals that destabilizes the droplet interface, flowing the triple emulsion through constrictions and other microfluidic geometries, applying mechanical agitation or ultrasound, increasing or reducing temperature, or by encapsulating magnetic particles in the drops that can rupture the double emulsion interface when pulled by a magnetic field.

Sorting

In practicing the methods of the present disclosure, one or more sorting steps may be employed. Sorting approaches of interest include, by are not necessarily limited to, approaches that involve the use of one or more sorters, e.g., sorters of a microfluidic device, which employ microfluidic valves, membrane valves, bifurcating channels, surface acoustic waves, and/or dielectrophoresis. Sorting approaches which may be utilized in connection with the disclosed methods, systems and devices also include those depicted in FIG. 4, Panels C and D, and those described by Agresti, et al., PNAS vol. 107, no 9, 4004-4009; the disclosure of which is incorporated herein by reference. A population, e.g., a population of discrete entities, may be enriched by sorting, in that a population containing a mix of members having or not having a desired property may be enriched by removing those members that do not have the desired property, thereby producing an enriched population having the desired property.

In various embodiments, the subject methods include scanning, e.g., optically scanning one or more discrete entities, e.g., microdroplets, to facilitate sorting of the discrete entities. As such, in some embodiments, microfluidic devices or portions thereof, e.g., sorters, include one or more detectors, e.g., optical scanners. A variety of suitable optical scanners are known in the art. Such optical scanners may include, e.g., one or more optical fibers for applying excitation energy to one or more discrete entities. In some embodiments, a suitable optical scanner utilizes a laser light source directed into the back of an objective, and focused onto a microfluidic channel through which droplets flow, e.g., to excite fluorescent dyes within one or more discrete entities. Scanning one more discrete entities may allow one or more properties, e.g., size, shape, composition, of the scanned entities to be determined. Sorting may, in turn, be carried out based on the one or more properties. For example, sorting may be based on results obtained from an optical scan of one or more discrete entities.

Properties of discrete entities which may be detected include, but are not limited to, the size, viscosity, mass, buoyancy, surface tension, electrical conductivity, charge, magnetism, and/or presence or absence of one or more components, e.g., one or more detectable labels (e.g., one or more fluorescent labels). In certain aspects, sorting may be based at least in part upon the presence or absence of one or more cells in the microdroplet, e.g., one or more detectably labeled cells. In certain aspects, sorting may be based at least in part based upon the detection of the presence or absence of PCR amplification products.

Sorting may be applied at any suitable point in the disclosed methods. Moreover, two or more sorting steps may be applied to a population of discrete entities or types thereof, e.g., microdroplets, e.g., about 2 or more sorting steps, about 3 or more, about 4 or more, or about 5 or more, etc. When a plurality of sorting steps is applied, the steps may be substantially identical or different in one or more ways (e.g., sorting based upon a different property, sorting using a different technique, and the like).

Moreover, discrete entities, e.g., droplets, may be purified prior to, or after, any sorting step. In one embodiment a droplet may be purified as follows: a majority of the fluid in the drop is replaced it with a purified solution, without removing any discrete reagents that may be encapsulated in the drop, such a cells or beads. The microdroplet is first injected with a solution to dilute any impurities within it. The diluted microdroplet is then flowed in air via the air-liquid co-flow junction to the delivery orifice, where an electric field is being applied using electrodes. Due to the dielectrophoretic forces generated by the field, as the cells or other discrete reagents pass through the field they will be displaced in the flow. The drops are then split, so that all the objects end up in one microdroplet. Accordingly, the initial microdroplet has been purified, in that the contaminants may be removed while the presence and/or concentration of discrete reagents, such as beads or cells, which may be encapsulated within the droplet, are maintained in the resulting microdroplet.

Microdroplets may be sorted based on one or more properties. Properties of interest include, but are not limited to, the size, viscosity, mass, buoyancy, surface tension, electrical conductivity, charge, magnetism, and/or presence or absence of one or more components, e.g., one or more detectable labels. In certain aspects, sorting may be based at least in part upon the presence or absence of one or more cells in the microdroplet, e.g., one or more detectably labeled cells. In certain aspects, sorting may be based at least in part based upon the detection of the presence or absence of PCR amplification products.

Sorting may be employed, for example, to remove discrete entities, e.g., microdroplets, in which no cells are present. Encapsulation may result in one or more discrete entities, e.g., microdroplets, including a majority of the discrete entities, e.g., microdroplets, in which no cell is present. If such empty drops were left in the system, they would be processed as any other drop, during which reagents and time would be wasted. To achieve the highest speed and efficiency, these empty drops may be removed with droplet sorting. For example, a drop maker may operate close to the dripping-to-jetting transition such that, in the absence of a cell, drops of a first size, e.g., 8 μm, are formed; by contrast, when a cell is present the disturbance created in the flow will trigger the breakup of the jet, forming drops of a second size, e.g., 25 μm in diameter. The device may thus produce a bi-disperse population of empty drops of a first size, e.g., 8 μm, and single-cell containing drops of a second size, e.g., 25 μm, which may then be sorted by size using, e.g., a hydrodynamic sorter to recover only the, single-cell containing drops of the second, e.g., larger, size.

Sorters of the subject embodiments may be active or passive sorters. Passive sorters of interest include hydrodynamic sorters, which sort discrete entities, e.g., microdroplets, into different channels according to size, based on the different ways in which small and large drops travel through the microfluidic channels. Also of interest are bulk sorters, a simple example of which is a tube containing drops of different mass in a gravitational field. By centrifuging, agitating, and/or shaking the tube, lighter drops that are more buoyant will naturally migrate to the top of the container. Drops that have magnetic properties could be sorted in a similar process, except by applying a magnetic field to the container, towards which drops with magnetic properties will naturally migrate according to the magnitude of those properties. A passive sorter as used in the subject methods may also involve relatively large channels that will sort large numbers of drops simultaneously based on their flow properties. Additionally, in some embodiments, sorting is carried out via activation of one or more valves, e.g., microfluidic valves.

Picoinjection can also be used to change the electrical properties of the drops. This could be used, for example, to change the conductivity of the drops by adding ions, which could then be used to sort them, for example, using dielectrophoresis. Alternatively, picoinjection can also be used to charge the drops. This could be achieved by injecting a fluid into the drops that is charged, so that after injection, the drops would be charged. This would produce a collection of drops in which some were charged and others not, and the charged drops could then be extracted by flowing them in air through a region of electric field, which will deflect them based on their charge amount. By injecting different amounts of liquid by modulating the piocoinjection, or by modulating the voltage to inject different charges for affixed injection volume, the final charge on the drops could be adjusted, to produce drops with different charge. These would then be deflected by different amounts in the electric field region, allowing them to be sorted into different containers.

Improved Sorting Architecture for High-Speed Sorting of Microdroplets

In some embodiments, the present disclosure provides microfluidic devices with an improved sorting architecture, which facilitates the high-speed sorting of discrete entities, e.g., microdroplets. This sorting architecture may be used in connection with the microdroplet printer embodiments described herein or in any other suitable application where high-speed sorting of microdroplets is desired. Related methods and systems are also described. For example, in some embodiments, microfluidic devices are provided which include at least a flow channel.

In some embodiments a microfluidic device according to the present disclosure includes an electrode, e.g., a liquid electrode, configured to selectively apply an electrical field to effect sorting of one or more microdroplets.

In some embodiments, liquid electrodes include liquid electrode channels filled with a conducting liquid (e.g. salt water or buffer) and situated at positions in the microfluidic device where an electric field is desired. In particular embodiments, the liquid electrodes are energized using a power supply or high voltage amplifier. In some embodiments, the liquid electrode channel includes an inlet port so that a conducting liquid can be added to the liquid electrode channel. Such conducting liquid may be added to the liquid electrode channel, for example, by connecting a tube filled with the liquid to the inlet port and applying pressure. In particular embodiments, the liquid electrode channel also includes an outlet port for releasing conducting liquid from the channel.

In alternative embodiments, a solid electrode prepared from any suitable conductive material may be utilized.

As described herein, microfluidic devices according to the present disclosure may include a moat salt solution (to generate the field gradient used for dielectrophoretic deflection and to limit stray fields that can cause unintended droplet merger) provided in suitable channels.

Printing Cell Layers

In some embodiments, the present disclosure provides methods and related devices and systems for printing one or more tissues and/or cell layers. FIG. 1 depicts a non-limiting, simplified representation of one type of microfluidic system and method of the present disclosure which may be utilized in the printing of one or more tissues or cell layers. FIG. 1 illustrates the delivery of discrete entities including cells to a substrate. In one such method, discrete entities, e.g., droplets 101, are prepared using a device, e.g., a microfluidic device 100. Discrete entities, e.g., droplets 101, as shown in FIG. 1 may include one or more reagent, e.g., a reagent which facilitates cell growth and/or a cell culture media component and/or a cell culture substrate, e.g., a matrigel, and different types of cells. The subject method may include encapsulating, e.g., encapsulating by fully containing therein, one or more cells in a discrete entity.

In some aspects of printing tissues, the discrete entities 101 are flowed in a liquid 102 through a flow channel to the air-liquid co-flow junction 104, where the air from the air channels 103 directs the discrete entities 101 to the delivery orifice 105 and subsequently to a sorter, which sorts the discrete entities 101 based on one or more of their characteristics. As shown in FIG. 1, the sorter may be configured to detect and/or separate discrete entities 101 containing cells based on cell type. For this purpose, the sorter may comprise a laser 106 connected to optical fibers configured to apply excitation energy 107, which apply excitation energy to the discrete entities 101 comprising cells flowing through the delivery orifice 105 and optical fibers configured to collect a signal produced by the application of excitation energy 108 to the discrete entities 101. The sorter may further comprise an electrode 109 that can sort the discrete entities 101 comprising cells based on detection of property, e.g., an optical property, by the laser 106 and optical fiber system 107 and 108. In some embodiments, when the electrode 109 is turned on by application of a voltage, discrete entities 101 comprising certain cell types are deposited on the substrate 117. In certain embodiments, when the electrode 109 is turned on by application of a voltage, the discrete entities comprising certain cell types are directed to the waste reservoir 110.

A sorter may be configured to separate a first type of discrete entity, e.g., a droplet type containing one or more cell of interest, and a second type, e.g., a type not containing one or more cell of interest. As such, a sorter may produce a first fraction, e.g., a fluid containing discrete entities having a first type, e.g., one or more type of interest, and a second fraction, e.g., a fluid containing discrete entities having a second type, e.g., one or more type not of interest. The sorter may also be configured to direct the first fraction for delivery to a substrate 117 and the second fraction toward a waste reservoir 110, optionally connected to a vacuum pump 111. Alternatively, the second fraction may be recycled by reintroducing it upstream of the sorter. In some embodiments, a delivery orifice 105, may be positioned from about 1 µm to about 200 µm, such as from about 5 µm to about 100 µm, or from about 10 µm to about 50 µm, inclusive, such as about 20 µm away from a target such as surface of a substrate 117 or a previously deposited layer of discrete entities.

In some variations, the methods may include affixing a first layer of discrete entities, e.g., discrete entities including a first cell type, to a substrate surface of a substrate 117 and one or more other layers, e.g., a second layer of discrete entities, e.g., discrete entities including a second cell type, to the first layer of discrete entities. In various embodiments, a first layer of discrete entities can be applied to a substrate surface before, or contemporaneously with, a second layer. Aspects of the methods may also include affixing one or more additional layers of discrete entities 101, e.g., discrete entities encapsulating cells, to one or more previously affixed layer. For example, the subject methods may include affixing between 1 and 10 million, inclusive, such as between 10 and 1 million or between 100 and 10,000, inclusive, additional layers of discrete entities. Accordingly, the methods may include providing a layered structure, e.g., a tissue, by repeated layering of discrete entity layers. It should be noted that each layer may include discrete entities of a specific type or a plurality of discrete entities of different types, e.g., discrete entities having varying compositions or components. For example, first layer and/or a second layer may include a plurality of discrete entities including different cell types, e.g., a first discrete entity including a first cell type and a second discrete entity including a second different cell type than the first discrete entity. In other words, each layer may include either a homogenous or heterogeneous population of discrete entities, e.g., microdroplets.

In some embodiments, substrates or portions thereof, e.g., substrate surfaces, include one or more electrodes. Such electrodes may be used to apply a force, to thereby cause a first layer, e.g., initial layer, of discrete entities to affix to, e.g., wet, a substrate or a substrate surface thereof. Once a first layer, e.g., initial layer, of discrete entities is applied, electric field gradients at drop surfaces of discrete entities of the first layer may cause subsequent discrete entities, e.g., discrete entities of a second layer, to affix to, e.g., wet, the first layer.

Detecting Cells

In some embodiments, the subject methods involve detecting the presence and/or absence of one or more cells or one or more other characteristics, such as type and/or size, of one or more subset of cells (e.g., tumor cells) in one or more discrete entities, and/or before, during or after the discrete entity is affixed to a layer of discrete entities, a substrate, or a portion thereof, e.g., a substrate surface, as described herein. In some embodiments, a sorter of a microfluidic device is utilized for detecting one or more characteristics of cells encapsulated within discrete entities.

Aspects of the disclosed methods may include detecting one or more characteristics of cells, e.g., one or more cells within discrete entities affixed to a substrate, at a plurality of time points, e.g., a plurality of equally-spaced time points. The methods may also include detecting one or more characteristics of one or more cells continuously over a period of time, such as detecting a component of the one or more cells, and/or a product of the one or more cells. Embodiments of the methods may further include recovering, e.g., recovering by extracting, from a discrete entity one or more cells, a component of one or more cells, e.g., deoxyribonucleic acid (DNA), and/or a product of one or more cells. In various embodiments, the methods may include sequencing DNA recovered from one or more cells.

Aspects of the disclosed methods may include incorporating discrete entities having one or more cells obtained from a biological sample.

As used herein, the term "biological sample" encompasses a variety of sample types obtained from a variety of sources, which sample types contain biological material. For example, the term includes biological samples obtained from a mammalian subject, e.g., a human subject, and biological samples obtained from a food, water, or other environmental source, etc. The definition encompasses blood and other liquid samples of biological origin, as well as solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, cells, serum, plasma, biological fluid, and tissue samples. "Biological sample" includes cells; biological fluids such as blood, cerebrospinal fluid, semen, saliva, and the like; bile; bone marrow; skin (e.g., skin biopsy); and antibodies obtained from an individual.

As is described more fully herein, in various aspects the subject methods may be used to detect a variety of components from cells, such as cells from biological samples. Components of interest include, but are not necessarily limited to, cells (e.g., circulating cells and/or circulating tumor cells), polynucleotides (e.g., DNA and/or RNA), polypeptides (e.g., peptides and/or proteins), and many other components that may be present in a biological sample.

"Polynucleotides" or "oligonucleotides" as used herein refer to linear polymers of nucleotide monomers, and may be used interchangeably. Polynucleotides and oligonucleotides can have any of a variety of structural configurations, e.g., be single stranded, double stranded, or a combination of both, as well as having higher order intra- or intermolecular secondary/tertiary structures, e.g., hairpins, loops, triple stranded regions, etc. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in $5' \rightarrow 3'$ order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, *Human Molecular Genetics* 2 (Wiley-Liss, New York, 1999).

The terms "polypeptide," "peptide," and "protein," used interchangeably herein, refer to a polymeric form of amino acids of any length. $NH_2$ refers to the free amino group present at the amino terminus of a polypeptide. COOH refers to the free carboxyl group present at the carboxyl terminus of a polypeptide. In keeping with standard polypeptide nomenclature, J Biol. Chem., 243 (1969), 3552-3559 is used.

In certain aspects, methods are provided for counting and/or genotyping cells, including normal cells or tumor cells. A feature of such methods is the use of microfluidics.

According to some embodiments of the subject methods, cells, e.g., cells in discrete entities and/or affixed to a substrate, a biological sample (e.g., whole blood) may be recovered from a subject using any convenient method, e.g., by applying a needle and/or a syringe. The biological sample may then be processed to remove components other than cells using, for example, processing steps such as centrifugation, filtration, and the like.

Each cell in the biological sample, or a subset thereof, may then be encapsulated into a discrete entity, e.g., a droplet, using a microfluidic device. Methods and devices which may be utilized in the encapsulating of a component from a biological sample are described in PCT Publication No. WO 2014/028378, the disclosure of which is incorporated by reference herein in its entirety and for all purposes. Encapsulation approaches of interest also include, but are not limited to, hydrodynamically-triggered drop formation and those described by Link, et al., *Phys. Rev. Lett.* 92, 054503 (2004), the disclosure of which is incorporated herein by reference. Other methods of encapsulating cells into droplets may also be applied. Where desired, the cells may be stained with one or more antibodies and/or probes prior to encapsulating them into drops.

One or more lysing agents may also be added to the discrete entities, e.g., droplets, containing a cell, under conditions in which the cell(s) may be caused to burst, thereby releasing their genomes. The lysing agents may be added after the cells are encapsulated into discrete entities, e.g., microdroplets. Any convenient lysing agent may be employed, such as proteinase K or cytotoxins. In particular embodiments, cells may be co-encapsulated in drops with lysis buffer containing detergents such as Triton X100 and/or proteinase K. The specific conditions in which the cell(s) may be caused to burst will vary depending on the specific lysing agent used. For example, if proteinase K is incorporated as a lysing agent, the discrete entities, e.g., droplets, may be heated to about 37-60° C. for about 20 min to lyse the cells and to allow the proteinase K to digest cellular proteins, after which they may be heated to about 95° C. for about 5-10 min to deactivate the proteinase K.

In certain aspects, cell lysis may also, or instead, rely on techniques that do not involve addition of lysing agent. For example, lysis may be achieved by mechanical techniques that may employ various geometric features to effect piercing, shearing, abrading, etc. of cells. Other types of mechanical breakage such as acoustic techniques may also be used. Further, thermal energy can also be used to lyse cells. Any convenient methods of effecting cell lysis may be employed in the methods described herein.

One or more primers may be introduced into the discrete entities, e.g., droplets, for each of the genes, e.g., oncogenes, to be detected. Hence, in certain aspects, primers for all target genes, e.g., oncogenes, may be present in the discrete entity, e.g., droplet, at the same time, thereby providing a multiplexed assay. The discrete entities, e.g., droplets, may be temperature-cycled so that discrete entities, e.g., droplets, containing cancerous cells, for example, will undergo PCR. During this time, only the primers corresponding to genes, e.g., oncogenes, present in the genome will induce amplification, creating many copies of these genes, e.g., oncogenes, in the discrete entity, e.g., droplet. Detecting the presence of these PCR products may be achieved by a variety of ways, such as by using FRET, staining with an intercalating dye, or attaching them to a bead. More information on the different options for such detection is also provided herein. The discrete entity, e.g., droplet, may be optically probed, e.g., probed using a laser, to detect the PCR products. Optically probing the discrete entity, e.g., droplet, may involve counting the number of target cells, e.g., tumor cells, present in the initial population, and/or to allow for the identification the target, e.g., oncogenes, present in each cell, e.g., tumor cell.

Aspects of the subject methods may be used to determine whether a biological sample contains particular cells of interest, e.g., tumor cells, or not. In certain aspects, the subject methods may include quantifying the number of cells of interest, e.g., tumor cells, present in a biological sample. Quantifying the number of cells of interest, e.g., tumor cells, present in a biological sample may be based at least in part on the number of discrete entities, e.g., droplets, in which PCR amplification products were detected. For example, discrete entities, e.g., droplets, may be produced under conditions in which the majority of discrete entities, e.g., droplets, are expected to contain zero or one cells. Those discrete entities, e.g., droplets, that do not contain any cells may be removed, using techniques described more fully herein. After performing the PCR steps outlined above, the total number of discrete entities, e.g., droplets, that are detected to contain PCR products may be counted, so as to quantify the number of cells of interest, e.g., tumor cells, in the biological sample. In certain aspects, the methods may also include counting the total number of discrete entities, e.g., droplets, so as to determine the fraction or percentage of cells from the biological sample that are cells of interest, e.g., tumor cells.

Devices

As indicated above, embodiments of the disclosed subject matter employ systems and/or devices including microfluidic devices. Devices of the subject disclosure include all those described above in association with the subject methods. Microfluidic devices of this disclosure may be characterized in various ways.

In certain embodiments, for example, systems and/or devices are provided which include one or more discrete entity, e.g., droplet, printers. Discrete entity printers may include one or more microfluidic device, such as a microfluidic device including one or more discrete entity makers, e.g., droplet makers, configured to generate discrete entities, e.g., droplets, as described herein, and/or one or more flow channels. In some embodiments, the one or more flow channels are operably connected, e.g., fluidically connected, to the one or more droplet makers and/or are configured to receive one or more droplets therefrom. By "operably connected" and "operably coupled", as used herein, is meant connected in a specific way (e.g., in a manner allowing fluid, e.g., water, to move and/or electric power to be transmitted) that allows a disclosed system or device and its various components to operate effectively in the manner described herein.

Aspects of the disclosed devices also include one or more air/liquid co-flow junctions, such as an air/liquid co-flow junction connected to one or more air channels. In some embodiments, the disclosed devices include an opening, such as a delivery orifice, e.g., a circular or oblong opening, through which one or more discrete entities may pass. In some embodiments, openings of devices are defined by a rim of a device or a portion thereof, e.g., a nozzle, such as a positionable nozzle. Air/liquid co-flow junctions, as included in the subject embodiments, may have any of the same dimensions, e.g., a cross-sectional dimension, as the air channels described herein, or may have different dimensions.

A delivery orifice as described herein will generally have dimensions that are similar to the size of the droplets to be delivered therethrough. Accordingly, in some embodiments, the delivery orifice as described herein has a diameter of from about 1 μm to about 1000 μm, inclusive, e.g., from about 10 μm to about 300 μm, inclusive. In some embodiments, the delivery orifice as described herein has a diameter of from about 1 μm to about 10 μm, from about 10 μm to about 100 μm, from about 100 μm to about 500 μm, or from about 500 μm to about 1000 μm, inclusive.

Suitable materials for the delivery orifice, e.g. nozzle, may include, e.g., polymeric tubing, small bore hypodermic tubing, and modified glass capillaries.

Embodiments of the subjects disclosure also include devices including one or more automated system integrated with the air/liquid co-flow junction or delivery orifice, wherein the automated system (a) selectively positions, e.g., positions by moving one or more distance on the order of magnitude of a discrete entity, the air/liquid co-flow junction or delivery orifice in proximity to a substrate or a portion thereof during operation and/or (b) selectively positions, e.g., positions by moving one or more distance on the order of magnitude of a discrete entity, the substrate or portion thereof in proximity to the air/liquid co-flow or delivery orifice junction during operation, such that a discrete entity, e.g., a droplet, can be ejected from the air/liquid co-flow junction or delivery orifice and/or deposited on the substrate.

In some embodiments, automated systems are electronic and/or include one or more control unit for controlling automation, such as a control unit including a central processing unit.

As noted above, droplet printers may include one or more flow channels, e.g., flow channels which discrete entities may pass into, out of, and/or through. The flow channels may comprise air channels and channels for flowing liquid such as flow channels. In certain embodiments, flow channels are one or more "micro" channel. Such channels may have at least one cross-sectional dimension on the order of a millimeter or smaller (e.g., less than or equal to about 1 millimeter). For certain applications, this dimension may be adjusted; in some embodiments the at least one cross-sectional dimension is about 500 micrometers or less. In some embodiments, the cross-sectional dimension is about 100 micrometers or less, or about 10 micrometers or less, and sometimes about 1 micrometer or less. A cross-sectional dimension is one that is generally perpendicular to the direction of centerline flow, although it should be understood that when encountering flow through elbows or other features that tend to change flow direction, the cross-sectional dimension in play need not be strictly perpendicular to flow. It should also be understood that in some embodiments, a micro-channel may have two or more cross-sectional dimensions such as the height and width of a rectangular cross-section or the major and minor axes of an elliptical cross-section. Either of these dimensions may be compared against sizes presented here. Note that micro-channels employed in this disclosure may have two dimensions that are grossly disproportionate—e.g., a rectangular cross-section having a height of about 100-200 micrometers and a width on the order or a centimeter or more. Of course, certain devices may employ channels in which the two or more axes are very similar or even identical in size (e.g., channels having a square or circular cross-section).

Microfluidic devices, in some embodiments of this disclosure, are fabricated using microfabrication technology. Such technology may be employed to fabricate integrated circuits (ICs), microelectromechanical devices (MEMS), display devices, and the like. Among the types of microfabrication processes that can be employed to produce small dimension patterns in microfluidic device fabrication are photolithography (including X-ray lithography, e-beam lithography, etc.), self-aligned deposition and etching technologies, anisotropic deposition and etching processes, self-assembling mask formation (e.g., forming layers of hydrophobic-hydrophilic copolymers), etc.

In view of the above, it should be understood that some of the principles and design features described herein can be scaled to larger devices and systems including devices and systems employing channels reaching the millimeter or even centimeter scale channel cross-sections. Thus, when describing some devices and systems as "microfluidic," it is intended that the description apply equally, in certain embodiments, to some larger scale devices.

When referring to a microfluidic "device" it is generally intended to represent a single entity in which one or more channels, reservoirs, stations, etc. share a continuous substrate, which may or may not be monolithic. Aspects of microfluidic devices include the presence of one or more fluid flow paths, e.g., channels, having dimensions as discussed herein. A microfluidics "system" may include one or more microfluidic devices and associated fluidic connections, electrical connections, control/logic features, etc.

For example, systems of the subject disclosure may include one or more discrete entity printer, e.g., one or more droplet printer, and/or a substrate or portion thereof, e.g., a substrate surface, for receiving one or more discrete entities, e.g., droplets deposited thereon by, for example, a delivery orifice via an air/liquid co-flow junction of a discrete entity printer, e.g., a droplet printer. Systems may also include one or more of: (a) a temperature control module for controlling the temperature of one or more portions of the subject devices and/or discrete entities therein and which is operably connected to the discrete entity printer, e.g., a droplet printer, (b) a detection means, i.e., a detector, e.g., an optical imager, operably connected to the discrete entity printer, e.g., a droplet printer, and (c) an incubator, e.g., a cell incubator, operably connected to the discrete entity printer, e.g., a droplet printer. The subject systems may also include one or more conveyor configured to move, e.g., convey, a substrate from a first discrete entity, e.g., droplet, receiving position to one or more of (a)-(c).

The subject devices and systems, include one or more sorter for sorting discrete entities, e.g., droplets. Such a sorter may sort and distribute discrete entities, e.g., droplets, based on one or more characteristics of the discrete entities including composition, size, shape, buoyancy, or other characteristics.

Aspects of the devices also include one or more detection means i.e., a detector, e.g., an optical imager, configured for detecting the presence of one or more discrete entities, e.g., droplets, or one or more characteristics thereof, including their composition. In some embodiments, detection means are configured to recognize one or more components of one or more discrete entities, e.g., discrete entities, in one or more flow channel.

In various embodiments, microfluidic devices of this disclosure provide a continuous flow of a fluid medium. Fluid flowing through a channel in a microfluidic device exhibits many unique properties. Typically, the dimensionless Reynolds number is extremely low, resulting in flow that always remains laminar. Further, in this regime, two fluids joining will not easily mix, and diffusion alone may drive the mixing of two compounds.

In addition, the subject devices, in some embodiments, include one or more temperature and/or pressure control module. More specifically, a temperature control module may be one or more thermal cycler.

Various features and examples of microfluidic device components suitable for use with this disclosure will now be described.

Substrate

According to the subject disclosure, substrates used in microfluidic devices and/or systems are the supports in which the necessary elements for fluid transport are provided. The basic structure of a substrate may be monolithic, laminated, or otherwise sectioned. Substrates may include one or more flow channels, such as microchannels serving as conduits for molecular libraries and/or reagents. They may also include input ports, output ports, and/or features to assist in flow control.

In certain embodiments, the substrate choice may be dependent on the application and design of the device. Substrate materials may be chosen for their compatibility with a variety of operating conditions. Limitations in microfabrication processes for a given material are also relevant considerations in choosing a suitable substrate. Useful substrate materials which may be employed with the subject disclosure include, e.g., glass, polymers, silicon, metal, ceramics, and/or combinations thereof.

The subject devices, in some embodiments, include one or more polymers. Polymers are useful materials for microfluidic devices because they are amenable to both cost effective and high volume production. Polymers, including polymers for use in accordance with the subject disclosure, can be classified into three categories according to their molding behavior: thermoplastic polymers, elastomeric polymers and duroplastic polymers. Thermoplastic polymers can be molded into shapes above the glass transition temperature, and will retain these shapes after cooling below the glass transition temperature. Elastomeric polymers can be stretched upon application of an external force, but will go back to original state once the external force is removed. Elastomers do not melt before reaching their decomposition temperatures. Duroplastic polymers have to be cast into their final shape because they soften a little before the temperature reaches their decomposition temperature.

Among the polymers that may be used in microfabricated device of this disclosure are polyamide (PA), polybutylenterephthalate (PBT), polycarbonate (PC), polyethylene (PE), polymethylmethacrylate (PMMA), polyoxymethylene (POM), polypropylene (PP), polyphenylenether (PPE), polystyrene (PS) and polysulphone (PSU). The chemical and physical properties of polymers can limit their uses in microfluidic devices. Specifically in comparison to glass, the lower resistance against chemicals, the aging, the mechanical stability, and the UV stability can limit the use of polymers for certain applications.

Glass, which may also be used as the substrate material, has specific advantages under certain operating conditions. Since glass is chemically inert to most liquids and gases, it is particularly appropriate for applications employing certain solvents that have a tendency to dissolve plastics. Additionally, its transparent properties make glass particularly useful for optical or UV detection.

Surface Treatments and Coatings

Surface modification may be useful for controlling the functional mechanics (e.g., flow control) of a microfluidic device and may be applied according to the subject disclosure. For example, it may be useful to keep fluidic species from adsorbing to channel walls or for attaching antibodies to the surface for detection of biological components.

Polymer devices in particular tend to be hydrophobic, and thus loading of the channels may be difficult. The hydrophobic nature of polymer surfaces may also make it difficult to control electroosmotic flow (EOF). One technique for coating polymer surface according to the subject disclosure is the application of polyelectrolyte multilayers (PEM) to channel surfaces. PEM involves filling the channel successively with alternating solutions of positive and negative polyelectrolytes allowing for multilayers to form electrostatic bonds. Although the layers typically do not bond to the channel surfaces, they may completely cover the channels even after long-term storage. Another technique for applying a hydrophilic layer on polymer surfaces according to the subject disclosure involves the UV grafting of polymers to the surface of the channels. First grafting sites, radicals, are created at the surface by exposing the surface to UV irradiation while simultaneously exposing the device to a monomer solution. The monomers react to form a polymer covalently bonded at the reaction site.

In some embodiments, glass channels according to the subject disclosure, generally have high levels of surface charge, thereby causing proteins to adsorb and possibly hindering separation processes. In some situations, the disclosure includes applying a polydimethylsiloxane (PDMS) and/or surfactant coating to the glass channels. Other polymers that may be employed to retard surface adsorption include polyacrylamide, glycol groups, polysiloxanes, glyceroglycidoxypropyl, poly(ethyleneglycol) and hydroxyethylated poly(ethyleneimine). Furthermore, subject electroosmotic devices may include a coating bearing a charge that is adjustable in magnitude by manipulating conditions inside of the device (e.g. pH). The direction of the flow can also be selected based on the coating since the coating can either be positively or negatively charged.

Specialized coatings can also be applied according to this disclosure to immobilize certain species on the channel surface—this process is called "functionalizing the surface." For example, a polymethylmethacrylate (PMMA) surface may be coated with amines to facilitate attachment of a variety of functional groups or targets. Alternatively, PMMA surfaces can be rendered hydrophilic through an oxygen plasma treatment process.

Microfluidic Elements

Microfluidic systems and devices according to the subject disclosure can contain one or more flow channels, such as microchannels, valves, pumps, reactors, mixers and other/or components. Some of these components and their general structures and dimensions are discussed below.

Various types of valves can be applied for flow control in microfluidic devices of this disclosure. These include but are not limited to passive valves and check valves (membrane, flap, bivalvular, leakage, etc.). Flow rate through these valves are dependent on various physical features of the valve such as surface area, size of flow channel, valve material, etc. Valves also have associated operational and manufacturing advantages/disadvantages that may be taken into consideration during design of a microfluidic device.

Embodiments of the subject devices include one or more micropumps. Micropumps, as with other microfluidic components, are subjected to manufacturing constraints. Typical considerations in pump design include treatment of bubbles, clogs, and durability. Micropumps which may be included in the subject devices include, but are not limited to electric equivalent pumps, fixed-stroke microdisplacement, peristaltic micromembrane and/or pumps with integrated check valves.

Macrodevices rely on turbulent forces such as shaking and stirring to mix reagents. In comparison, such turbulent forces are not practically attainable in microdevices, such as those of the present disclosure, and instead mixing in microfluidic devices is generally accomplished through diffusion. Since mixing through diffusion can be slow and inefficient, microstructures, such as those employed with the disclosed subject matter, are often designed to enhance the mixing process. These structures manipulate fluids in a way that increases interfacial surface area between the fluid regions, thereby speeding up diffusion. In certain embodiments, microfluidic mixers are employed. Such mixers may be provided upstream from, and in some cases integrated with, a microfluidic separation device and/or a sorter, of this disclosure.

In some embodiments, the devices and systems of the present disclosure include micromixers. Micromixers may be classified into two general categories: active mixers and passive mixers. Active mixers work by exerting active control over flow regions (e.g. varying pressure gradients, electric charges, etc.). Passive mixers do not require inputted energy and use only "fluid dynamics" (e.g. pressure) to drive fluid flow at a constant rate. One example of a passive mixer involves stacking two flow streams on top of one another separated by a plate. The flow streams are contacted with each other once the separation plate is removed. The stacking of the two liquids increases contact area and decreases diffusion length, thereby enhancing the diffusion process.

Mixing and reaction devices can be connected to heat transfer systems if heat management is needed. As with macro-heat exchangers, micro-heat exchanges can either have co-current, counter-current, or cross-flow flow schemes. Microfluidic devices may have channel widths and depths between about 10 μm and about 10 cm. One channel structure includes a long main separation channel, and three shorter "offshoot" side channels terminating in either a buffer, sample, or waste reservoir. The separation channel can be several centimeters long, and the three side channels usually are only a few millimeters in length. Of course, the actual length, cross-sectional area, shape, and branch design of a microfluidic device depends on the application as well other design considerations such as throughput (which depends on flow resistance), velocity profile, residence time, etc.

Microfluidic devices described herein may include one or more electric field generators to perform certain steps of the methods described herein, including, but not limited to, picoinjection, droplet coalescence, selective droplet fusion, and droplet sorting. In certain embodiments, the electric fields are generated using metal electrodes. In particular embodiments, electric fields are generated using liquid electrodes. In certain embodiments, liquid electrodes include liquid electrode channels filled with a conducting liquid (e.g. salt water or buffer) and situated at positions in the microfluidic device where an electric field is desired. In particular embodiments, the liquid electrodes are energized using a power supply or high voltage amplifier. In some embodiments, the liquid electrode channel includes an inlet port so that a conducting liquid can be added to the liquid electrode channel. Such conducting liquid may be added to the liquid electrode channel, for example, by connecting a tube filled with the liquid to the inlet port and applying pressure. In particular embodiments, the liquid electrode channel also includes an outlet port for releasing conducting liquid from the channel. In particular embodiments, the liquid electrodes are used in picoinjection, droplet coalescence, selective droplet fusion, and/or droplet sorting aspects of a microfluidic device described herein. Liquid electrodes may find use, for example, where a material to be injected via application of an electric field is not charged.

In certain embodiments, the width of one or more of the microchannels of the microfluidic device (e.g., input microchannel, pairing microchannel, picoinjection microchannel, and/or a flow channel upstream or downstream of one or more of these channels) is 100 microns or less, e.g., 90 microns or less, 80 microns or less, 70 microns or less, 60 microns or less, 50 microns or less, e.g., 45 microns or less, 40 microns or less, 39 microns or less, 38 microns or less, 37 microns or less, 36 microns or less, 35 microns or less, 34 microns or less, 33 microns or less, 32 microns or less, 31 microns or less, 30 microns or less, 29 microns or less, 28 microns or less, 27 microns or less, 26 microns or less, 25 microns or less, 20 microns or less, 15 microns or less, or 10 microns or less. In some embodiments, the width of one or more of the above microchannels is from about 10 microns to about 15 microns, from about 15 microns to about 20 microns, from about 20 microns to about 25 microns, from about 25 microns to about 30 microns, from about 30 microns to about 35 microns, from about 35 microns to about 40 microns, from about 40 microns to about 45 microns, or from about 45 microns to about 50 microns, from about 50 microns to about 60 microns, from about 60 microns to about 70 microns, from about 70 microns to about 80 microns, from about 80 microns to about 90 microns, or from about 90 microns to about 100 microns. Additional descriptions of various microchannel structures and features which may be utilized in connection with the disclosed methods and devices are provided in PCT Publication No. WO 2014/028378, the disclosure of which is incorporated by reference herein in its entirety and for all purposes.

Methods of Fabrication

According to the disclosed embodiments, microfabrication processes differ depending on the type of materials used in the substrate and/or the desired production volume. For small volume production or prototypes, fabrication techniques include LIGA, powder blasting, laser ablation, mechanical machining, electrical discharge machining, photoforming, etc. Technologies for mass production of microfluidic devices may use either lithographic or master-based replication processes. Lithographic processes for fabricating substrates from silicon/glass include both wet and dry etching techniques commonly used in fabrication of semiconductor devices. Injection molding and hot embossing typically are used for mass production of plastic substrates.

Glass, Silicon and Other "Hard" Materials (Lithography, Etching, Deposition)

According to embodiments of the disclosed subject matter, a combination of lithography, etching and/or deposition techniques may be used to make microcanals and microcavities out of glass, silicon and other "hard" materials. Technologies based on the above techniques may be applied in fabrication of devices in the scale of 0.1-500 micrometers.

Microfabrication techniques based on semiconductor fabrication processes are generally carried out in a clean room. The quality of the clean room is classified by the number of particles <4 μm in size in a cubic inch. Typical clean room classes for MEMS microfabrication may be 1000 to 10000.

In certain embodiments, photolithography may be used in microfabrication. In photolithography, a photoresist that has been deposited on a substrate is exposed to a light source through an optical mask. Conventional photoresist methods allow structural heights of up to 10-40 μm. If higher structures are needed, thicker photoresists such as SU-8, or polyimide, which results in heights of up to 1 mm, can be used.

After transferring the pattern on the mask to the photoresist-covered substrate, the substrate is then etched using either a wet or dry process. In wet etching, the substrate—area not protected by the mask—is subjected to chemical attack in the liquid phase. The liquid reagent used in the etching process depends on whether the etching is isotropic or anisotropic. Isotropic etching generally uses an acid to form three-dimensional structures such as spherical cavities in glass or silicon. Anisotropic etching forms flat surfaces such as wells and canals using a highly basic solvent. Wet anisotropic etching on silicon creates an oblique channel profile.

Dry etching involves attacking the substrate by ions in either a gaseous or plasma phase. Dry etching techniques can be used to create rectangular channel cross-sections and arbitrary channel pathways. Various types of dry etching that may be employed including physical, chemical, physicochemical (e.g., RIE), and physico-chemical with inhibitor. Physical etching uses ions accelerated through an electric field to bombard the substrate's surface to "etch" the structures. Chemical etching may employ an electric field to migrate chemical species to the substrate's surface. The chemical species then reacts with the substrate's surface to produce voids and a volatile species.

In certain embodiments, deposition is used in microfabrication. Deposition techniques can be used to create layers of metals, insulators, semiconductors, polymers, proteins and other organic substances. Most deposition techniques fall into one of two main categories: physical vapor deposition (PVD) and chemical vapor deposition (CVD). In one approach to PVD, a substrate target is contacted with a holding gas (which may be produced by evaporation for example). Certain species in the gas adsorb to the target's surface, forming a layer constituting the deposit. In another approach commonly used in the microelectronics fabrication industry, a target containing the material to be deposited is sputtered with using an argon ion beam or other appropriately energetic source. The sputtered material then deposits on the surface of the microfluidic device. In CVD, species in contact with the target react with the surface, forming components that are chemically bonded to the object. Other deposition techniques include: spin coating, plasma spraying, plasma polymerization, dip coating, casting and Langmuir-Blodgett film deposition. In plasma spraying, a fine powder containing particles of up to 100 µm in diameter is suspended in a carrier gas. The mixture containing the particles is accelerated through a plasma jet and heated. Molten particles splatter onto a substrate and freeze to form a dense coating. Plasma polymerization produces polymer films (e.g. PMMA) from plasma containing organic vapors.

Once the microchannels, microcavities and other features have been etched into the glass or silicon substrate, the etched features are usually sealed to ensure that the microfluidic device is "watertight." When sealing, adhesion can be applied on all surfaces brought into contact with one another. The sealing process may involve fusion techniques such as those developed for bonding between glass-silicon, glass-glass, or silicon-silicon.

Anodic bonding can be used for bonding glass to silicon. A voltage is applied between the glass and silicon and the temperature of the system is elevated to induce the sealing of the surfaces. The electric field and elevated temperature induces the migration of sodium ions in the glass to the glass-silicon interface. The sodium ions in the glass-silicon interface are highly reactive with the silicon surface forming a solid chemical bond between the surfaces. The type of glass used may have a thermal expansion coefficient near that of silicon (e.g. Pyrex Corning 7740).

Fusion bonding can be used for glass-glass or silicon-silicon sealing. The substrates are first forced and aligned together by applying a high contact force. Once in contact, atomic attraction forces (primarily van der Waals forces) hold the substrates together so they can be placed into a furnace and annealed at high temperatures. Depending on the material, temperatures used ranges between about 600 and 1100° C.

Polymers/Plastics

A variety of techniques may be employed for micromachining plastic substrates in accordance with the subject embodiments. Among these are laser ablation, stereolithography, oxygen plasma etching, particle jet ablation, and microelectro-erosion. Some of these techniques can be used to shape other materials (glass, silicon, ceramics, etc.) as well.

To produce multiple copies of a microfluidic device, replication techniques are employed. Such techniques involve first fabricating a master or mold insert containing the pattern to be replicated. The master is then used to mass-produce polymer substrates through polymer replication processes.

In the replication process, the master pattern contained in a mold is replicated onto the polymer structure. In certain embodiments, a polymer and curing agent mix is poured onto a mold under high temperatures. After cooling the mix, the polymer contains the pattern of the mold, and is then removed from the mold. Alternatively, the plastic can be injected into a structure containing a mold insert. In micro-injection, plastic heated to a liquid state is injected into a mold. After separation and cooling, the plastic retains the mold's shape.

PDMS (polydimethylsiloxane), a silicon-based organic polymer, may be employed in the molding process to form microfluidic structures. Because of its elastic character, PDMS is suited for microchannels between about 5 µm and 500 µm. Specific properties of PDMS make it suitable for microfluidic purposes. Such properties include:

1) It is optically clear which allows for visualization of the flows.
2) PDMS, when mixed with a proper amount of reticulating agent, has elastomeric qualities that facilitates keeping microfluidic connections "watertight."
3) Valves and pumps using membranes can be made with PDMS because of its elasticity.
4) Untreated PDMS is hydrophobic, and becomes temporarily hydrophilic after oxidation of surface by oxygen plasma or after immersion in strong base; oxidized PDMS adheres by itself to glass, silicon, or polyethylene, as long as those surfaces were themselves exposed to an oxygen plasma.
5) PDMS is permeable to gas. Filling of the channel with liquids is facilitated even when there are air bubbles in the canal because the air bubbles are forced out of the material. Additionally, PDMS is also permeable to non polar-organic solvents.

Microinjection can be used to form plastic substrates employed in a wide range of microfluidic designs. In this process, a liquid plastic material is first injected into a mold under vacuum and pressure, at a temperature greater than the glass transition temperature of the plastic. The plastic is then cooled below the glass transition temperature. After removing the mold, the resulting plastic structure is the negative of the mold's pattern.

Yet another replicating technique is hot embossing, in which a polymer substrate and a master are heated above the polymer's glass transition temperature, Tg (which for PMMA or PC is around 100-180° C.). The embossing master is then pressed against the substrate with a preset compression force. The system is then cooled below Tg and the mold and substrate are then separated.

Typically, the polymer is subjected to the highest physical forces upon separation from the mold tool, particularly when the microstructure contains high aspect ratios and vertical walls. To avoid damage to the polymer microstructure, material properties of the substrate and the mold tool may be taken into consideration. These properties include: sidewall roughness, sidewall angles, chemical interface between embossing master and substrate and temperature coefficients. High sidewall roughness of the embossing tool can damage the polymer microstructure since roughness contributes to frictional forces between the tool and the structure during the separation process. The microstructure may be destroyed if frictional forces are larger than the local tensile strength of the polymer. Friction between the tool and the substrate may be important in microstructures with vertical walls. The chemical interface between the master and substrate could also be of concern. Because the embossing process subjects the system to elevated temperatures, chemical bonds could form in the master-substrate interface. These interfacial bonds could interfere with the separation process.

Differences in the thermal expansion coefficients of the tool and the substrate could create addition frictional forces.

Various techniques can be employed to form molds, embossing masters, and other masters containing patterns used to replicate plastic structures through the replication processes mentioned above. Examples of such techniques include LIGA (described below), ablation techniques, and various other mechanical machining techniques. Similar techniques can also be used for creating masks, prototypes and microfluidic structures in small volumes. Materials used for the mold tool include metals, metal alloys, silicon and other hard materials.

Laser ablation may be employed to form microstructures either directly on the substrate or through the use of a mask. This technique uses a precision-guided laser, typically with wavelength between infrared and ultraviolet. Laser ablation may be performed on glass and metal substrates, as well as on polymer substrates. Laser ablation can be performed either through moving the substrate surface relative to a fixed laser beam, or moving the beam relative to a fixed substrate. Various micro-wells, canals, and high aspect structures can be made with laser ablation.

Certain materials, such as stainless steel, make durable mold inserts and can be micromachined to form structures down to the 10-µm range. Various other micromachining techniques for microfabrication exist including µ-Electro Discharge Machining (µ-EDM), µ-milling, focused ion beam milling. µ-EDM allows the fabrication of 3-dimensional structures in conducting materials. In µ-EDM, material is removed by high-frequency electric discharge generated between an electrode (cathode tool) and a workpiece (anode). Both the workpiece and the tool are submerged in a dielectric fluid. This technique produces a comparatively rougher surface but offers flexibility in terms of materials and geometries.

Electroplating may be employed for making a replication mold tool/master out of, e.g., a nickel alloy. The process starts with a photolithography step where a photoresist is used to defined structures for electroplating. Areas to be electroplated are free of resist. For structures with high aspect ratios and low roughness requirements, LIGA can be used to produce electroplating forms. LIGA is a German acronym for Lithographic (Lithography), Galvanoformung (electroplating), Abformung (molding). In one approach to LIGA, thick PMMA layers are exposed to x-rays from a synchrotron source. Surfaces created by LIGA have low roughness (around 10 nm RMS) and the resulting nickel tool has good surface chemistry for most polymers.

As with glass and silicon devices, polymeric microfluidic devices must be closed up before they can become functional. Common problems in the bonding process for microfluidic devices include the blocking of channels and changes in the physical parameters of the channels. Lamination is one method used to seal plastic microfluidic devices. In one lamination process, a PET foil (about 30 µm) coated with a melting adhesive layer (typically 5 µm-10 µm) is rolled with a heated roller, onto the microstructure. Through this process, the lid foil is sealed onto the channel plate. Several research groups have reported a bonding by polymerization at interfaces, whereby the structures are heated and force is applied on opposite sides to close the channel. But excessive force applied may damage the microstructures. Both reversible and irreversible bonding techniques exist for plastic-plastic and plastic-glass interfaces. One method of reversible sealing involves first thoroughly rinsing a PDMS substrate and a glass plate (or a second piece of PDMS) with methanol and bringing the surfaces into contact with one another prior to drying. The microstructure is then dried in an oven at 65° C. for 10 min. No clean room is required for this process. Irreversible sealing is accomplished by first thoroughly rinsing the pieces with methanol and then drying them separately with a nitrogen stream. The two pieces are then placed in an air plasma cleaner and oxidized at high power for about 45 seconds. The substrates are then brought into contact with each other and an irreversible seal forms spontaneously.

Other available techniques include laser and ultrasonic welding. In laser welding, polymers are joined together through laser-generated heat. This method has been used in the fabrication of micropumps. Ultrasonic welding is another bonding technique that may be employed in some applications.

One nucleic acid amplification technique described herein is a polymerase chain reaction (PCR). However, in certain embodiments, non-PCR amplification techniques may be employed such as various isothermal nucleic acid amplification techniques; e.g., real-time strand displacement amplification (SDA), rolling-circle amplification (RCA) and multiple-displacement amplification (MDA).

Regarding PCR amplification modules, it will be necessary to provide to such modules at least the building blocks for amplifying nucleic acids (e.g., ample concentrations of four nucleotides), primers, polymerase (e.g., Taq), and appropriate temperature control programs). The polymerase and nucleotide building blocks may be provided in a buffer solution provided via an external port to the amplification module or from an upstream source. In certain embodiments, the buffer stream provided to the sorting module contains some of all the raw materials for nucleic acid amplification. For PCR in particular, precise temperature control of the reacting mixture is extremely important in order to achieve high reaction efficiency. One method of on-chip thermal control is Joule heating in which electrodes are used to heat the fluid inside the module at defined locations. The fluid conductivity may be used as a temperature feedback for power control.

In certain aspects, the discrete entities, e.g., microdroplets, containing the PCR mix may be flowed through a channel that incubates the discrete entities under conditions effective for PCR. Flowing the discrete entities through a channel may involve a channel that snakes over various temperature zones maintained at temperatures effective for PCR. Such channels may, for example, cycle over two or more temperature zones, wherein at least one zone is maintained at about 65° C. and at least one zone is maintained at about 95° C. As the discrete entities move through such zones, their temperature cycles, as needed for PCR. The precise number of zones, and the respective temperature of each zone, may be readily determined by those of skill in the art to achieve the desired PCR amplification.

Exemplary Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-231 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below.

1. A method of delivering discrete entities to a substrate, the method comprising:

flowing a plurality of discrete entities through an air flow via a microfluidic device comprising an air/liquid co-flow junction;

directing the air flow and one or more of the plurality of discrete entities through the air/liquid co-flow junction to the substrate; and affixing the one or more of the plurality of discrete entities to the substrate via a force, wherein the force is selected from a gravitational force, an electrical force, a magnetic force, and combinations thereof.

2. The method of embodiment 1, comprising storing the affixed entity under controlled environmental conditions for a storage period, wherein the force is maintained during the storage period.

3. The method of embodiment 2, wherein the controlled environmental conditions comprise a constant temperature and/or pressure.

4. The method of any one of embodiments 1-3, wherein the force is a gravitational force.

5. The method of any one of embodiments 1-3, wherein the force is an electrical force.

6. The method of embodiment 5, wherein the electrical force is a dielectrophoretic force.

7. The method of any one of embodiments 1-6, wherein the discrete entities are droplets.

8. The method of embodiment 7, wherein the droplets are affixed to the substrate via wetting.

9. The method of embodiment 7, wherein the discrete entities are affixed to the substrate via interfacial tension.

10. The method of any one of embodiments 1-9, wherein the discrete entities have a diameter of from about 1 to 1000 μm.

11. The method of any one of embodiments 1-9, wherein the discrete entities have a volume of from about 1 femtoliter to about 1000 nanoliters.

12. The method of any one of embodiments 1-11, wherein the microfluidic device comprises a sorter, and wherein the method comprises sorting, via the sorter, the one or more of the plurality of discrete entities to be delivered through the air/liquid co-flow junction to the substrate from the plurality of discrete entities.

13. The method of embodiment 12, wherein the plurality of discrete entities is optically scanned prior to the sorting.

14. The method of embodiment 13, wherein the sorting is based on results obtained from the optical scan.

15. The method of any one of embodiments 12-14, wherein the sorter comprises an optical fiber configured to apply excitation energy to one or more of the plurality of discrete entities.

16. The method of embodiment 15, wherein the optical fiber is configured to apply excitation energy to one or more of the plurality of discrete entities and collect a signal produced by the application of the excitation energy to one or more of the plurality of discrete entities.

17. The method of any one of embodiments 12-16, wherein the sorter comprises a second optical fiber configured to collect a signal produced by the application of excitation energy to one or more of the plurality of discrete entities.

18. The method of any one of embodiments 12-17, wherein the sorter is an active sorter.

19. The method of any one of embodiments 12-17, wherein the sorter is a passive sorter.

20. The method of any one of embodiments 12-19, wherein the sorting comprises sorting via dielectrophoresis.

21. The method of any one of embodiments 12-20, wherein the sorter comprises one or more microfluidic valves, and wherein the sorting comprises sorting via activation of the one or more microfluidic valves.

22. The method of any one of embodiments 1-21, wherein the discrete entities are droplets, the microfluidic device comprises a selectively activatable droplet maker which forms droplets from a fluid stream, and wherein the method comprises forming one or more of the plurality of discrete entities via selective activation of the droplet maker.

23. The method of any one of embodiments 1-21, wherein the plurality of discrete entities comprises discrete entities which differ in composition.

24. The method of any one of embodiments 1-23, wherein the microfluidic device is integrated with an automated system which selectively positions the air/liquid co-flow junction relative to the substrate, and wherein the method comprises selectively positioning via the automated system the air/liquid co-flow junction relative to the substrate to selectively deliver the one or more of the plurality of discrete entities to one or more locations on or in proximity to the substrate.

25. The method of any one of embodiments 1-23, wherein the microfluidic device is integrated with an automated system which selectively positions the substrate relative to the air/liquid co-flow junction, and wherein the method comprises selectively positioning via the automated system the substrate relative to the air/liquid co-flow junction to selectively deliver the one or more of the plurality of discrete entities to one or more locations on or in proximity to the substrate.

26. The method of embodiment 24 or 25, wherein the method comprises delivering a first member of the plurality of discrete entities to a first location on or in proximity to the substrate and a second member of the plurality of discrete entities to a second location on or in proximity to the substrate.

27. The method of embodiment 26, wherein the first and second locations are the same.

28. The method of any one of embodiments 1-27, wherein one or more biological assays are performed in one or more of the discrete entities before and/or after delivery to the substrate.

29. The method of any one of embodiments 1-28, wherein the temperature of one or more of the discrete entities is controlled before and/or after delivery to the substrate.

30. The method of embodiment 29, wherein one or more of the discrete entities are thermalcycled before and/or after delivery to the substrate.

31. The method of any one of embodiments 12-30, wherein the members of the plurality of discrete entities which are not sorted for delivery through the air/liquid co-flow junction to the substrate are recovered.

32. The method of embodiment 31, wherein the recovered members of the plurality of discrete entities are recycled such that the method of embodiment 1 is repeated with the recovered members of the plurality of discrete entities.

33. The method of embodiment 32, wherein recovered members of the plurality of discrete entities are continuously recycled during performance of the method.

34. The method of any one of embodiments 1-33, wherein one or more of the plurality of discrete entities comprises a cell.

35. The method of embodiment 34, wherein each member of the plurality of discrete entities comprises not more than one cell.

36. The method of any one of embodiments 1-33, wherein one or more of the plurality of discrete entities comprises a nucleic acid.

37. The method of any one of embodiments 1-33, wherein one or more of the plurality of discrete entities comprises a plurality of materials, and wherein the method comprises subjecting one or more of the affixed discrete entities comprising the plurality of materials to conditions sufficient for assembly of the plurality of the materials.

38. The method of embodiment 37, wherein the plurality of materials comprises a plurality of microparticles and/or nanoparticles.

39. The method of embodiment 37, wherein the plurality of materials comprises one or more metals.

40. The method of embodiment 37, wherein the plurality of materials comprises one or more semiconductor materials.

41. The method of embodiment 37, wherein the plurality of materials comprises one or more organic materials.

42. The method of embodiment 37, wherein the plurality of materials comprises one or more nucleic acids.

43. The method of embodiment 37, wherein the plurality of materials comprises one or more hydrogel materials.

44. The method of embodiment 37, wherein the plurality of materials comprises one or more liquid materials.

45. The method of embodiment 37, wherein the plurality of materials comprises one or more materials having a shape selected from a sphere, a rod, a polyhedron or a star.

46. The method of embodiment 37, wherein the plurality of materials comprises one or more monomers and/or polymers.

47. The method of embodiment 37, wherein the plurality of materials comprises one or more materials having a surface coating.

48. The method of embodiments 47, wherein the surface coating is selected from a charged coating, a hydrophilic coating, a hydrophobic coating, and a coating comprising one or more molecular recognition elements.

49. The method of any one of embodiments 37-48, wherein the assembly comprises one or more covalent bonding interactions between the plurality of materials.

50. The method of any one of embodiments 37-48, wherein the assembly comprises one or more non-covalent bonding interactions between the plurality of materials.

51. The method of any one of embodiments 37-50, wherein subjecting the one or more of the affixed discrete entities comprising the plurality of materials to conditions sufficient for assembly of a plurality of the materials comprises exposing the one or more of the affixed discrete entities comprising the plurality of materials to light, an increase or decrease in temperature, a magnetic force, an electric field (e.g., a frequency modulated electric field), a catalyst, an enzyme (e.g., an enzyme catalyst), a depletion force, and/or conditions sufficient for self-assembly of the plurality of materials.

52. The method of any one of embodiments 37-50, comprising screening the assembled materials for one or more properties.

53. The method of embodiment 52, wherein the one or more properties are selected from conductivity; interactions with electromagnetic radiation, e.g., visible light, UV or IR, such as index of refraction or light scattering; fluorescence; magnetic properties; interactions, e.g., binding interactions, with biological components or entities (e.g., cells (e.g., bacteria or mammalian), fungi or viruses); catalytic properties; buoyancy; and density.

54. The method of any one of embodiments 1-53, wherein the method comprises encapsulating or incorporating one or more reagents into the plurality of discrete entities.

55. The method of embodiment 54, wherein the one or more reagents comprise amplification reagents.

56. The method of embodiment 55, wherein the amplification reagents comprise Polymerase Chain Reaction (PCR) reagents.

57. A method of sorting microdroplets, the method comprising:
   flowing a plurality of microdroplets through a microfluidic device comprising an air/liquid co-flow junction;
   detecting via a detector a property of one or more of the plurality of microdroplets; and
   applying an electric field to selectively deflect one or more of the plurality of microdroplets based on the detection of the property.

58. The method of embodiment 57, wherein the property is an optical property.

59. The method of embodiment 57 or 58, wherein the sorting comprises sorting via dielectrophoresis.

60. A method of treating a wound area comprising printing one or more cell layers on the wound area, wherein the method comprises:
   encapsulating cells in droplets comprising an aqueous fluid to provide cell-comprising droplets;
   flowing a plurality of droplets comprising the cell-comprising droplets through an air flow via a microfluidic device comprising an air/liquid co-flow junction;
   directing the air flow and a plurality of the cell-comprising droplets through the air/liquid co-flow junction to the wound area; and
   affixing the plurality of the cell-comprising droplets to the wound area via a force, wherein the force is selected from a gravitational force, an electrical force, a magnetic force, and combinations thereof, to provide a first layer of cell-comprising droplets.

61. A method of printing one or more cell layers, the method comprising:
   encapsulating cells in droplets comprising an aqueous fluid to provide cell-comprising droplets;
   flowing a plurality of droplets comprising the cell-comprising droplets through an air flow via a microfluidic device comprising an air/liquid co-flow junction;
   directing the air flow and a plurality of the cell-comprising droplets through the air/liquid co-flow junction to a substrate; and affixing the plurality of the cell-comprising droplets to the substrate via a force, wherein the force is selected from a gravitational force, an electrical force, a magnetic force, and combinations thereof, to provide a first layer of cell-comprising droplets.

62. The method of embodiment 60 or embodiment 61, wherein the force is a gravitational force.

63. The method of embodiment 60 or embodiment 61, wherein the force is an electrical force.

64. The method of embodiment 63, wherein the electrical force is a dielectrophoretic force.

65. The method of any one of embodiments 60 or 62-64, wherein the microfluidic device comprises a sorter, and wherein the method comprises sorting, via the sorter, the plurality of cell-comprising droplets to be delivered through the air/liquid co-flow junction to the wound area from the cell-comprising droplets.

66. The method of any one of embodiments 61-64, wherein the microfluidic device comprises a sorter, and wherein the method comprises sorting, via the sorter, the plurality of cell-comprising droplets to be delivered through the air/liquid co-flow junction to the substrate from the cell-comprising droplets.

67. The method of any one of embodiments 60 or 62-65, wherein the method comprises encapsulating or incorporating one or more reagents into droplets to provide reagent-comprising droplets;

flowing a plurality of droplets comprising the reagent-comprising droplets through the microfluidic device; and directing the air flow and a plurality of the reagent-comprising droplets through the air/liquid co-flow junction to the wound area.

68. The method of any one of embodiments 61-64 or 66, wherein the method comprises encapsulating or incorporating one or more reagents into droplets to provide reagent-comprising droplets;

flowing a plurality of droplets comprising the reagent-comprising droplets through the microfluidic device; and directing the air flow and a plurality of the reagent-comprising droplets through the air/liquid co-flow junction to the substrate.

69. The method of embodiment 67 or embodiment 68, wherein the reagent-comprising droplets and the cell-comprising droplets are the same.

70. The method of embodiment 69, wherein cell-comprising droplets and reagent-comprising droplets are deposited in the same layer on the substrate.

71. The method of any one of embodiments 68-70, wherein the one or more reagents comprise a material which facilitates cell growth.

72. The method of embodiment 71, wherein the material which facilitates cell growth comprises a cell culture media component.

73. The method of embodiment 71, wherein the material which facilitates cell growth comprises a cell culture substrate.

74. The method of any one of embodiments 60-73, wherein the method comprises depositing a layer of reagent-comprising droplets on the first layer of cell-comprising droplets thereby providing a layered structure.

75. The method of any one of embodiments 60, 62-65, 67 or 69-74, wherein the method comprises directing the air flow and a second plurality of the cell-comprising droplets through the air/liquid co-flow junction to the wound area; and depositing a second layer of cell-comprising droplets on the first layer of cell-comprising droplets thereby providing a layered structure.

76. The method of any one of embodiments 61-64, 66 or 68-74, wherein the method comprises directing the air flow and a second plurality of the cell-comprising droplets through the air/liquid co-flow junction to the substrate; and depositing a second layer of cell-comprising droplets on the first layer of cell-comprising droplets thereby providing a layered structure.

77. A method of printing and detecting one or more cells, the method comprising:

encapsulating cells in droplets comprising an aqueous fluid to provide cell-comprising droplets;

flowing a plurality of droplets comprising the cell-comprising droplets through an air flow via a micro-fluidic device comprising an air/liquid co-flow junction;

directing the air flow and a plurality of the cell-comprising droplets through the air/liquid co-flow junction to a substrate;

affixing the plurality of the cell-comprising droplets to the substrate via a force, wherein the force is selected from a gravitational force, an electrical force, a magnetic force, and combinations thereof, to provide a first layer of cell-comprising droplets; and detecting one or more of the cells in the affixed cell-comprising droplets, a component of one or more of the cells in the affixed cell-comprising droplets or a product of one or more of the cells in the affixed cell-comprising droplets.

78. The method of embodiment 77, wherein the force is a gravitational force.

79. The method of embodiment 77, wherein the force is an electrical force.

80. The method of embodiment 79, wherein the electrical force is a dielectrophoretic force.

81. The method of any one of embodiments 77-80, wherein the detecting is performed at a plurality of time points.

82. The method of any one of embodiments 77-81, wherein the method comprises continuously detecting over a period of time one or more of the cells in the affixed cell-comprising droplets, a component of one or more of the cells in the affixed cell-comprising droplets or a product of one or more of the cells in the affixed cell-comprising droplets.

83. The method of any one of embodiments 77-82, comprising recovering from the affixed cell-comprising droplets one or more of the cells in the affixed cell-comprising droplets, a component of one or more of the cells in the affixed cell-comprising droplets or a product of one or more of the cells in the affixed cell-comprising droplets.

84. The method of embodiment 83, comprising recovering DNA from one or more of the cells in the affixed cell-comprising droplets.

85. A method of printing a three-dimensional structure, the method comprising:

flowing discrete entities through an air flow via a microfluidic device comprising an air/liquid co-flow junction;

directing the air flow and a first plurality of the discrete entities through the air/liquid co-flow junction to a substrate;

affixing the first plurality of the discrete entities to the substrate via a force, wherein the force is selected from a gravitational force, an electrical force, a magnetic force, and combinations thereof, to provide a first layer thereon;

directing the air flow and a second plurality of the discrete entities through the air/liquid co-flow junction to the first layer;

affixing the second plurality of the discrete entities to the substrate via a force, wherein the force is selected from a gravitational force, an electrical force, a magnetic force, and combinations thereof, to provide a second layer thereon; and one or more additional directing steps in which a plurality of the discrete entities are directed through the air/liquid co-flow junction to an immediately preceding layer to provide a subsequent layer thereon, wherein a multilayer, three-dimensional structure is provided.

86. The method of embodiment 85, wherein the force is a gravitational force.

87. The method of embodiment 85, wherein the force is an electrical force.

88. The method of embodiment 87, wherein the electrical force is a dielectrophoretic force.

89. The method of any one of embodiments 85-88, wherein the discrete entities are hydrophilic.

90. The method of embodiment 89, wherein the discrete entities are droplets.

91. The method of embodiment 90, wherein the droplets comprise an aqueous fluid.

92. The method of any one of embodiments 85-88, wherein the discrete entities are hydrophobic.

93. The method of embodiment 92, wherein the discrete entities are droplets.

94. The method of embodiment 89 or embodiment 92, wherein the discrete entities consist of a solid material.

95. The method of embodiment 89 or embodiment 92, wherein the discrete entities consist of a gel material.

96. The method of any one of embodiments 85-89, 92, 94 or 95 comprising initiating a reaction which causes the discrete entities to solidify.

97. The method of embodiment 96, wherein the reaction is a photopolymerization reaction.

98. A method of delivering droplets from an air/liquid co-flow junction, the method comprising:

flowing a plurality of droplets through an air flow via a microfluidic device, wherein the microfluidic device comprises an air/liquid co-flow junction and a sorter;

detecting one or more of the plurality of droplets to provide one or more detected droplets;

sorting via the sorter the one or more detected droplets from the plurality of droplets; and directing the air flow and the one or more detected droplets through the air/liquid co-flow junction.

99. The method of embodiment 98, comprising depositing the one or more detected droplets on a substrate.

100. A method of affixing a droplet to a substrate, the method comprising:

delivering a droplet in an air flow from a microfluidic device comprising an air/liquid co-flow junction, through the air/liquid co-flow junction, to a substrate surface;

positioning the droplet on the substrate surface; and affixing the droplet to the substrate surface via a force, wherein the force is selected from a gravitational force, an electrical force, a magnetic force, and combinations thereof.

101. The method of embodiment 100, wherein the force is a gravitational force.

102. The method of embodiment 100, wherein the wettability of the substrate is sufficient to affix the droplet to the substrate via wetting forces.

103. The method of embodiment 100, comprising modifying the wettability of the substrate so as to be sufficient to affix the droplet to the substrate via wetting forces.

104. The method of embodiment 100, wherein the method comprises applying exogenous electromagnetic radiation sufficient to affix the droplet to a specific location on the substrate surface.

105. The method of embodiment 100, wherein the force is an electrical force.

106. The method of embodiment 105, wherein the electrical force is a dielectrophoretic force.

107. The method of any one of embodiments 100, 105 or 106, wherein the substrate comprises a plurality of channels filled with a conductive liquid or solid material and an insulating sheet, wherein the plurality of channels are patterned to generate a dielectrophoretic force sufficient to affix the droplet to the substrate surface.

108. The method of any one of embodiments 100 or 105-107, wherein the substrate and the droplet have net charges which are opposite in polarity.

109. The method of any one of embodiments 100 or 105-108, wherein the substrate comprises a plurality of channels filled with a conductive liquid or solid material and an insulating sheet, wherein the plurality of channels are patterned to generate an electric field gradient above the insulating sheet upon application of a voltage, and wherein the method comprises applying a voltage to one or more of the plurality of channels sufficient to generate the electrical field gradient, wherein the electrical field gradient produces a dielectrophoretic force sufficient to affix the droplet to the substrate surface.

110. The method of any one of embodiments 100 or 105-108, wherein the substrate comprises a plurality of channels filled with a conductive liquid or solid material and an insulating sheet, wherein the plurality of channels are patterned to provide a plurality of electrode features, and wherein the plurality of electrode features are positioned relative to each other so as to provide positions on the substrate surface capable of reducing droplet interfacial energy when a voltage is applied to one or more of the plurality of channels, and wherein the positions are sufficient to affix the droplet to the substrate surface.

111. The method of embodiment 110, wherein at least one electrode feature is positioned relative to at least one other electrode feature such that there is a gap between the features, wherein the distance of the gap is within an order of magnitude of the diameter of the droplet.

112. The method of embodiment 111, comprising affixing the droplet in proximity to the gap.

113. A method of moving an affixed droplet on a substrate, the method comprising:

delivering a droplet in an air flow from a microfluidic device comprising an air/liquid co-flow junction, through the air/liquid co-flow junction, to a substrate surface;

affixing the droplet to the substrate surface via a force, wherein the force is selected from a gravitational force, an electrical force, a magnetic force, and combinations thereof; and modulating the force so as to move the droplet from its affixed location to another location and/or applying a second force, which is sufficient, either alone or in combination with the modulated force, to move the droplet from its affixed location to another location.

114. The method of embodiment 113, wherein the method comprises applying exogenous electromagnetic radiation sufficient to move the droplet from its affixed location to another location.

115. The method of embodiment 113, wherein the method comprises introducing a cross flow of fluid which is sufficient to move the droplet from its affixed location to another location.

116. The method of embodiment 113, wherein the force is a gravitational force.

117. The method of embodiment 113, wherein the force is an electrical force.

118. The method of embodiment 117, wherein the electrical force is a dielectrophoretic force.

119. The method of any one of embodiments 113, 117 or 118, wherein the substrate comprises a plurality of channels filled with a conductive liquid or solid material and an insulating sheet, wherein the plurality of channels are patterned to generate an electric field gradient above the insulating sheet upon application of a voltage, and wherein the method comprises applying a voltage to one or more of the plurality of channels sufficient to generate the electrical field gradient, wherein the electrical field gradient produced a dielectrophoretic force sufficient to affix the droplet to the substrate surface.

120. The method of embodiment 119, comprising modulating the electrical field so as to move the droplet from its affixed location to another location.

121. A method of adding reagents to a droplet, the method comprising:

delivering a first droplet in an air flow from a microfluidic device comprising an air/liquid co-flow junction, through the air/liquid co-flow junction, to a substrate surface;

affixing the droplet to the substrate surface via a force, wherein the force is selected from a gravitational force, an electrical force, a magnetic force, and combinations thereof;

delivering a second droplet comprising a reagent to the same location as the first droplet affixed to the substrate surface or a location adjacent the first droplet on the substrate surface; and coalescing the first droplet and the second droplet such that the contents of the first droplet and the second droplet are combined.

122. The method of embodiment 121, wherein the force is a gravitational force.

123. The method of embodiment 121, wherein the force is an electrical force.

124. The method of embodiment 123, wherein the electrical force is a dielectrophoretic force.

125. The method of any one of embodiments 121-124, wherein multiple droplets are delivered to the same location as the first droplet affixed to the substrate surface or a location adjacent the first droplet on the substrate surface, and wherein the multiple droplets are coalesced with the first droplet such that the contents of the first droplet and the multiple droplets are combined.

126. The method of any one of embodiments 121-125, wherein coalescence is triggered via application of a force to one or more of the droplets.

127. The method of any one of embodiments 121-126, wherein coalescence occurs spontaneously.

128. The method of embodiment 127, wherein the force is an electrical force.

129. The method of embodiment 128, wherein the electrical force is a dielectrophoretic force.

130. A method of adding reagents to a droplet, the method comprising:

delivering a droplet in an air flow from a microfluidic device comprising an air/liquid co-flow junction, through the air/liquid co-flow junction, to a substrate surface;

affixing the droplet to the substrate surface via a force, wherein the force is selected from a gravitational force, an electrical force, a magnetic force, and combinations thereof;

inserting an orifice fluidically connected to a reagent source into the droplet; and injecting via the orifice one or more reagents into the droplet.

131. The method of embodiment 130, wherein the force is a gravitational force.

132. The method of embodiment 130, wherein the force is an electrical force.

133. The method of embodiment 132, wherein the electrical force is a dielectrophoretic force.

134. A method of recovering all or a portion of the affixed droplet, the method comprising:

delivering a droplet in an air flow from a microfluidic device comprising an air/liquid co-flow junction, through the air/liquid co-flow junction, to a substrate surface;

affixing the droplet to the substrate surface via a force, wherein the force is selected from a gravitational force, an electrical force, a magnetic force, and combinations thereof; and recovering all or a portion of the affixed droplet.

135. The method of embodiment 134, wherein the force is a gravitational force.

136. The method of embodiment 134, wherein the force is an electrical force.

137. The method of embodiment 136, wherein the electrical force is a dielectrophoretic force.

138. The method of any one of embodiments 134-137, wherein the recovering comprises modulating one or more forces acting on the affixed droplet.

139. The method of any one of embodiments 134-137, wherein the recovering comprises contacting the affixed droplet with a microfluidic orifice fluidically connected to a suction device to recover all or a portion of the affixed droplet from the substrate surface.

140. The method of any one of embodiments 134-137, wherein the recovering comprises bringing in proximity to the affixed droplet a microfluidic orifice fluidically connected to a suction device to recover the affixed droplet from the substrate surface.

141. The method of any one of embodiments 134-137, wherein the recovering comprises inserting into the affixed droplet a microfluidic orifice fluidically connected to a suction device to recover all or a portion of the contents of the affixed droplet.

142. The method of any one of embodiments 134-137, wherein the recovering comprises shearing the affixed droplet from the substrate surface.

143. The method of any one of embodiments 134-137, wherein the recovering comprises increasing the buoyancy of the affixed droplet such that buoyancy forces acting on the affixed droplet are sufficient to overcome the force affixing the droplet to the substrate surface, thereby releasing the affixed droplet from the substrate surface.

144. The method of embodiment 143, wherein increasing the buoyancy of the affixed droplet comprises increasing the volume of the affixed droplet.

145. The method of embodiment 144, wherein the volume of the affixed droplet is increased by injecting an aqueous fluid into the affixed droplet.

146. The method of any one of embodiments 134-137, wherein the recovering comprises modulating the force affixing the droplet to the substrate surface such that the droplet is released from the substrate surface.

147. The method of embodiment 146, wherein the modulating comprises removing the force.

148. The method of any one of embodiments 134-147, wherein the droplet comprises one or more beads.

149. The method of embodiment 148, wherein the one or more beads comprise a binding agent which selectively binds one or more materials present in the droplet.

150. The method of embodiment 148 or 149, wherein the one or more beads are buoyant within the droplet.

151. The method of embodiment 148 or 149 wherein the one or more beads are selected from magnetic beads and conductive beads.

152. The method of any one of embodiments 148-151, comprising positioning and/or concentrating the one or more beads in a first region of the droplet leaving a second region which is relatively devoid of beads.

153. The method of embodiment 152, comprising selectively recovering from the droplet the one or more beads from the first region.

154. The method of embodiment 152, comprising selectively recovering material from the second region of the droplet.

155. The method of any one of embodiments 134-154, comprising delivering the recovered droplet or the recovered portion of the droplet to one or more isolated containers via an orifice.

156. A method of manipulating an affixed droplet, the method comprising:
    delivering a droplet in an air flow from a microfluidic device comprising an air/liquid co-flow junction, through the air/liquid co-flow junction, to a substrate surface;
    affixing the droplet to the substrate surface via a force, wherein the force is selected from a gravitational force, an electrical force, a magnetic force, and combinations thereof; and
    modulating the immediate environment of the droplet, thereby modulating the contents of the droplet.

157. The method of embodiment 156, wherein the force is a gravitational force.

158. The method of embodiment 156, wherein the force is an electrical force.

159. The method of embodiment 158, wherein the electrical force is a dielectrophoretic force.

160. The method of any one of embodiments 156-159, wherein the modulating comprises modulating a parameter selected from a chemical composition of the immediate environment, a temperature of the immediate environment, a pH of the immediate environment, a pressure of the immediate environment, and a radiation level of the immediate environment.

161. The method of any one of embodiments 156-160, wherein the substrate surface is selectively permeable, the substrate comprises a fluid volume positioned beneath and in contact with the selectively permeable substrate surface, and the immediate environment of the droplet is modulated by modulating one or more of a chemical composition of the fluid volume, a temperature of the fluid volume, a pH of the fluid volume, a pressure of the fluid volume, and a radiation level of the fluid volume.

162. The method of embodiment 161, wherein the fluid volume is a fluid flow.

163. The method of any one of embodiments 156-162, wherein the substrate comprises patterned electrodes positioned beneath the fluid volume.

164. The method of any one of embodiments 156-163, comprising storing the affixed droplet under controlled environmental conditions for a storage period, wherein the force is maintained during the storage period.

165. The method of embodiment 164, wherein the controlled environmental conditions comprise a constant temperature and/or pressure.

166. The method of any one of embodiments 156-165, comprising at least partially solidifying the affixed droplet.

167. A method of manipulating an affixed droplet, the method comprising:
    delivering a droplet in an air flow from a microfluidic device comprising an air/liquid co-flow junction, through the air/liquid co-flow junction, to a substrate surface;
    affixing the droplet to the substrate surface via a force, wherein the force is selected from a gravitational force, an electrical force, a magnetic force, and combinations thereof;
    at least partially solidifying the affixed droplet;
    adding a miscible fluid to the affixed droplet; and modulating a chemical composition of the miscible fluid, thereby modulating the affixed droplet.

168. The method of embodiment 167, wherein the force is a gravitational force.

169. The method of embodiment 167, wherein the force is an electrical force.

170. The method of embodiment 169, wherein the electrical force is a dielectrophoretic force.

171. A method of porating a cell within an affixed droplet, the method comprising:
    delivering a droplet in an air flow from a microfluidic device comprising an air/liquid co-flow junction, through the air/liquid co-flow junction, to a substrate surface, wherein the droplet comprises a cell;
    positioning the droplet on the substrate surface;
    affixing the droplet to the substrate surface via a force, wherein the force is selected from a gravitational force, an electrical force, a magnetic force, and combinations thereof; and
    porating the cell within the droplet.

172. The method of embodiment 171, wherein the force is a gravitational force.

173. The method of embodiment 171, wherein the force is an electrical force.

174. The method of embodiment 173, wherein the electrical force is a dielectrophoretic force.

175. The method of any one of embodiments 171-174, wherein the cell is porated using electrical, chemical or sonic means.

176. The method of any one of embodiments 171-175, comprising introducing one or more nucleic acids into the porated cell.

177. The method of any one of embodiments 171-176, wherein the poration occurs within the microfluidic device.

178. The method of any one of embodiments 171-176, wherein the poration occurs after delivery through the air/liquid co-flow junction and prior to affixing the droplet to the substrate surface.

179. The method of any one of embodiments 171-176, wherein the poration occurs after the droplet is affixed to the substrate surface.

180. The method of any one of embodiments 171-176, wherein the poration occurs in the microfluidic device prior to delivery through the air/liquid co-flow junction.

181. The method of embodiment 180, wherein the droplet is delivered to the substrate surface in proximity to a second droplet positioned on the substrate surface, wherein the second droplet comprises a nucleic acid, and wherein the method comprises merging the droplet with the second droplet to contact the nucleic acid with the porated cell.

182. A method of delivering discrete entities to a substrate, the method comprising:

flowing a plurality of first discrete entities in an air flow through a microfluidic device comprising a first air/liquid co-flow junction;

directing the one or more of the plurality of first discrete entities through the first air/liquid co-flow junction to the substrate;

flowing a plurality of second discrete entities through a second microfluidic comprising a second air/liquid co-flow junction device;

directing the one or more of the plurality of second discrete entities through the second air/liquid co-flow junction to the substrate; and affixing the one or more of the plurality of first discrete entities and the one or more of the plurality of second discrete entities to the substrate via a force, wherein the force is selected from a gravitational force, an electrical force, a magnetic force, and combinations thereof.

183. The method of embodiment 182, wherein the force is a gravitational force.

184. The method of embodiment 182, wherein the force is an electrical force.

185. The method of embodiment 184, wherein the electrical force is a dielectrophoretic force.

186. The method of any one of embodiments 182-185, wherein the first discrete entities and/or the second discrete entities are droplets.

187. The method of embodiment 186, wherein the droplets are affixed to the substrate.

188. The method of any one of embodiments 182-187, wherein the first microfluidic device and the second microfluidic device are integrated with an automated system which selectively positions the air/liquid co-flow junctions relative to the substrate, and wherein the method comprises selectively positioning via the automated system the air/liquid co-flow junctions relative to the substrate to selectively deliver the plurality of first discrete entities and the plurality of second discrete entities to one or more locations on or in proximity to the substrate.

189. The method of any one of embodiments 182-187, wherein the first microfluidic device and the second microfluidic device are integrated with an automated system which selectively positions the substrate relative to the air/liquid co-flow junctions, and wherein the method comprises selectively positioning via the automated system the substrate relative to the air/liquid co-flow junctions to selectively deliver the plurality of first discrete entities and the plurality of second discrete entities to one or more locations on or in proximity to the substrate.

190. A method of delivering discrete entities to a substrate, the method comprising:

flowing a plurality of discrete entities in an air flow through a microfluidic device comprising an air/liquid co-flow junction, wherein the microfluidic device comprises a plurality of air/liquid co-flow junctions;

directing the one or more of the plurality of discrete entities through a first air/liquid co-flow junction of the plurality of air/liquid co-flow junctions to the substrate;

directing a second one or more of the plurality of discrete entities through a second air/liquid co-flow junction of the plurality of air/liquid co-flow junctions to the substrate; and affixing the first one or more of the plurality of first discrete entities and the second one or more of the plurality of discrete entities to the substrate via a force, wherein the force is selected from a gravitational force, an electrical force, a magnetic force, and combinations thereof.

191. The method of embodiment 190, wherein the force is a gravitational force.

192. The method of embodiment 190, wherein the force is an electrical force.

193. The method of embodiment 192, wherein the electrical force is a dielectrophoretic force.

194. The method of any one of embodiments 190-193, wherein the discrete entities are droplets.

195. The method of embodiment 194, wherein the droplets are affixed to the substrate.

196. The method of any one of embodiments 190-195, wherein the microfluidic device is integrated with an automated system which selectively positions the air/liquid co-flow junctions relative to the substrate, and wherein the method comprises selectively positioning via the automated system the air/liquid co-flow junctions relative to the substrate to selectively deliver the first one or more of the plurality of discrete entities and the second one or more of the plurality of discrete entities to one or more locations on or in proximity to the substrate.

197. The method of any one of embodiments 190-195, wherein the microfluidic device is integrated with an automated system which selectively positions the substrate relative to the air/liquid co-flow junctions, and wherein the method comprises selectively positioning via the automated system the substrate relative to the air/liquid co-flow junctions to selectively deliver the first one or more of the plurality of discrete entities and the second one or more of the plurality of discrete entities to one or more locations on or in proximity to the substrate.

198. A method of synthesizing a polymer on a substrate, the method comprising:

flowing a first droplet in an air flow through a microfluidic device comprising an air/liquid co-flow junction, wherein the first droplet comprises a first polymer or a first monomer;

directing the first droplet through the air/liquid co-flow junction to the substrate;

affixing the first droplet to the substrate via a force, wherein the force is selected from a gravitational force, an electrical force, a magnetic force, and combinations thereof;

flowing a second droplet in an air flow through the microfluidic device, wherein the second droplet comprises a second polymer or a second monomer;

directing the second droplet through the air/liquid co-flow junction to the first droplet affixed at the predetermined location; and incubating the first and second droplets under conditions sufficient for the contents of the first and second droplets to come into contact and for the first polymer or first monomer to form a covalent bond with the second polymer or monomer, thereby generating a synthesized polymer.

199. The method of embodiment 198, wherein the force is a gravitational force.

200. The method of embodiment 198, wherein the force is an electrical force.

201. The method of embodiment 200, wherein the electrical force is a dielectrophoretic force.

202. The method of any one of embodiments 198-201, wherein the incubating comprises incubating the first and second droplets under conditions sufficient for droplet coalescence.

203. The method of any one of embodiments 198-202, wherein the synthesized polymer is a polypeptide.

204. The method of any one of embodiments 198-202, wherein the synthesized polymer is a nucleic acid.

205. A method of printing microarrays, the method comprising:

delivering a plurality of droplets in an air flow from a microfluidic device comprising an air/liquid co-flow junction, through the air/liquid co-flow junction, to a substrate surface, wherein each of the plurality of droplets comprises a molecule;

positioning the droplets on the substrate surface;

affixing the droplets at predetermined locations to the substrate surface via a force, wherein the force is selected from a gravitational force, an electrical force, a magnetic force, and combinations thereof; and incubating the substrate under conditions suitable for chemical bonding of the molecules comprised by the affixed droplets to the substrate surface, thereby providing an array of substrate-bound molecules.

206. The method of embodiment 205, wherein the force is a gravitational force.

207. The method of embodiment 205, wherein the force is an electrical force.

208. The method of embodiment 207, wherein the electrical force is a dielectrophoretic force.

209. A method of manipulating cells or embryos, the method comprising:

flowing a plurality of droplets in an air flow through a microfluidic device comprising an air/liquid co-flow junction, wherein each droplet of the plurality of droplets comprises an aqueous fluid and a fertilized egg cell or embryo;

directing the plurality of droplets through the air/liquid co-flow junction to a substrate;

affixing the plurality of droplets to the substrate via a force, wherein the force is selected from a gravitational force, an electrical force, a magnetic force, and combinations thereof, wherein the substrate comprises on a surface thereof a layer of fluid;

detecting within the affixed plurality of droplets the development of one or more embryos; and selecting and recovering an embryo from the affixed droplets.

210. The method of embodiment 209, wherein the force is a gravitational force.

211. The method of embodiment 209, wherein the force is an electrical force.

212. The method of embodiment 211, wherein the electrical force is a dielectrophoretic force.

213. A method of manipulating cells or embryos, the method comprising:

flowing a plurality of droplets in an air flow through a microfluidic device comprising an air/liquid co-flow junction, wherein each droplet of the plurality of droplets comprises an aqueous fluid and an unfertilized egg cell;

directing the plurality of droplets through the air/liquid co-flow junction to a substrate;

fertilizing one or more of the egg cells in the plurality of droplets;

affixing the plurality of droplets to the substrate, via a force, wherein the force is selected from a gravitational force, an electrical force, a magnetic force, and combinations thereof, wherein the substrate comprises on a surface thereof a layer of fluid;

detecting within the affixed droplets the development of an embryo; and selecting and recovering specific embryos from the affixed droplets.

214. The method of embodiment 213, wherein the force is a gravitational force.

215. The method of embodiment 213, wherein the force is an electrical force.

216. The method of embodiment 215, wherein the electrical force is a dielectrophoretic force.

217. The method of any one of embodiments 213-216, wherein the fertilizing occurs after the affixing.

218. A droplet printer comprising:

a microfluidic device comprising an air/liquid co-flow junction;

one or more droplet makers and one or more flow channels, wherein the one or more flow channels are fluidically connected to the one or more droplet makers and configured to receive one or more droplets therefrom;

the air/liquid co-flow junction connected to one or more of the one or more flow channels and one or more air channels, wherein the one or more air channels are connected to one or more air flow controllers;

a droplet sorter, which selectively sorts droplets; and an automated system integrated with the air/liquid co-flow junction, wherein the automated system (a) selectively positions the air/liquid co-flow junction in proximity to a substrate during operation or (b)

selectively positions the substrate in proximity to the air/liquid co-flow junction during operation, such that a droplet can be ejected from the air/liquid co-flow junction and deposited on the substrate.

219. The droplet printer of embodiment 218, wherein the droplet sorter comprises an array of individually controllable electrodes.

220. The droplet printer of embodiment 218 or 219, wherein the microfluidic device comprises a temperature control module which is capable of modulating the temperature in the one or more flow channels.

221. The droplet printer of embodiment 219, wherein the temperature control module is a thermal cycler.

222. The droplet printer of any one of embodiments 218-221, comprising a detection means capable of detecting one or more droplets or one or more droplet components.

223. The droplet printer of embodiment 222, wherein the detection means is an optical imager.

224. The droplet printer of embodiment 222 or embodiment 223, wherein the sorting is based on detecting one or more droplets or one or more droplet components.

225. A system comprising:
a droplet printer as set forth in any one of embodiments 218-224;
a substrate surface for receiving one or more droplets deposited by the air/liquid co-flow junction of the droplet printer; and
one or more of:
(a) a temperature control module operably connected to the droplet printer,
(b) a detection means operably connected to the droplet printer, and
(c) an incubator operably connected to the droplet printer, and
a conveyor configured to convey the substrate from a first droplet receiving position to one or more of (a)-(c).

226. The system of embodiment 225, further comprising:
a power source; and
a controller, wherein the controller is configured to selectively enable or disable an electrical connection between the power source and each individually controllable electrode in the array thereby providing an active or inactive electrode respectively, and wherein, each active electrode is capable of affixing a droplet to a surface of the substrate material in proximity to the active electrode when said droplet is deposited in proximity to the active electrode.

227. A microfluidic device comprising:
an air/liquid co-flow junction;
one or more flow channels;
one or more air channels;
one or more air flow controllers connected to the one or more air channels; and
an electrode configured to selectively apply an electric field.

228. The microfluidic device of embodiment 227, comprising a waste reservoir connected to a vacuum pump.

229. A system comprising a microfluidic device as set forth in embodiment 227 or embodiment 228, and an optical detector configured to detect an optical property of one or microdroplets upstream of the location of the application of the electric field by the electrode.

230. A system comprising:
a microfluidic device in any one of embodiments 227-229;

a substrate surface for receiving one or more discrete entities deposited by the air/liquid co-flow junction of the microfluidic device; and
one or more of:
(a) a temperature control module operably connected to the microfluidic device,
(b) a detection means operably connected to the microfluidic device, and
(c) an incubator operably connected to the microfluidic device, and
a conveyor configured to convey the substrate from a first discrete entity receiving position to one or more of (a)-(c).

231. The system of embodiment 230, further comprising:
a power source; and
a controller, wherein the controller is configured to selectively enable or disable an electrical connection between the power source and each individually controllable electrode in the array thereby providing an active or inactive electrode respectively, and wherein, each active electrode is capable of affixing a discrete entity to a surface of the substrate material in proximity to the active electrode when said discrete entity is deposited in proximity to the active electrode.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); and the like.

Example 1: Printer Head Fabrication, Configuration and Operation

Printer head fabrication: The printer heads were based on microfluidic chips fabricated in poly(dimethylsiloxane) (PDMS) using soft lithography. To form the droplets in printer head without oil, the 3D air/liquid co-flow junction was used. Two masters were used to construct the 3D geometry in the chip. For the master with liquid channel, a 30-um tall layer of SU-8 photoresist was firstly spun onto a silicon wafer, baked, and patterned with a photomask to provide the liquid channel thickness. And then, an additional 70 um of SU-8 was spun onto the baked SU-8, baked, and photopatterned to serve as part of the geometry of air channel and insertions of the fibers. Last, another 60 um of SU-8 was spun onto the wafer to provide the thickness of channels for electrodes and waste collection tubing. For the other master, a 70-um of SU-8 was spun to serve as a thickness for mirror parts of air flow channels and fiber channels. Subsequently, an additional 60 um of SU-8 was spun to provide the thickness of electrode channel and waste collection tubing channel mirrors. The wafer was then developed using the developer, after that uncured PDMS (10:1 polymer to cross-linker ratio) was poured onto these masters. PDMS was cured in an oven at 80° C. for 80 min, and then these slabs were extracted from the masters with a scalpel. The flow channels were punched using a 0.75-mm biopsy core. These two slabs were bonded together with precise alignment after oxygen plasma treatment. When doing the bonding, about 1 mL water was added into the bonding interface to serve as a lubricant so that the alignment could be carefully carried out. The aligned chips were then put into the oven with temperature of 60° C. for two days to completely evaporate the water and fully be bonded.

Printer head fluidics, optical and sorting system configuration: The printer head used an air/liquid co-flow junction to form the droplets which were subsequently used for printing. To precisely control the air flow, the air firstly went through the air flow controllers which were controlled by the customer made software. The liquid phase was injected into the chip using a syringe pump. In the junction, the liquid could be dispersed into droplets by the air flow and then ejected out of the printer head.

Before insertion into respective channels in the chip, all optical fibers (Torlabs, Newton, NJ) were firstly stripped. It should be noted that, unlike the previous PDM system, the stripped fibers were coated with liquid metal and this design rendered it a "Faraday moat" function which was necessary to isolate the junction from the electric field produced by the electrode when do sorting. The excitation and emission fibers had the identical specifications with a cladding diameter of 225 μm, an optical core diameter of 200 μm, and an NA of 0.22. Excitation light was delivered from the multimode fiber combined by coupling fibers to 100-mW, continuous-wave lasers with wavelengths of 405, 473, 532, and 640 nm (CNI Lasers, Changchun, China). Each laser power was adjusted to the final power reaching end of excitation fibers at ~1 mW. Emitted light was collected by the emission fibers which was ported to an optical setup where it is columnated, filtered, and redirected by a series of dichroic mirrors to the emission detection PMTs (Thorlabs) with bandpass filters centered at 448 nm, 510 nm, 571 nm, and 697 nm.

The tip of tubing inserted in the waste collection was cut with a triangular shape by the razor. When doing insertion, tune the open inner channel to face the droplet ejection direction. The electrode was made with a solder, and its spherical tip with diameter of about 0.8 mm was formed due to surface tension when solidifying after melting at high temperature. Tune the distance between electrode tip and ejected droplet to about 0.15 mm. Align the electrode tip and collection tubing at the same plane as that of the ejected droplets.

Printer operation: The printing process was automated by a custom-made LabVIEW software. The printer head was held by a XYZ manipulator, and printing substrate was placed on a XY mechanical stage controlled by the software. When do printing, the high voltage amplifier (690E-6, Trek, Lockport, NY) connected to the sorting electrode was turned on to provide a DC voltage so that all ejected droplets were deflected owing to the dielectrophoresis. Tune the DC voltage to about 2 kV so that all of them could be deflected into the collection tubing. Optical detection data was acquired by a field programmable gate array (FPGA, National Instruments, Austin, TX) and subsequently input into the software. Sorting was actuated by triggering an interval electrical signal to temporarily turn off the amplifier so that the sorted droplet kept the initial ejection direction onto the printing substrate.

Characterization of droplet formation by the printer: For droplet formation analysis, droplets were ejected into an oil (Novec HFE-7500, 3M, supplemented with 0.2% wt/wt biocompatible surfactant) layer which was dropped on a glass slide. The collected droplets floating on the oil layer was transferred into the count slide using a pipette, imaged by the EVOS, and analyzed by the ImageJ software. PEG 8000 or Ethylene glycol was mixed with water to get liquid phases with different Z numbers. Two geometry designs of printer head, with rectangular liquid channel of 30 μm and 70 μm, were used to investigate the scale effect on the droplet formation.

Example 2: Microfluidics Printer Enables Single Cell Sorting with High Accuracy and High Viability Preparation of cells for printing: NIH 3T3 cells were cultured in 75-cm² flasks with base medium of Dulbecco's Modified Eagle Medium (DMEM) containing 4.5 g/L glucose, 0.584 g/L L-glutamine, and 3.7 g/L NaHCO₃. Complete growth medium was obtained by supplementing DMEM with 10% FBS and 10% antibiotics. Subculturing was performed when cells were grown to about 75% confluency. For subculturing, after removing the culture medium and briefly rinsing the cell layer with 5 mL 0.25% Trypsin—0.53 mM EDTA, 3 mL of 0.25% Trypsin—0.53 mM EDTA was added into the flask to dislodge the cells. After 10 min, add 8 mL of complete growth medium into the flask and transfer cell suspension into a tube. Aliquot of 1 mL of cell suspension was used for new cell culture, and the others were used for cell printing preparation. Cells were resuspended into PBS for staining. For viability and proliferation assays in FIG. 6, Panels A and B, and spheroid formation assays in FIG. 8, Panels A and B, CellTracker™ Green CMFDA dye (5 uM final concentration), or CellTracker™ Red CMTPX dye (10 uM final concentration) was used to stain the cells due to their low cytotocicity. For cell arrays and patterns printing in FIG. 6, Panels A and B, 5 uM final concentration of either Calcein Green, AM, Calcein Red-Orange, AM, or CellTrace™ Far Red was used to stain the cells. After staining for 15 min in the incubator, cells were washed two times with 10 mL cold PBS. Stained cells were resuspended into complete growth medium with a final concentration of 1.5 million/mL for printing. Cell count was measured by TC20 automated cell counter (BioRa). FITC-dextran (final concentration 5 uM) was added the final cell suspensions to serve as the background fluorescence dye.

Evaluation of sorting throughput, stability and accuracy: Droplet formation throughput was controlled by changing the liquid phase flow rate using the syringe pump. For throughput experiments, PBS was used and the sorting process was monitored by a high-speed camera. When performing the sorting stability, the droplet formation was kept at about 300 Hz and droplet sorting was actuated every 25 ms. The entire process was monitored by the high-speed camera and subsequently analyzed to get the stability data. For evaluation of cell sorting accuracy in FIG. 6, Panel A, left, Calcein green, AM, stained NIH 3T3 cells were suspended in the culture medium with final concentration of 1 million/mL. Sorted droplets were collected into 96 wells with 200 μL oil of Novec HFE-7500 supplemented with 0.2% wt/wt biocompatible surfactant in each well. After sorting, 100 μL mineral oil was added into the well so that the sorted droplet could get into the center of the liquid due to the surface tension balance. For evaluation of sorting accuracy with multiple types of cells, Calcein green, AM, and Calcein red-orange, AM, stained NIH 3T3 cells were mixed together with a final cell concentration of 1.5 million/mL. Sorted droplets were collected into 96 wells with 200 μL medium in each well.

Cell viability and proliferation analysis after cell sorting: NIH 3T3 cells and Jurkat cells were used to evaluate the viability after sorting respectively. All cells were stained with CellTracker™ Green CMFDA and with a concentration of 1.5 million/mL. About 1000 cells were sorted into one well of 96 wells with 200 μL medium. After sorting, 0.5 uL of Ethidium Homodimer-1 (EthD-1) with a concentration of 5 mM was added into the well, followed by incubation in the incubator for 15 min. Viability was examined via EVOS image systems. For the control group, about 1000 cells under the same conditions were added into the wells using pipette, and viability evaluation was performed in the same method as sorted cells. For cell proliferation evaluation, about 1000 NIH 3T3 cells by sorting and pipetting were added into the wells respectively. The cell growth was monitored by the EVOS image systems every day. Before imaging, 0.5 uL of Calcein green, AM with a concentration of 1 mM was added into the wells to stain cells. Cells in each well for imaging were just used one time at the staining day to exclude the staining effect on viability analysis.

Example 3: Microfluidics Printer Enables High-Resolution Printing of Multiple Types of Single Cells Characterization of droplet printing and single cell printing: Droplet printing was performed with droplet formation at a frequency of about 500 Hz. PBS stained with 100 μM fluorescein (FITC) was used as the liquid phase. Uncured PDMS was spin-coated onto the glass slide with a final thickness of about 50 μm. The PDMS coated glass slides were used as printing substrates. For printing accuracy analysis in FIG. 7, Panel A, printing was performed with a distance between delivery orifice and substrate of 3 mm, 4 mm, 5 mm, and 6 mm, respectively. For droplet arrays printing in FIG. 7, Panel A, the distance between delivery orifice and substrate was set of 3 mm. For single cell printing in FIG. 7, Panels B-D, NIH 3T3 cell suspensions with a cell concentration of 1.5 million/mL were used as the liquid phase. In FIG. 7, Panel B, Calcein green, AM and Calcein red-orange, AM were used to stain the cells. The distance between two spot was 400 μm. In FIG. 7, Panel C (bottom), Calcein green, AM stained cells were used to print "UCSF" pattern with different printed cell density. The distance between two neighboring droplet was 20 μm and 10 μm for upper one and lower one, respectively. In FIG. 7, Panel C, Calcein green, AM and Calcein red-orange, AM (top) stained cells were used for the pattern printing with distance between two neighboring droplet of 20 μm. In FIG. 7, Panel D, Calcein green, AM, and Calcein red-orange, AM stained cells were used for pattern printing on used for printing well-defined cell clusters into nanowells.

Example 4: Microfluidics Printer Enables Controllable Formation of Spheroids 96-well ultralow attachment microplates with round bottom (Corning) were used as the substrate for spheroid formation in FIG. 8, Panels C-E. A certain number of NIH 3T3 cells were printed into the wells with 200 μL complete growth medium. Passive loading spheroid formation was performed by pipetting 1 uL, 2 uL, 4 uL and 10 uL of NIH 3T3 cell suspensions (cell concentration 0.05 million/mL)

into the wells with 200 μL complete growth medium to get an assumed cell number of 50, 100, 200, and 500. After printing and passive loading, well plates were centrifuged for 20 min at 300 rpm, and then incubated in the incubator. The sizes of spheroids were measured using the EVOS image systems after two days of culturing. For dynamically adding cells into spheroids, about 200 CellTracker Green CMFDA stained NIH 3T3 cells were firstly printed into each well. After one-day culture, another certain number of CellTracker™ Red CMTPX stained NIH 3T3 cells were printed into the wells.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of delivering discrete entities to a substrate, the method comprising:

flowing a plurality of discrete entities through an air flow via a microfluidic device comprising an air/liquid co-flow junction, wherein the air/liquid co-flow junction is connected to one or more air channels through which the air flow can be applied;

directing the air flow and one or more of the plurality of discrete entities through the air/liquid co-flow junction to the substrate; and affixing the one or more of the plurality of discrete entities to the substrate via a force, wherein the force is selected from a gravitational force, an electrical force, a magnetic force, and combinations thereof.

2. The method of claim 1, comprising storing the affixed entity under controlled environmental conditions for a storage period, wherein the force is maintained during the storage period.

3. The method of claim 2, wherein the controlled environmental conditions comprise a constant temperature and/or pressure.

4. The method of claim 1, wherein the force is a gravitational force.

5. The method of claim 1, wherein the force is an electrical force.

6. The method of claim 5, wherein the electrical force is a dielectrophoretic force.

7. The method of claim 1, wherein the discrete entities are droplets.

8. The method of claim 7, wherein the droplets are affixed to the substrate via wetting.

9. The method of claim 7, wherein the discrete entities are affixed to the substrate via interfacial tension.

10. The method of claim 1, wherein the discrete entities have a diameter of from about 1 to 1000 μm.

11. The method of claim 1, wherein the discrete entities have a volume of from about 1 femtoliter to about 1000 nanoliters.

12. The method of claim 1, wherein the microfluidic device comprises a sorter, and wherein the method comprises sorting, via the sorter, the one or more of the plurality of discrete entities to be delivered through the air/liquid co-flow junction to the substrate from the plurality of discrete entities.

13. The method of claim 12, wherein the plurality of discrete entities is optically scanned prior to the sorting.

14. The method of claim 13, wherein the sorting is based on results obtained from the optical scan.

15. The method of claim 12, wherein the sorter comprises an optical fiber configured to apply excitation energy to one or more of the plurality of discrete entities.

16. The method of claim 15, wherein the optical fiber is configured to apply excitation energy to one or more of the plurality of discrete entities and collect a signal produced by the application of the excitation energy to one or more of the plurality of discrete entities.

17. The method of claim 12, wherein the sorter comprises a second optical fiber configured to collect a signal produced by the application of excitation energy to one or more of the plurality of discrete entities.

18. The method of claim 12, wherein the sorter is an active sorter.

19. The method of claim 12, wherein the sorter is a passive sorter.

20. The method of claim 12, wherein the sorting comprises sorting via dielectrophoresis.

21. The method of claim 12, wherein the sorter comprises one or more microfluidic valves, and wherein the sorting comprises sorting via activation of the one or more microfluidic valves.

22. The method of claim 1, wherein the discrete entities are droplets, the microfluidic device comprises a selectively activatable droplet maker which forms droplets from a fluid stream, and wherein the method comprises forming one or more of the plurality of discrete entities via selective activation of the droplet maker.

23. The method of claim 1, wherein the plurality of discrete entities comprises discrete entities which differ in composition.

24. The method of claim 1, wherein the microfluidic device is integrated with an automated system which selectively positions the air/liquid co-flow junction relative to the substrate, and wherein the method comprises selectively positioning via the automated system the air/liquid co-flow junction relative to the substrate to selectively deliver the one or more of the plurality of discrete entities to one or more locations on or in proximity to the substrate.

25. The method of claim 1, wherein the microfluidic device is integrated with an automated system which selectively positions the substrate relative to the air/liquid co-flow junction, and wherein the method comprises selectively positioning via the automated system the substrate relative to the air/liquid co-flow junction to selectively deliver the one or more of the plurality of discrete entities to one or more locations on or in proximity to the substrate.

26. The method of claim 24, wherein the method comprises delivering a first member of the plurality of discrete entities to a first location on or in proximity to the substrate and a second member of the plurality of discrete entities to a second location on or in proximity to the substrate.

27. The method of claim 1, wherein one or more of the plurality of discrete entities comprises a cell.

28. The method of claim 27, wherein each member of the plurality of discrete entities comprises not more than one cell.

29. The method of claim 1, wherein one or more of the plurality of discrete entities comprises a nucleic acid.

30. The method of claim 1, wherein one or more of the plurality of discrete entities comprises a plurality of materials, and wherein the method comprises subjecting one or more of the affixed discrete entities comprising the plurality of materials to conditions sufficient for assembly of the plurality of the materials.

31. The method of claim 1, wherein one or more air channels are connected to air flow controllers to control and direct the air flow in the one or more air channels.

\*　\*　\*　\*　\*